(12) United States Patent
Jang et al.

(10) Patent No.: US 10,003,031 B2
(45) Date of Patent: Jun. 19, 2018

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUKSAN HIGH METAL CO., LTD., Ulsan (KR)

(72) Inventors: Jaewan Jang, Cheonan-si (KR); Sunhee Lee, Cheonan-si (KR); Wonsam Kim, Cheonan-si (KR); Hyeryeong Kim, Cheonan-si (KR); Junghwan Park, Hwaseong-si (KR); Gyumin Lee, Cheonan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 396 days.

(21) Appl. No.: 14/650,460

(22) PCT Filed: Nov. 29, 2013

(86) PCT No.: PCT/KR2013/010955
§ 371 (c)(1),
(2) Date: Jun. 8, 2015

(87) PCT Pub. No.: WO2014/092362
PCT Pub. Date: Jun. 19, 2014

(65) Prior Publication Data
US 2015/0349276 A1    Dec. 3, 2015

(30) Foreign Application Priority Data

Dec. 11, 2012 (KR) .................. 10-2012-0143954
Nov. 28, 2013 (KR) .................. 10-2013-0146114

(51) Int. Cl.
*H01L 51/00* (2006.01)
*C07D 495/04* (2006.01)
(Continued)

(52) U.S. Cl.
CPC ........ *H01L 51/0072* (2013.01); *C07B 59/002* (2013.01); *C07D 209/94* (2013.01);
(Continued)

(58) Field of Classification Search
CPC ............ H01L 51/0072; H01L 51/0074; H01L 51/0071; H01L 51/006; H01L 51/0061;
(Continued)

(56) References Cited

FOREIGN PATENT DOCUMENTS

JP    2007-329454 A    12/2007
JP    2012-4116 A    1/2012
(Continued)

OTHER PUBLICATIONS

Curiel et al., "Synthesis and Characterization of New Carbazolocarbazoles: Toward Pi-Extended N-Fused Heteroacenes", Organic Letters, vol. 12, No. 14, pp. 3164-3167, (2010). Abstract Only.
(Continued)

*Primary Examiner* — Ruiyun Zhang
(74) *Attorney, Agent, or Firm* — Vorys, Sater, Seymour & Pease LLP; Mih Suhn Koh

(57) ABSTRACT

Provided herein are a compound capable of improving light emitting efficiency, stability, and lifespan of the element, an organic element using the same, and an electric device for the same.

8 Claims, 1 Drawing Sheet

(51) Int. Cl.
    *C07D 491/04* (2006.01)
    *G09G 3/3225* (2016.01)
    *C07D 209/94* (2006.01)
    *C07F 7/08* (2006.01)
    *C07B 59/00* (2006.01)
    *H01L 51/50* (2006.01)

(52) U.S. Cl.
    CPC ......... *C07D 491/04* (2013.01); *C07D 495/04* (2013.01); *C07F 7/0816* (2013.01); *G09G 3/3225* (2013.01); *H01L 51/006* (2013.01); *H01L 51/0061* (2013.01); *H01L 51/0071* (2013.01); *H01L 51/0094* (2013.01); *H01L 51/0052* (2013.01); *H01L 51/0059* (2013.01); *H01L 51/50* (2013.01); *H01L 51/5016* (2013.01); *H01L 51/5056* (2013.01); *Y02E 10/549* (2013.01)

(58) Field of Classification Search
    CPC . H01L 51/0052; H01L 51/0059; H01L 51/50; H01L 51/5016; C07B 59/002; C07D 209/94; C07D 491/04; C07D 495/04; C07F 7/0816; G09G 3/3225

USPC ............ 428/690, 917; 252/301.16; 544/212, 544/213; 585/26
    See application file for complete search history.

(56) References Cited

FOREIGN PATENT DOCUMENTS

| | | |
|---|---|---|
| JP | 2012-186496 A | 9/2012 |
| JP | 2013-150557 A | 8/2013 |
| JP | 2014-24844 A | 2/2014 |
| KR | 10-2010-0007780 A | 1/2010 |
| WO | 2010-126234 A1 | 11/2010 |
| WO | 2013-094999 A2 | 6/2013 |

OTHER PUBLICATIONS

Liu et al., "Theoretical Prediction of One- and Two-Photon Absorption Properties of N-Annulated Quaterrylenes as near-Infrared Chromophores", J. Organic Chemistry, vol. 77, pp. 585-597, (2012). Abstract Only.

Japanese Office Action, dated May 20, 2016, four pages.

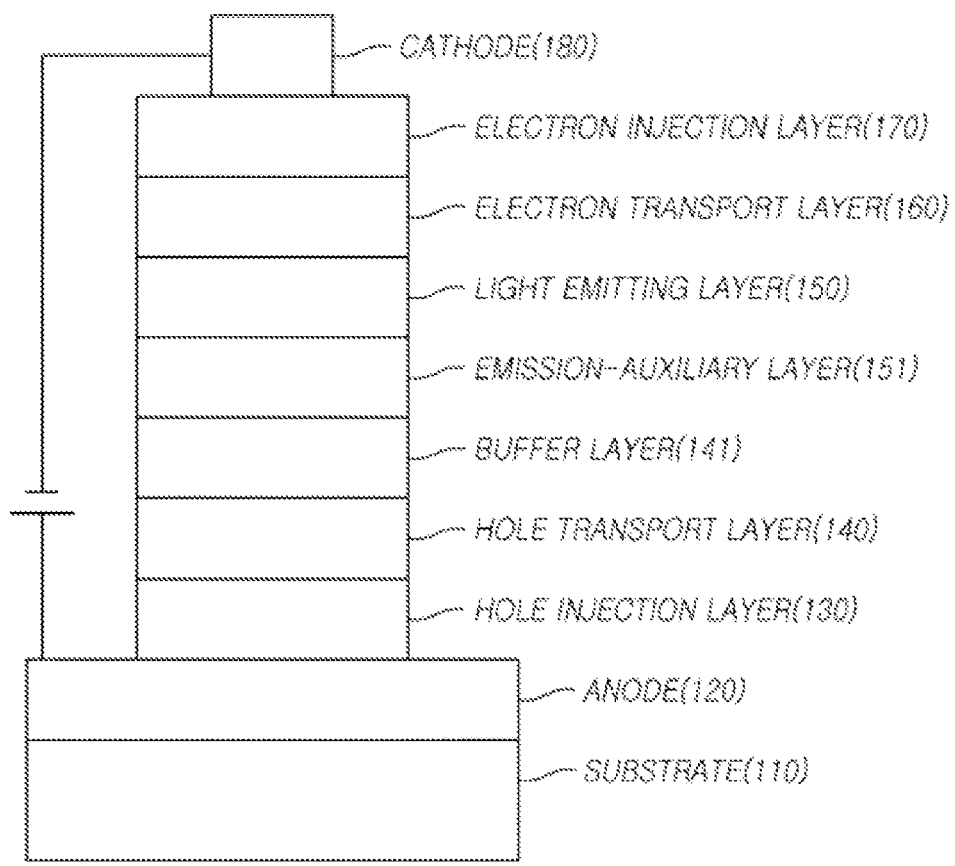

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under 35 U.S.C. § 119(a) of Korean Patent Application No. 10-2012-0143954, filed on Dec. 11, 2012, and Korean Patent Application No. 10-2013-0146114, filed on Nov. 28, 2013, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other.

For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Accordingly, there is a need for the development of luminescent materials that are of high thermal stability and which exhibit an efficient charge balance in a light emitting layer, and especially for the development of a host material of the light emitting layer.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. When light emission occurs in an interface of the hole transporting layer, the organic electroluminescent device suffers from the disadvantage of a reduction in color purity, efficiency, and lifespan. Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems occurring in the prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, there is provided compounds represented by the formula below.

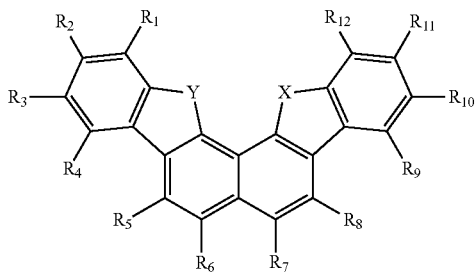

In another aspect of the present invention, there are provided organic electric elements using the compound represented by the formula above and electronic devices including the organic electric element.

By using the compound according to embodiments of the present invention, an organic electric element according to one or more embodiments of the present invention not only has high luminous efficiency, low driving voltage and high heat-resistant and, but can also be significantly improved in color purity, luminous efficiency, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxy group" or "alkenyloxy group" as used herein means an oxygen radical attached to an alkenyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group.

Unless otherwise stated, the term "heterocyclic group" as used herein contains one or more heteroatoms, but not limited to, has 2 to 60 carbon atoms, includes both monocyclic and polycyclic rings, and may include alicyclic and/or aromatic group containing heteroatoms. Also, the heterocyclic group may also be formed in conjunction with an adjacent group.

Unless otherwise stated, the term "heteroatom" as used herein represents at least one of N, O, S, P, and Si.

Also, the term "heterocyclic group" may include $SO_2$ instead of carbon consisting of cycle. For example, "heterocyclic group" includes compound below.

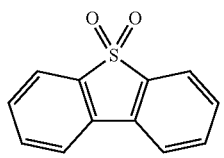 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula.

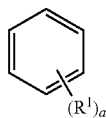

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. When a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

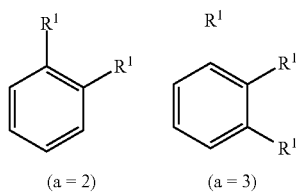

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer or an emission-auxiliary layer by using the compound represented by Formula 1, and thus the life span and efficiency of the organic electric element can be improved at the same time.

The organic electric element according to an embodiment of the present invention may be manufactured using a PVD (physical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

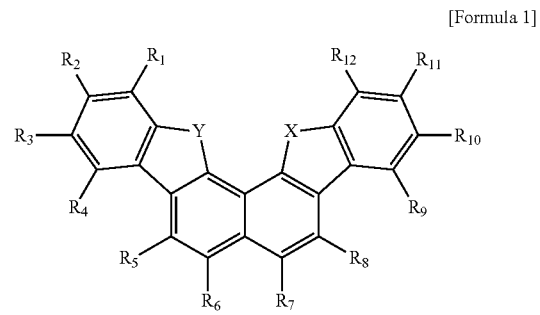

[Formula 1]

In Formula 1 above, $R_1$ to $R_{12}$ may be i) independently selected from the group consisting of hydrogen, deuterium, tritium, halogen, a $C_6$-$C_{60}$ aryl group, a $C_2$-$C_{60}$ heterocyclic group containing at least one heteroatom selected from O, N, S, Si, and P, a $C_1$-$C_{60}$ alkyl group, a $C_2$-$C_{60}$ alkenyl group, a $C_1$-$C_{30}$ alkoxy group, a fluorenyl group, and -$L^1$-N(R')(R'') or ii) any adjacent groups of $R_1$ to $R_{12}$ can be independently linked together to form at least one fused ring. Here, $R_1$ to $R_{12}$ that don't form a fused ring can be as defined above i).

As used herein, the term "adjacent groups can be linked together form at least one ring" means that a combination occurs between $R_1$ and $R_2$, between $R_2$ and $R_3$, between $R_3$ and $R_4$, between $R_5$ and $R_6$, between $R_7$ and $R_8$, between $R_9$ and $R_{10}$, between $R_{10}$ and $R_{11}$, and/or between $R_{11}$ and $R_{12}$ to form one or more rings. In this regard, since it is important that adjacent groups are combined to form a ring, the scope of the present invention is not limited by any substituents on the groups or by the reaction for forming the ring. The ring may be formed by a well-known reaction (the Heck reaction, or a reaction described in Chem. Eur. J. 2009, 15, 742, Molecules. 2008, 13, 3236-3245, J. Am. Chem. Soc. 2008, 130, 472-480, Tetrahedron Letters. 1997, 38, 4761-4764).

The ring that is formed as adjacent groups among $R_1$ to $R_{12}$ are linked with each other may be a monocyclic or polycyclic aromatic ring or a heterocyclic ring containing at least one heteroatom therein, or a fuse ring in which an aromatic ring and an aliphatic ring are fused together. For example, when the adjacent groups among $R_1$ to $R_4$ are combined to each other, an aromatic ring, such as benzene, naphthalene, phenanthrene, and the like, may be formed. It is preferable that the aromatic ring formed have 6 to 60 carbon atoms. For example, when benzene rings are formed by combining $R_1$ with $R_2$, and $R_3$ with $R_4$, respectively, a phenanthrene is formed with the benzene ring backbone.

Also, a heterocyclic ring, such as thiophene, furan, pyridine, indole, quinolone, and the like, may be formed by combining the adjacent groups among $R_1$ to $R_{12}$ to one another. Here, the heterocyclic ring may have 2 to 60 carbon atoms. Also, when the ring is polycyclic, it may have a structure in which a plurality of rings is fused or not fused. Alternatively, the polycyclic ring may have a fused ring and a non-fused ring in mixture.

X and Y may be independently NR', S, O, CR'R'' or SiR'R''. wherein R' and R'' may be i) independently selected from the group consisting of a $C_6$-$C_{60}$ aryl group, a $C_2$-$C_{60}$ heterocyclic group containing at least one heteroatom selected from O, N, S, Si, and P, a fluorenyl group, a $C_1$-$C_{60}$ alkyl group and -L-N(Ar$_1$)(Ar$_2$) or ii) R' and R'' can be optionally linked together to form a spiro compound together with C or Si which they are linked with.

L may be selected from the group consisting of a single bond, a $C_6$-$C_{60}$ arylene group, a fluorenylene group, and a $C_2$-$C_{60}$ heterocyclic group containing at least one heteroatom selected from O, N, S, Si, and P and a divalent aliphatic hydrocarbon group. Here, "single bond" means that L is nonexistent. As a result, when L is single bond, $R_1$ to $R_{12}$ become —N($Ar_1$)($Ar_2$).

The above $Ar_1$ and $Ar_2$ may be independently selected from the group consisting of a $C_6$-$C_{60}$ aryl group, a fluorenyl group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, and a $C_1$-$C_{30}$ alkoxy group.

The aryl group, fluorenyl group, heterocyclic group, alkyl group, alkenyl group, alkoxy group, arylene group, fluorenylene group and aliphatic hydrocarbon group of $Ar_1$, $Ar_2$, L, $R_1$ to $R_{12}$, R' and R" may be substituted by one or more substituents selected from the group consisting of deuterium, halogen, a silane group, a siloxane group, a boron group, a germanium group, a cyano group, a nitro group, amine group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Specially, the compound represented by Formula 1 above may be represented by one of Formulae below.

[Formula 2]

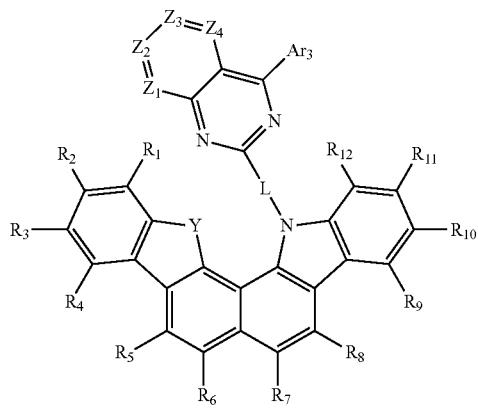

[Formula 3]

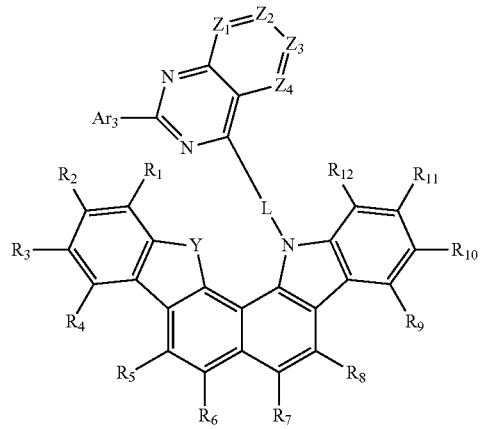

In Formula 2 and Formula 3, $Ar_3$ may be selected from the group consisting of a $C_6$-$C_{60}$ aryl group, a $C_2$-$C_{20}$ alkenyl group, a $C_2$-$C_{60}$ heterocyclic group containing at least one heteroatom selected from the group consisting of O, N, S, Si, and P, a $C_1$-$C_{50}$ alkyl group, and a substituted with a $C_1$-$C_{20}$ alkyl group or unsubstituted fluorenyl group.

In Formula 2 and Formula 3 above, $Z_1$~$Z_4$ may be independently CR' or N, and $R_1$ to $R_{12}$, Y, L and R' may be as defined in Formula 1 above.

More specially, the compound represented by Formula 1 to Formula 3 above may be one of compounds below.

P-1

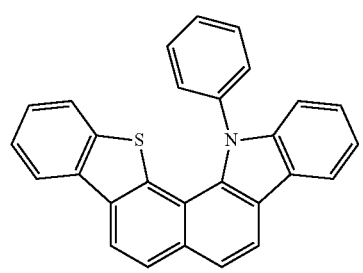

P-2

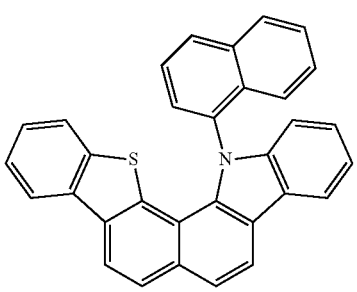

-continued
P-3
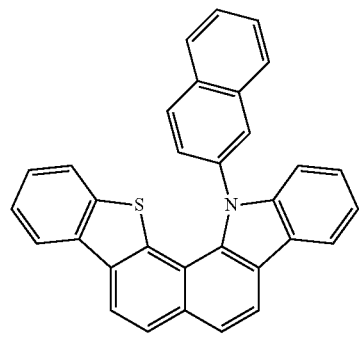
P-4
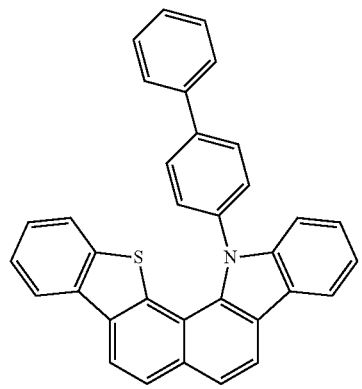
P-5
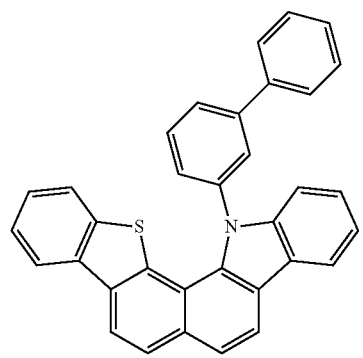
P-6
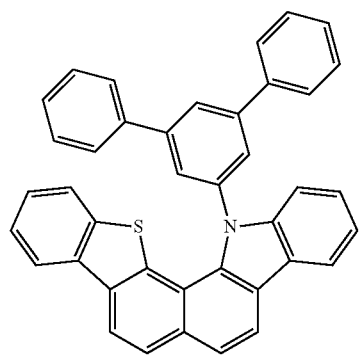
P-7
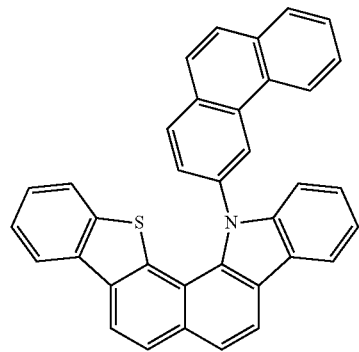
P-8
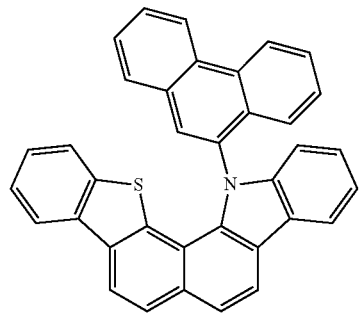
P-9
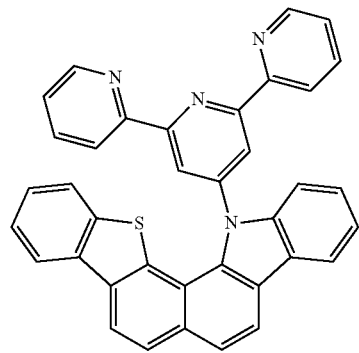
P-10
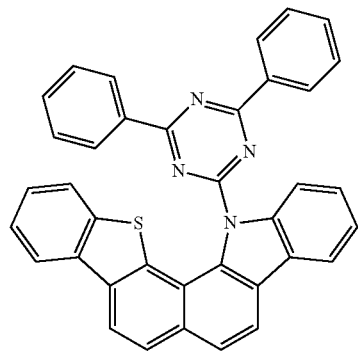

-continued
P-11
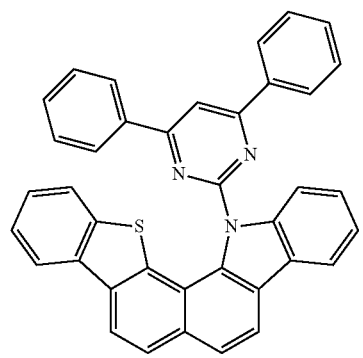
P-12
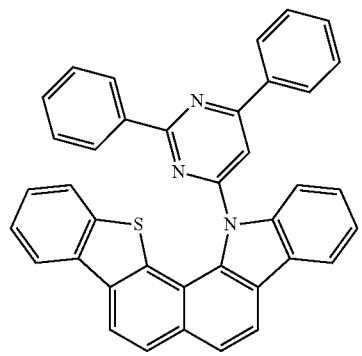
P-13
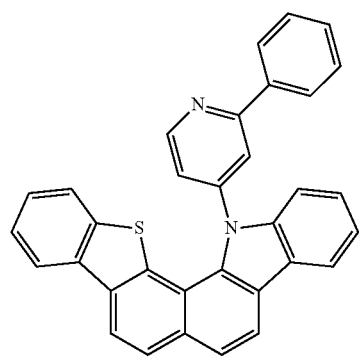
P-14
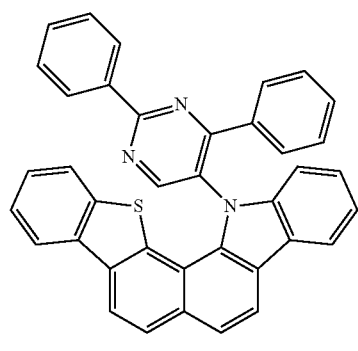
P-15
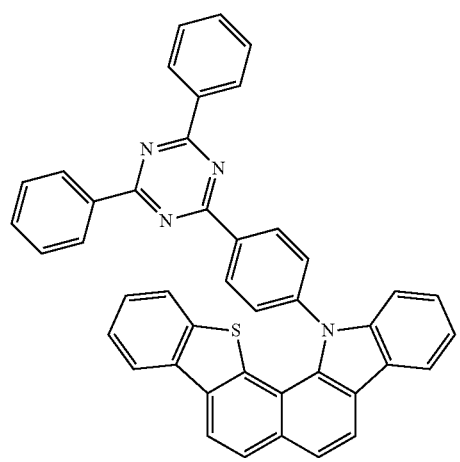
P-16
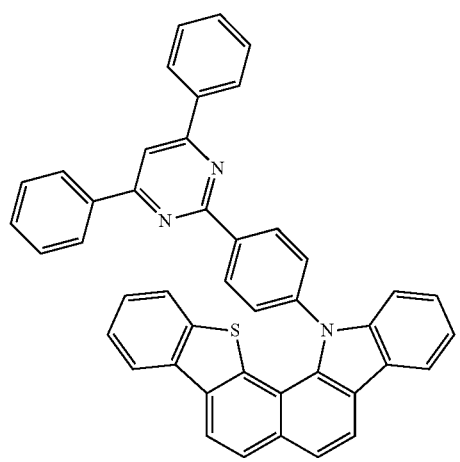
P-17
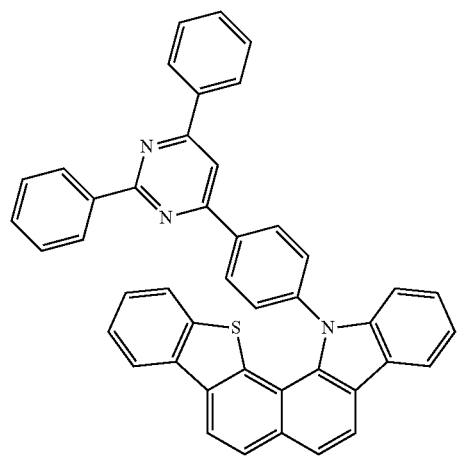
P-18
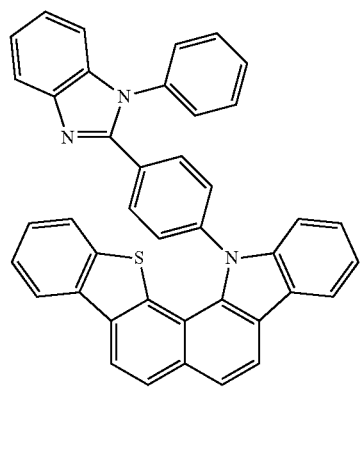

-continued
P-19
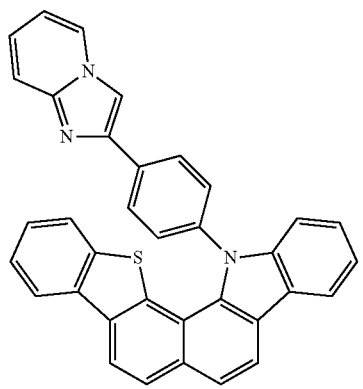
P-20
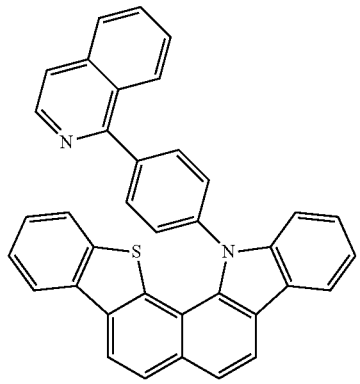
P-21
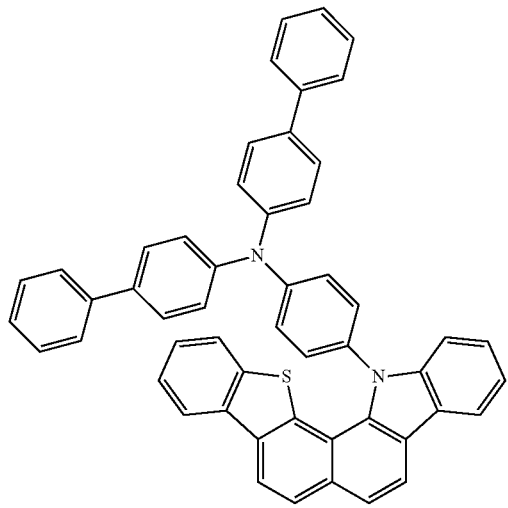
P-22
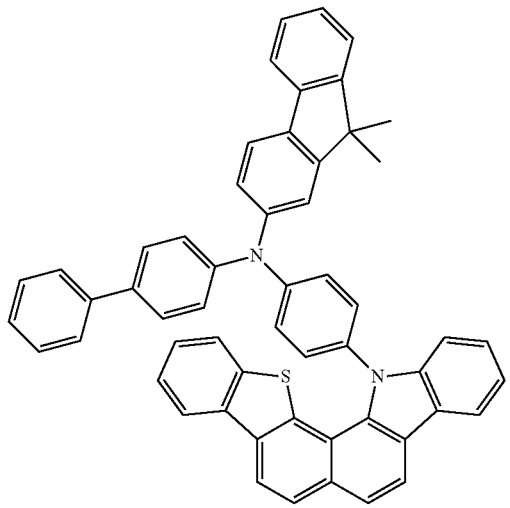
P-23
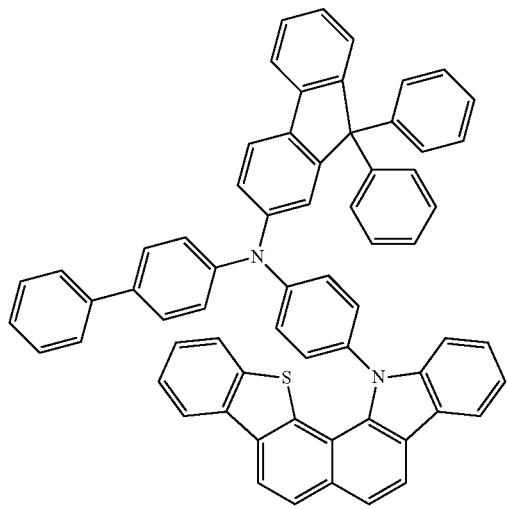
P-24
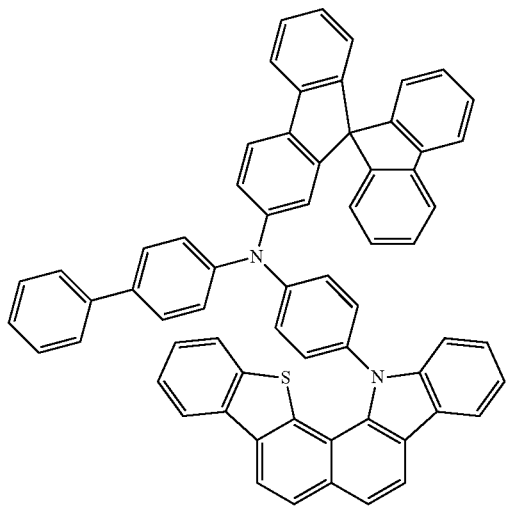

-continued
P-25
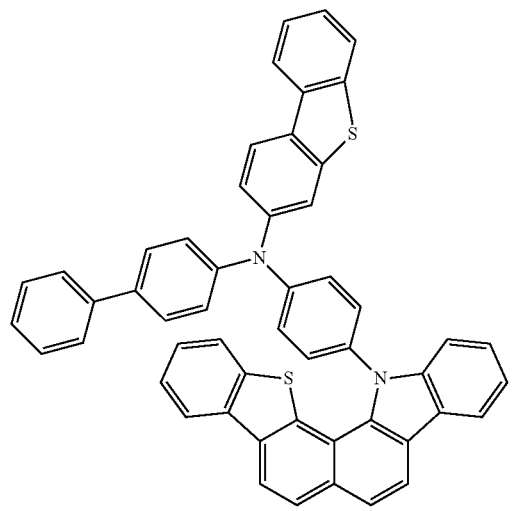
P-26
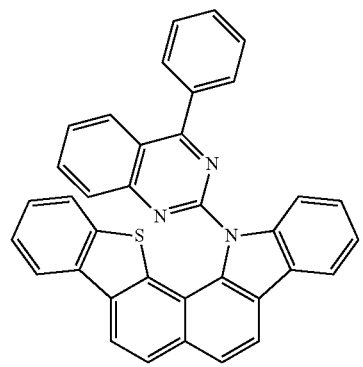
P-27
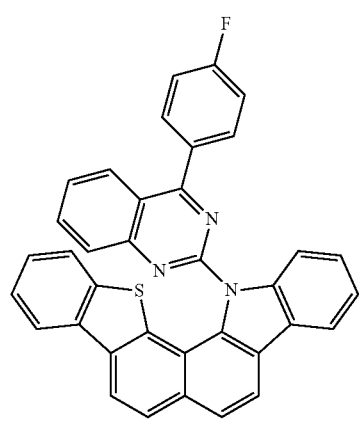
P-28
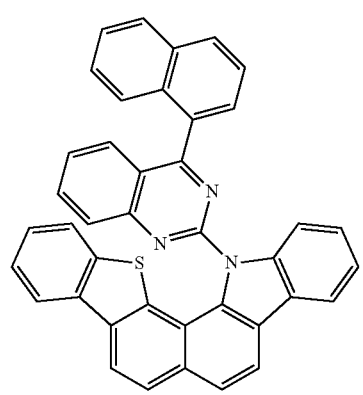
P-29
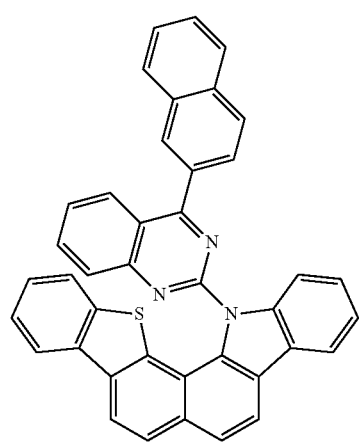
P-30
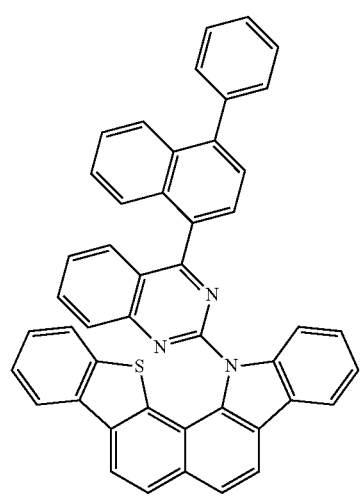

-continued
P-31
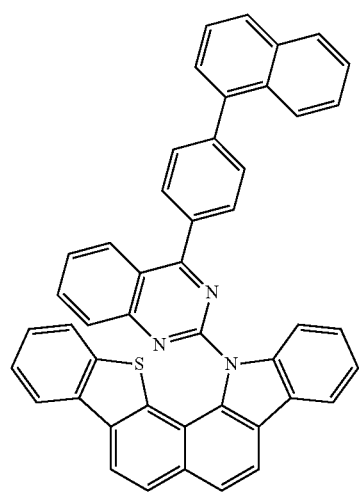
P-32
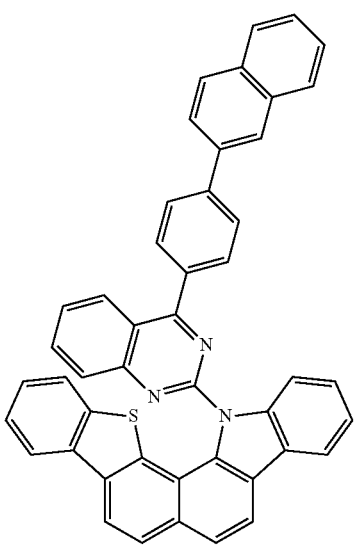
P-33
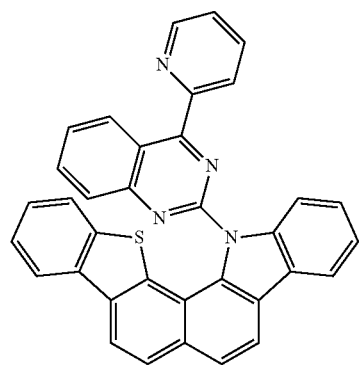
P-34
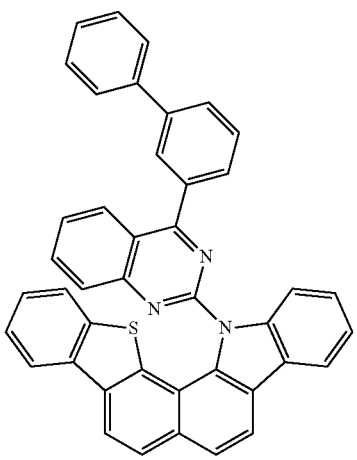
P-35
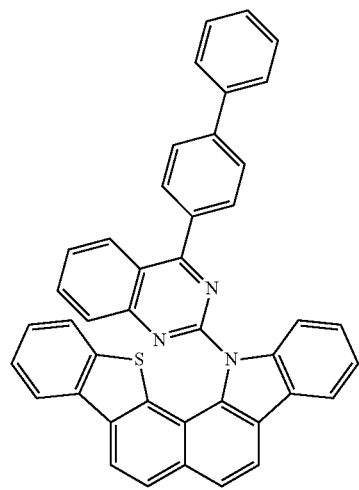
P-36
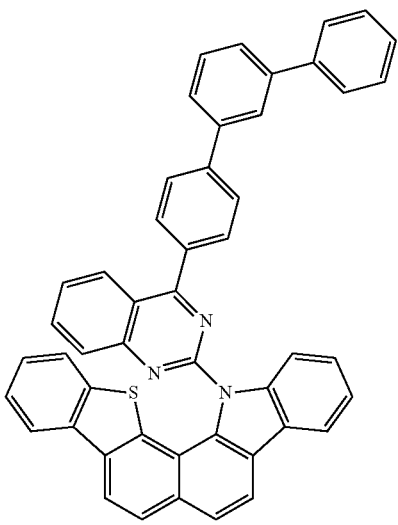

-continued
P-37
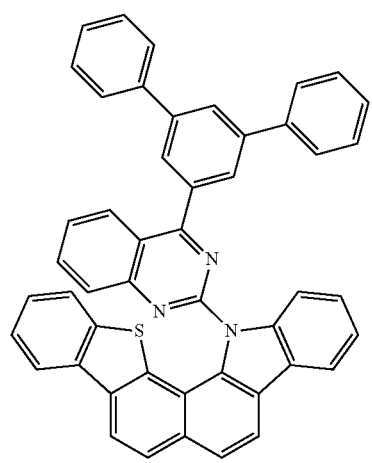
P-38
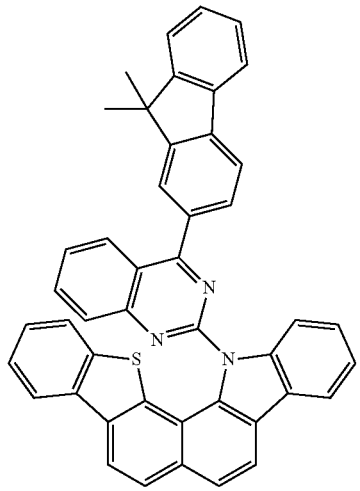
P-39
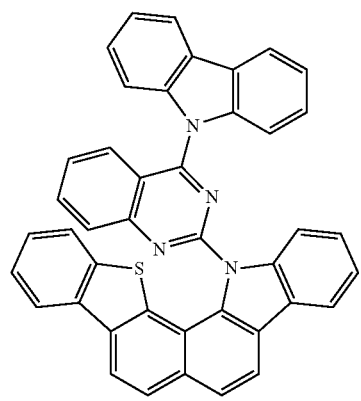
P-40
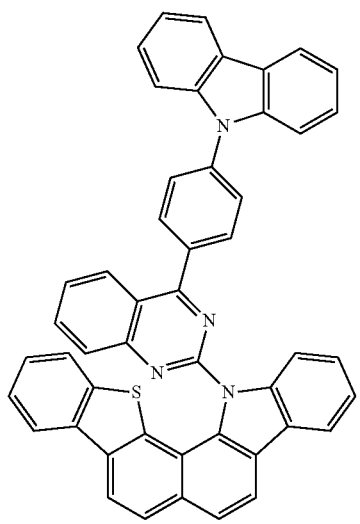
P-41
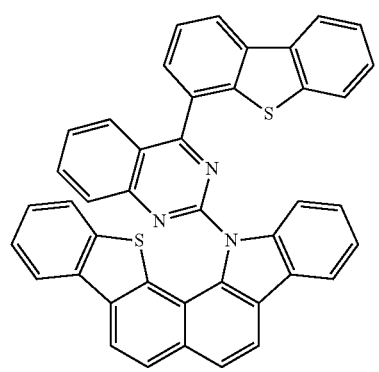
P-42
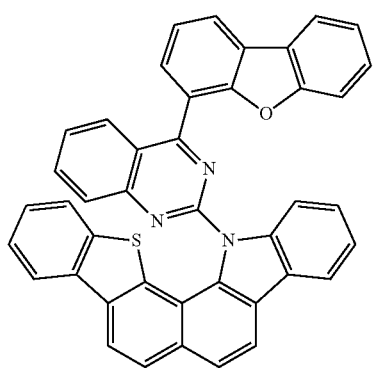

-continued
P-43
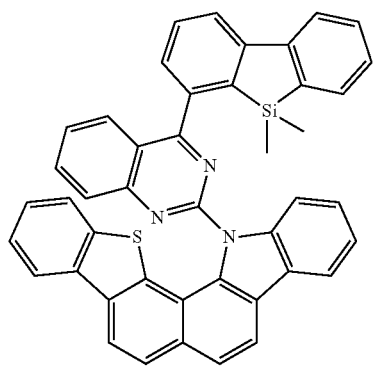
P-44
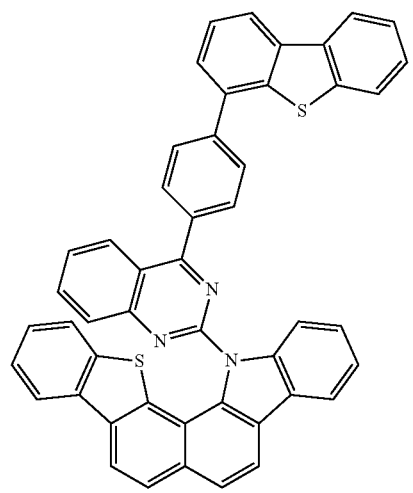
P-45
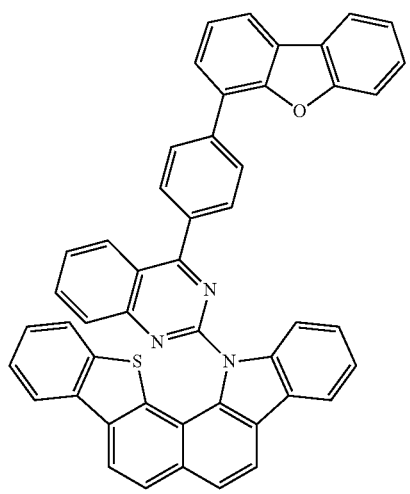
P-46
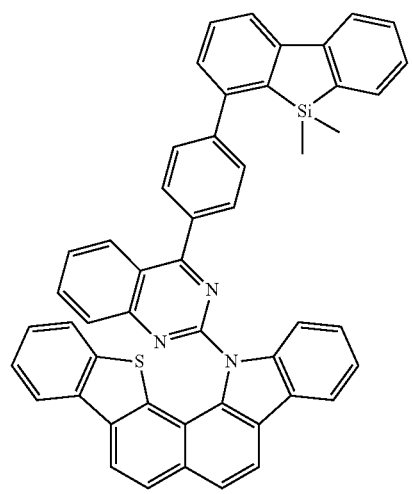
P-47
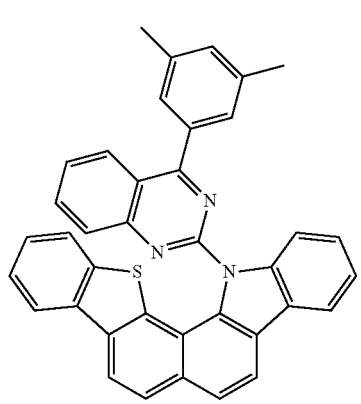
P-48
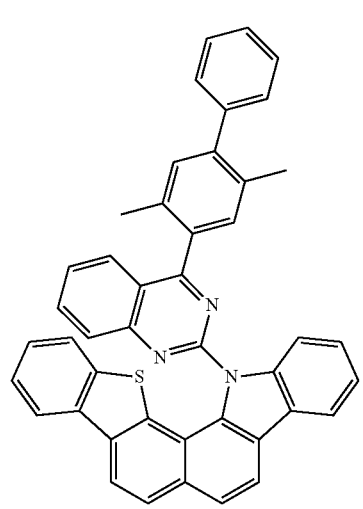

-continued
P-49
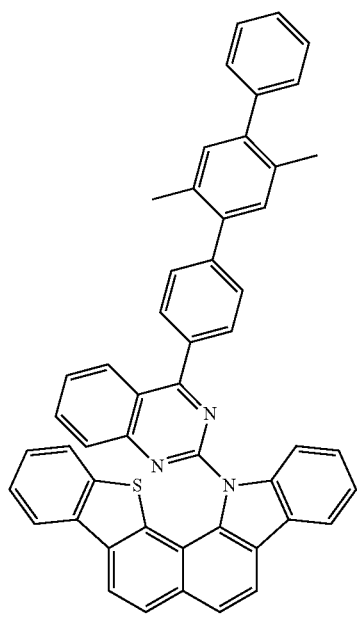
P-50
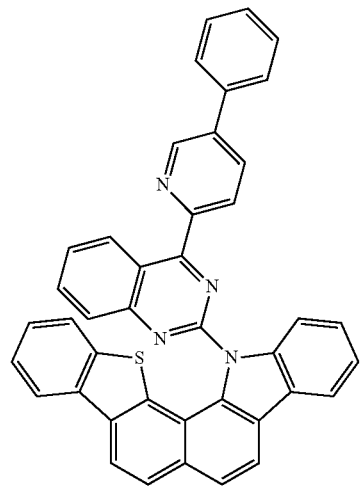
P-51
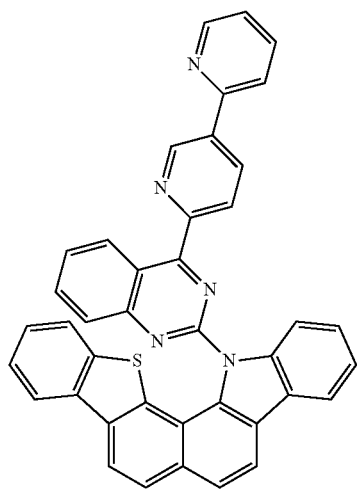
P-52
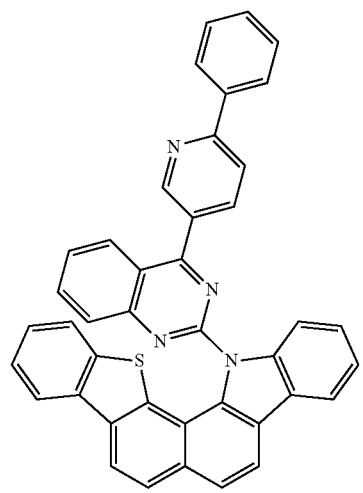
P-53
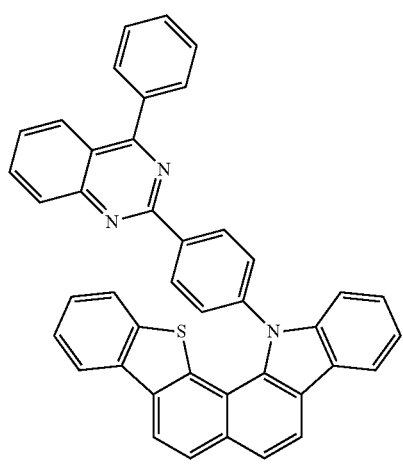
P-54
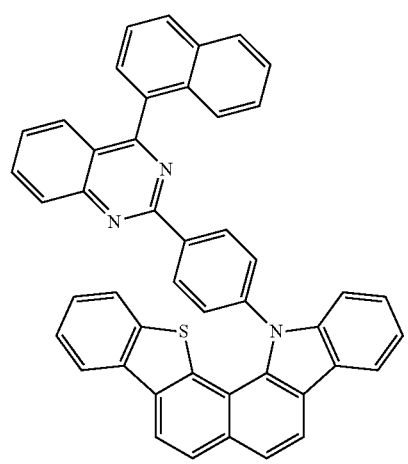

-continued
P-55
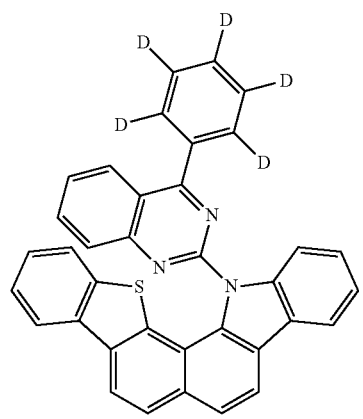
P-56
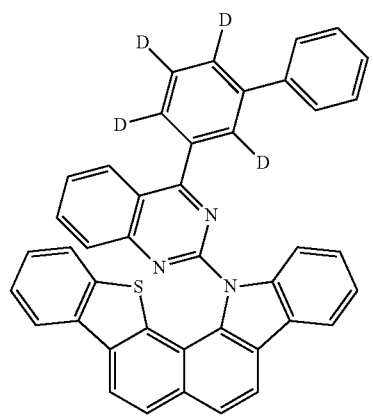
P-57
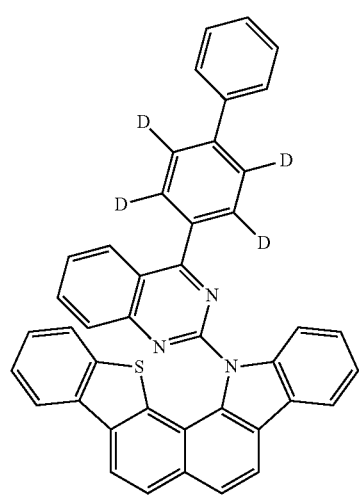
P-58
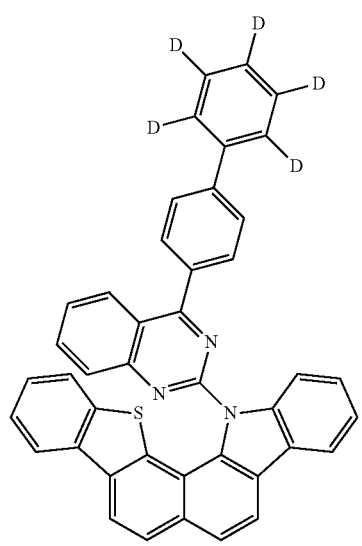
P-59
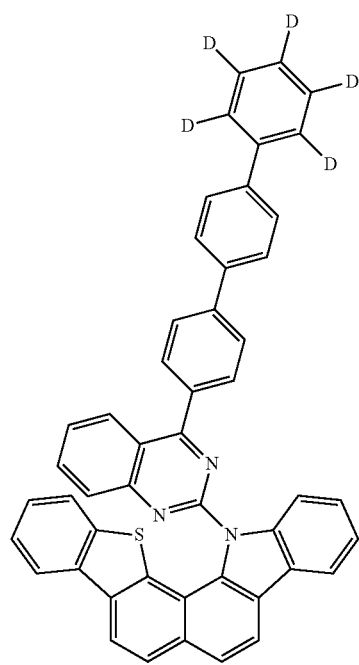
P-60
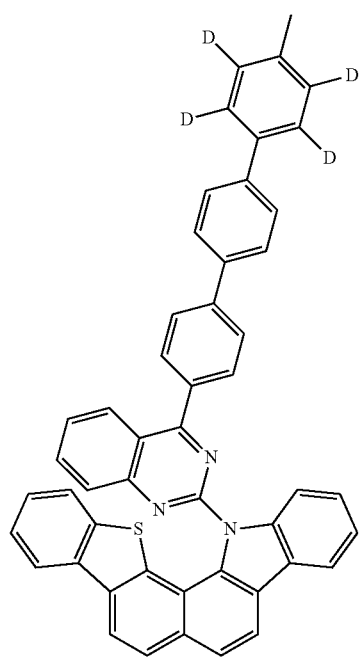

-continued
P-61
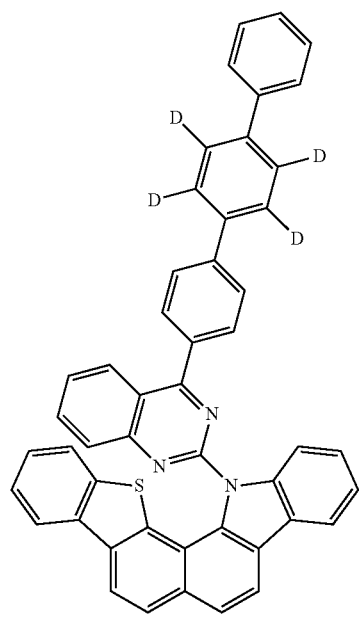
P-62
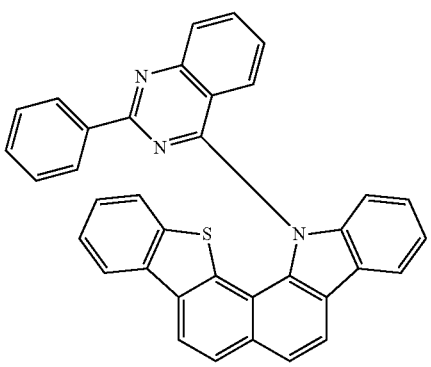
P-63
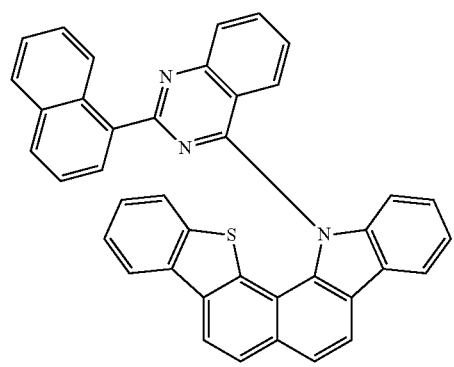
P-64
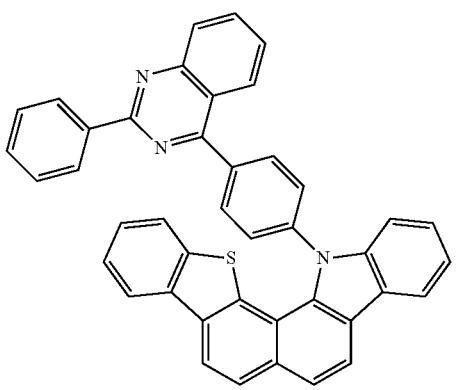
P-65
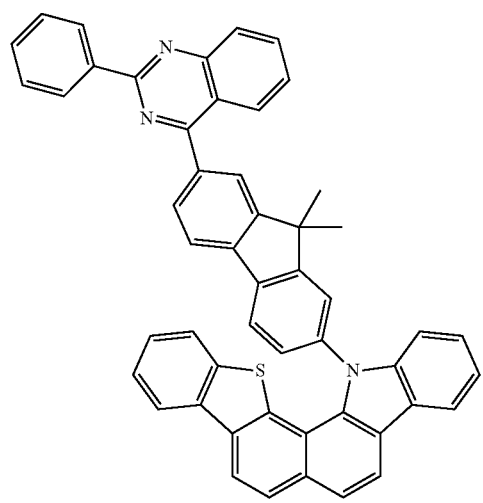
P-66
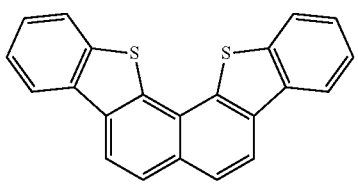

-continued
P-67
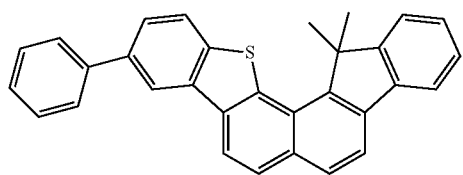
P-68
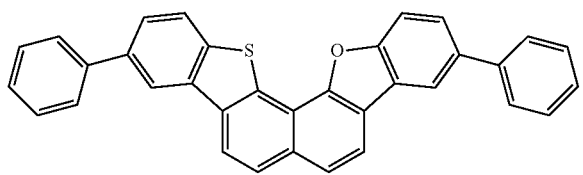
P-69
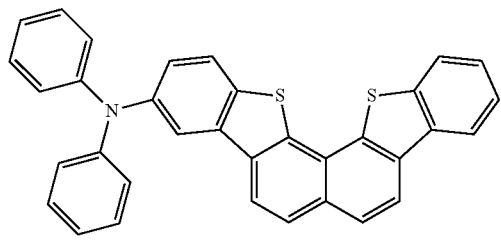
P-70
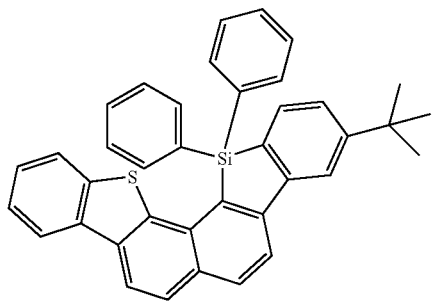
P-71
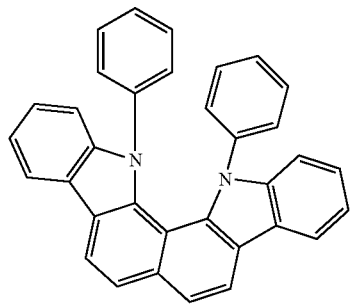
P-72
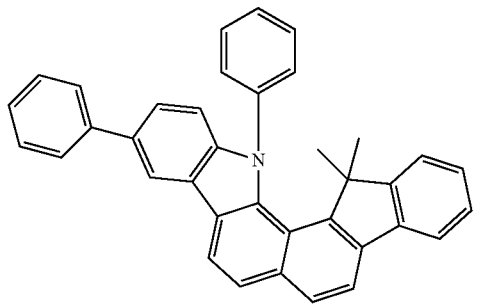
P-73
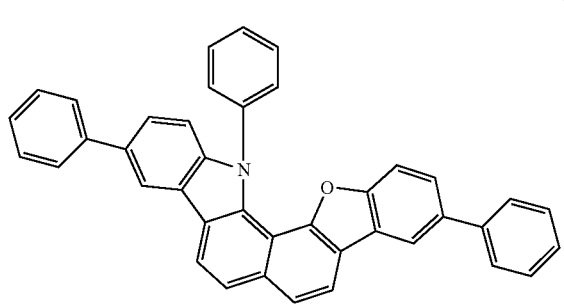
P-74
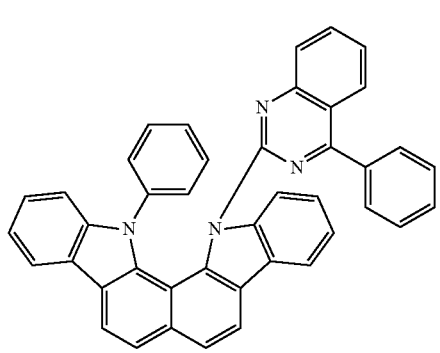
P-75
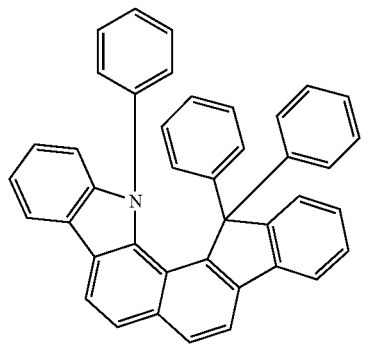
P-76
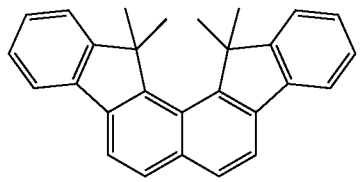

-continued
P-77
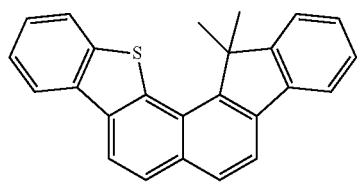
P-78
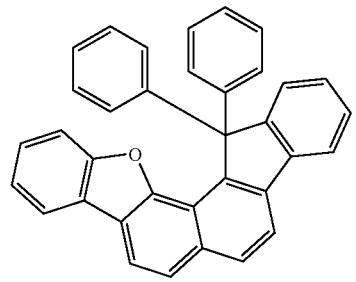
P-79
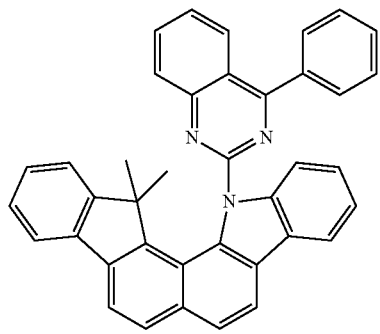
P-80
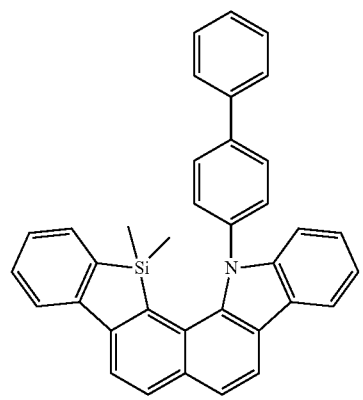
P-81
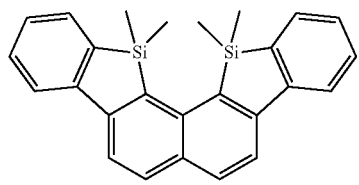
P-82
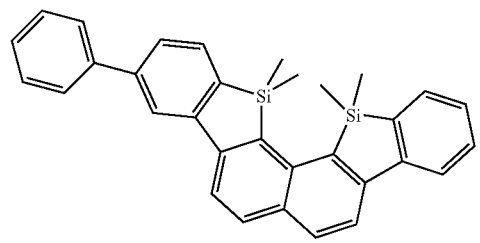
P-83
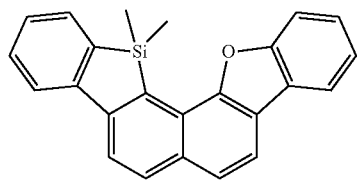
P-84
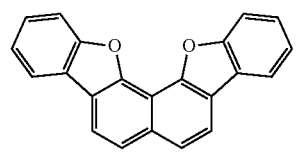
P-85
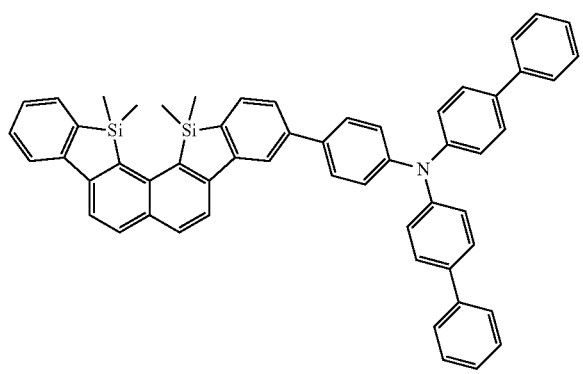
P-86

-continued
P-87
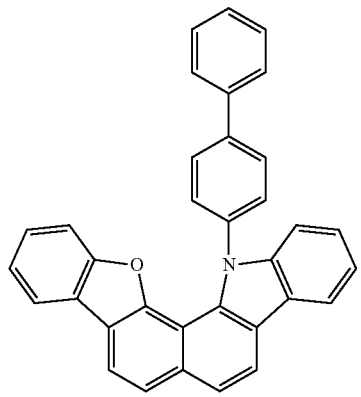
P-88
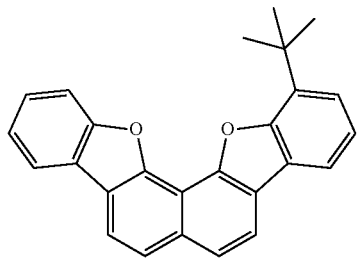
P-89
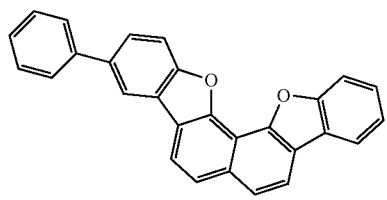
P-90
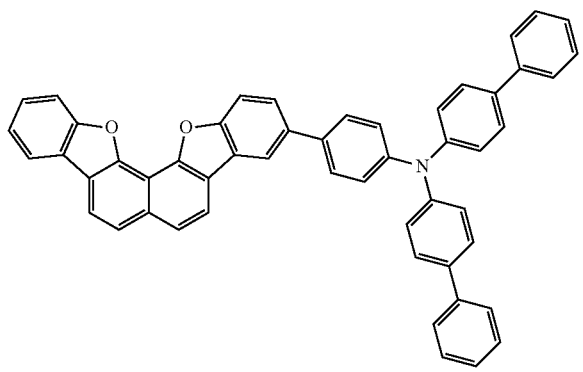
P-91
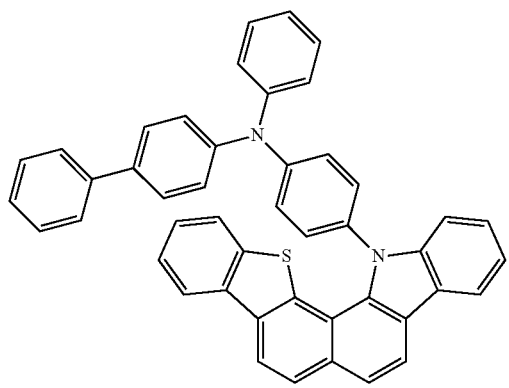
P-92
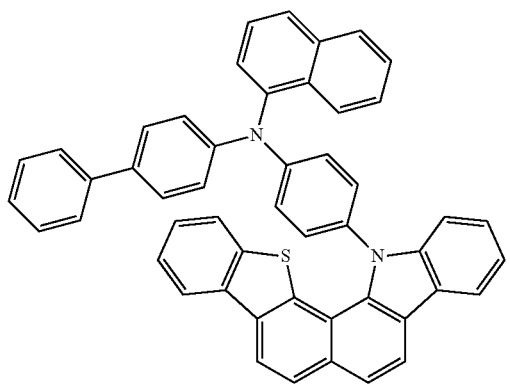
P-93
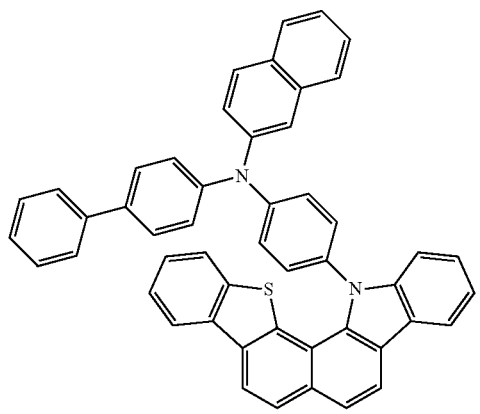
P-94
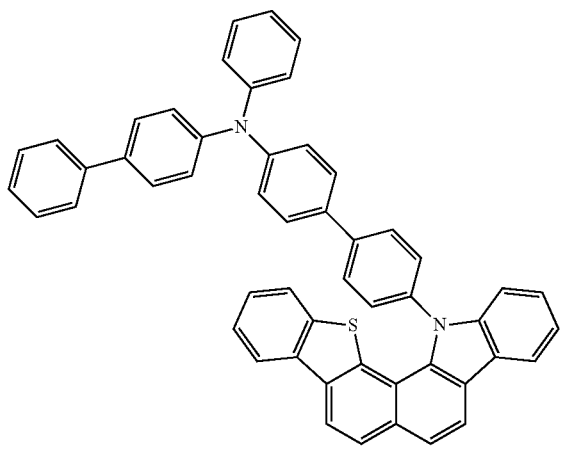

-continued
P-95
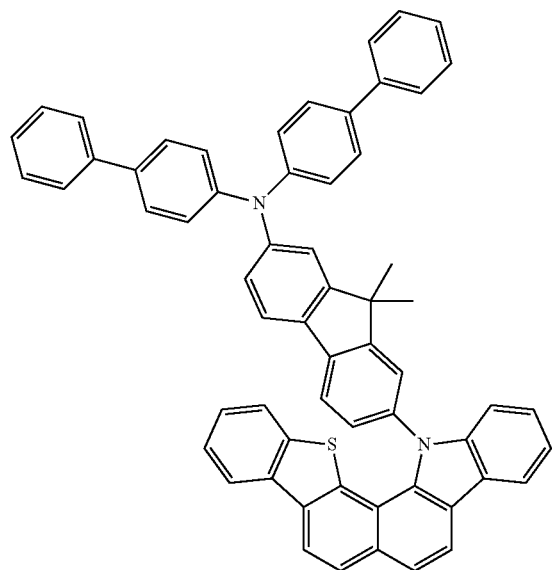
P-96
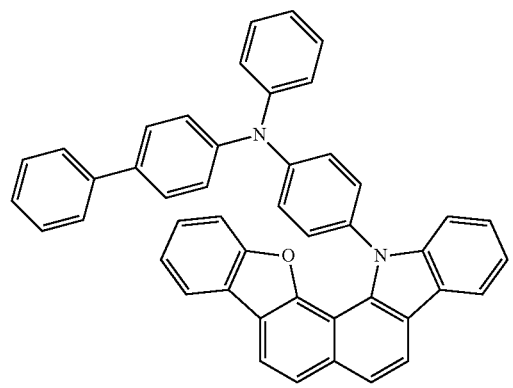
P-97
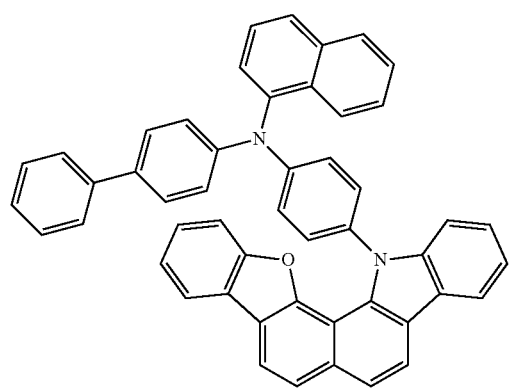
P-98
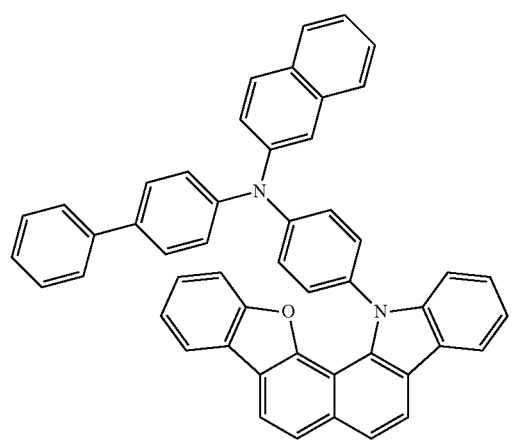
P-99
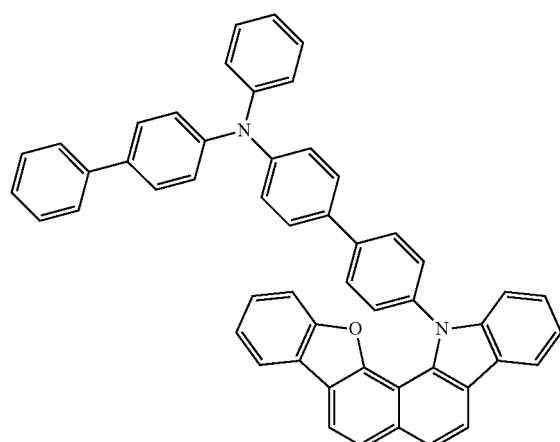
P-100
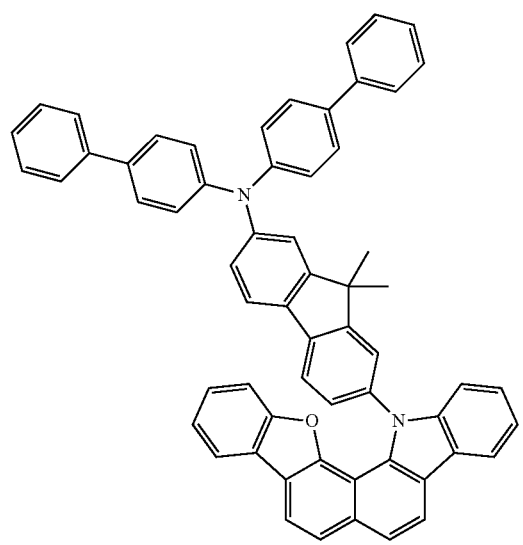

-continued
P-101
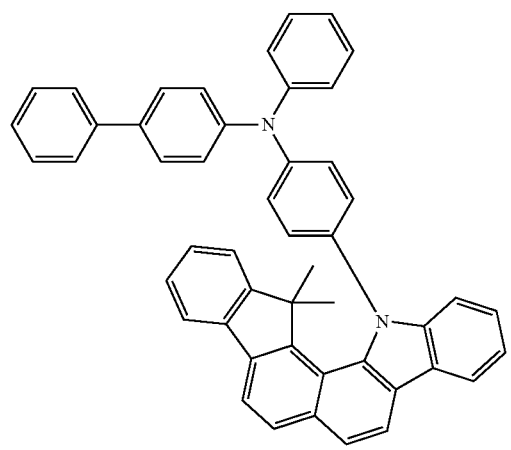
P-102
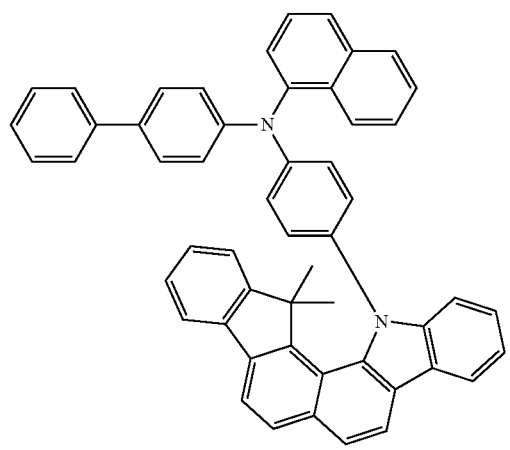
P-103
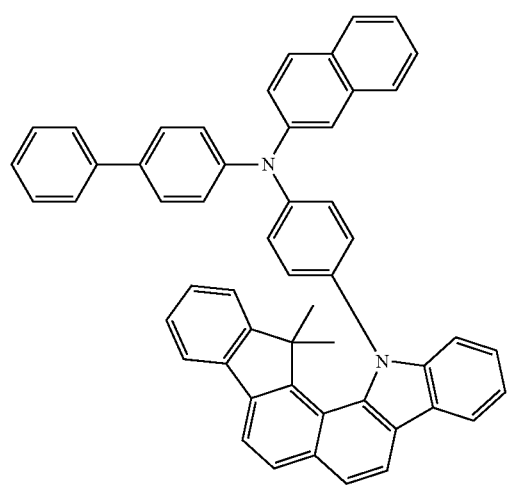
P-104
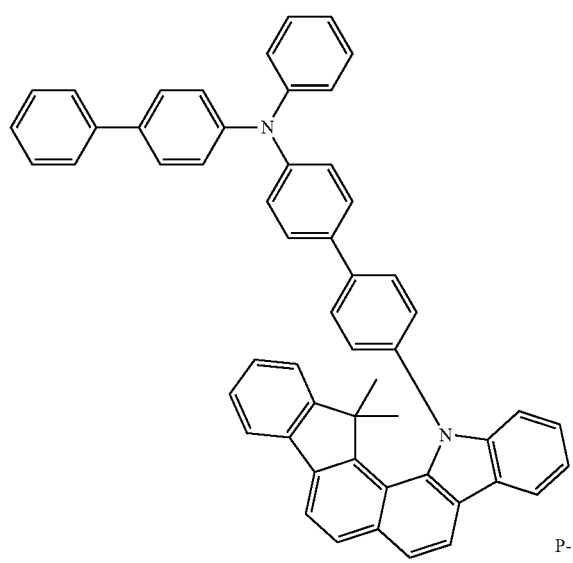
P-105
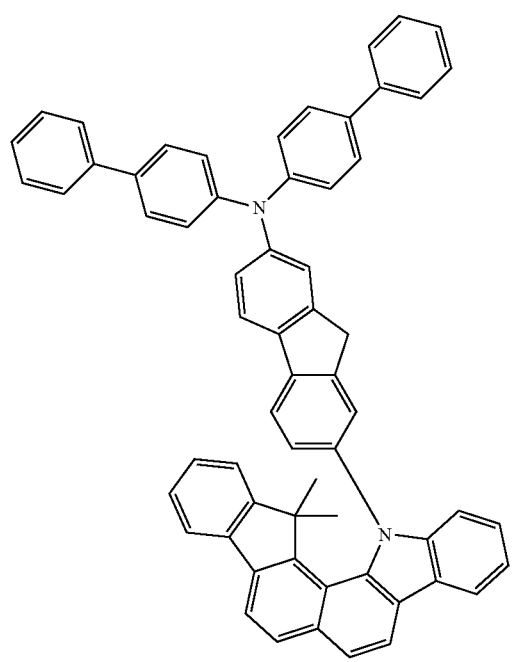
P-106
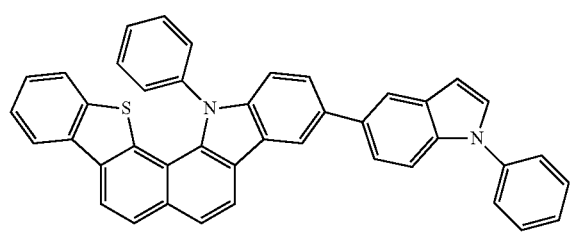

-continued
P-107
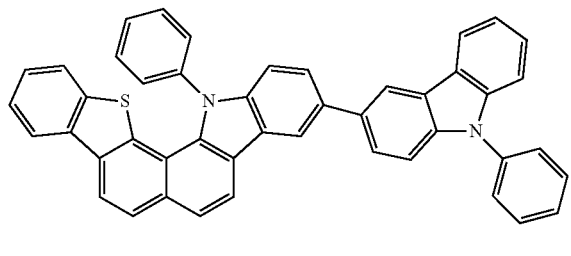
P-108
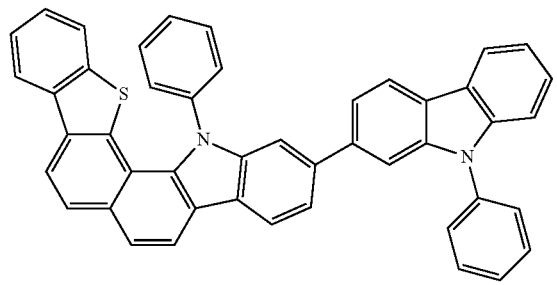
P-109
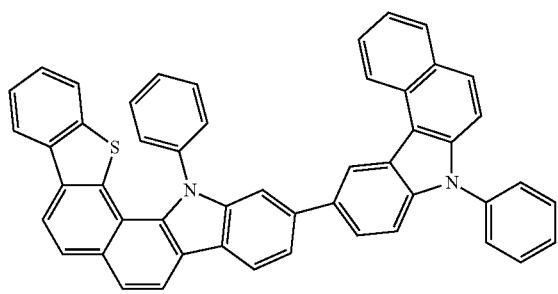
P-110
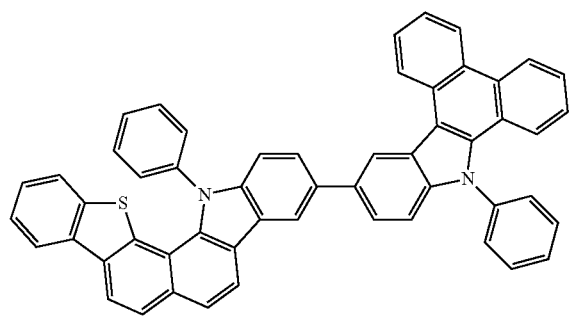
P-111
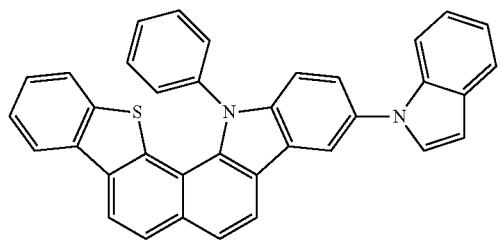
P-112
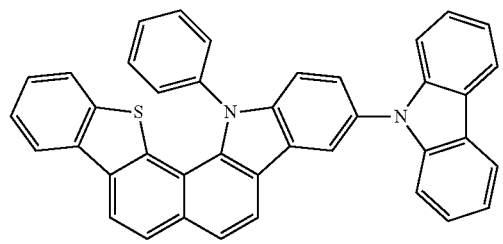
P-113
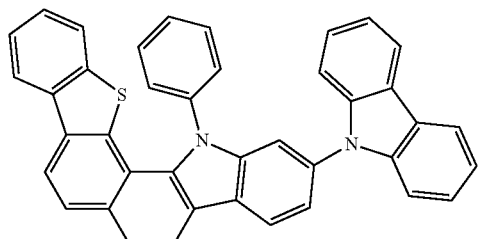
P-114
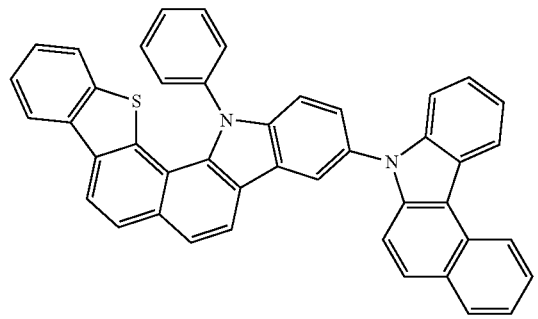
P-115
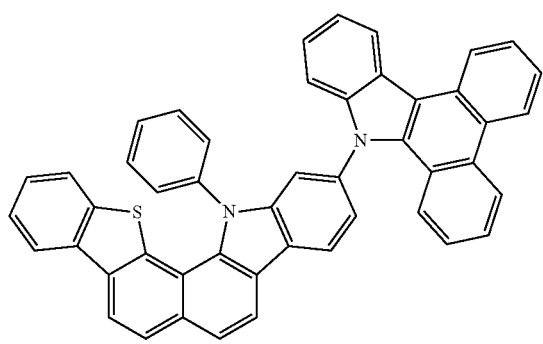
P-116
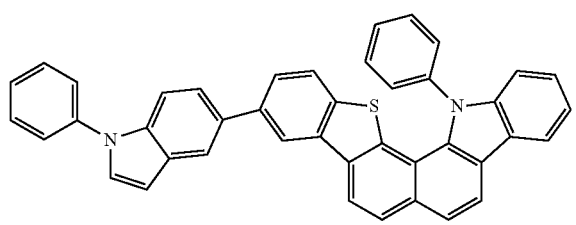

-continued
P-117
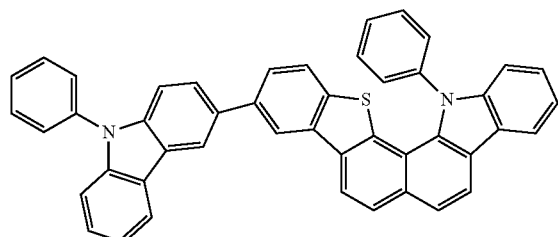
P-118
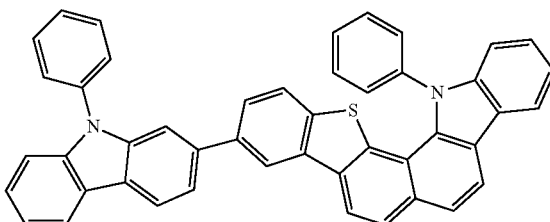
P-119
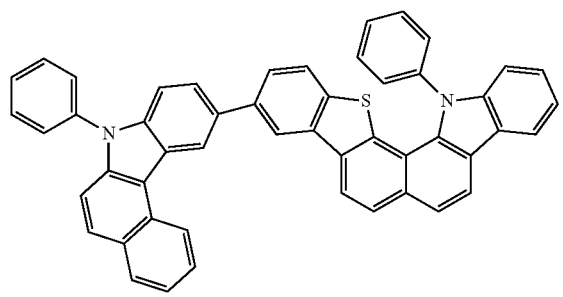
P-120
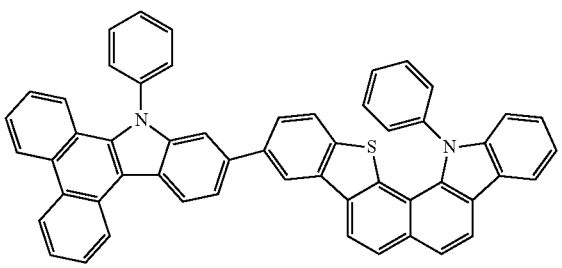
P-121
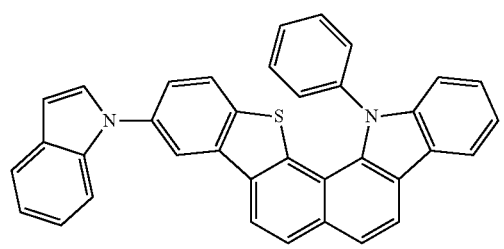
P-122
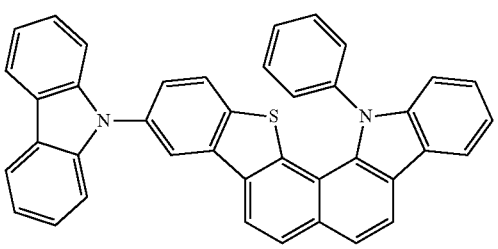
P-123
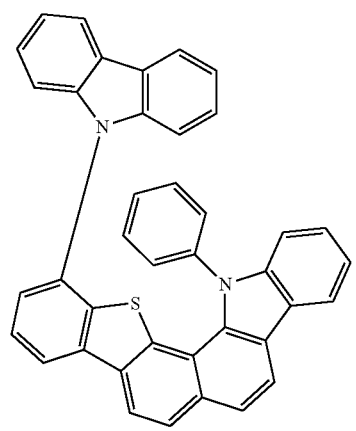
P-124
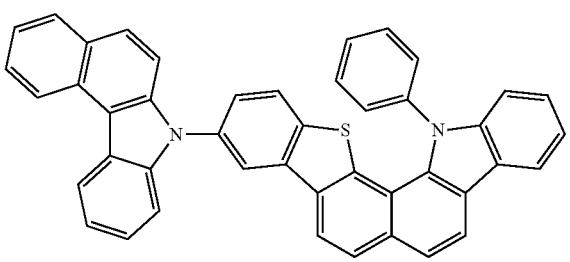
P-125
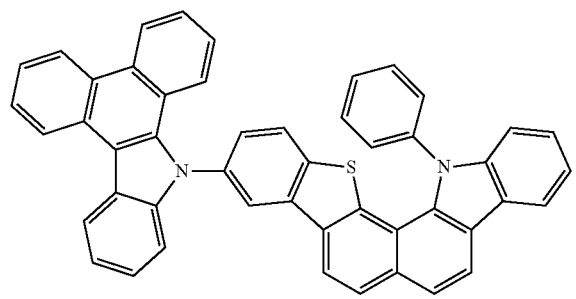
P-126
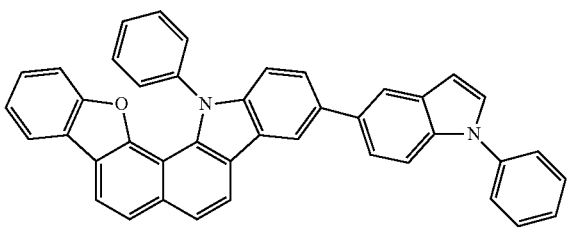

-continued
P-127
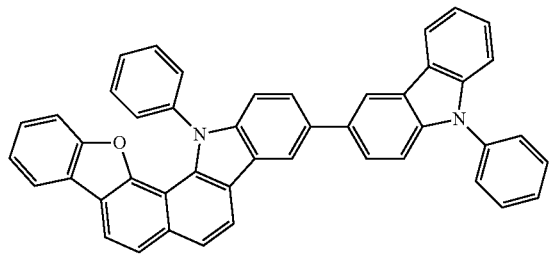
P-128
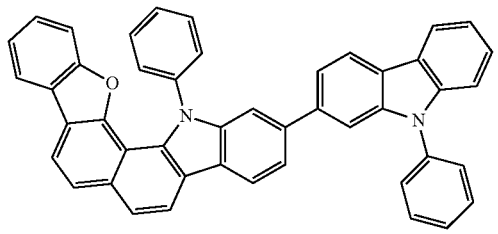
P-129
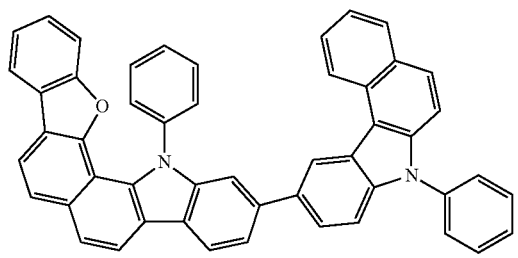
P-130
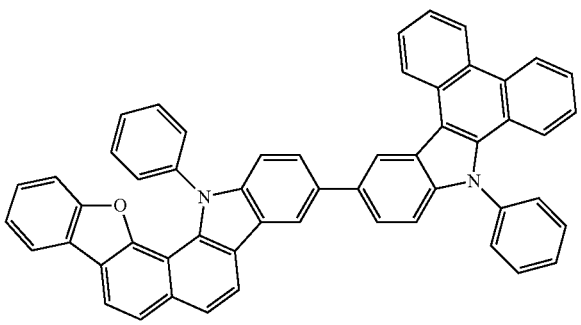
P-131
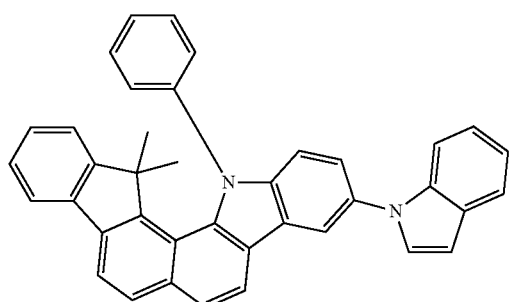
P-132
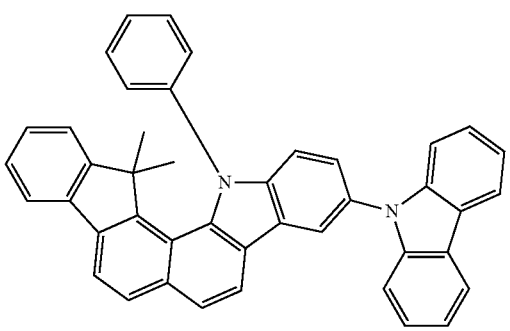
P-133
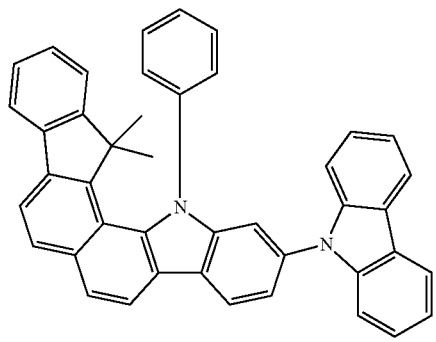
P-134
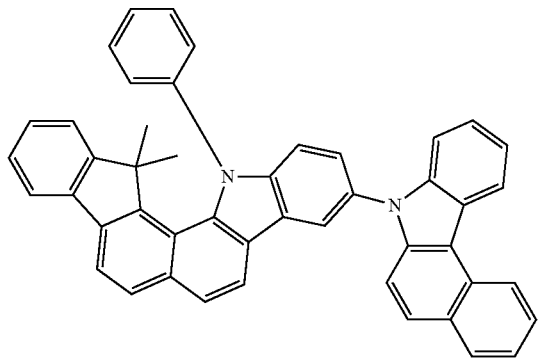
P-135
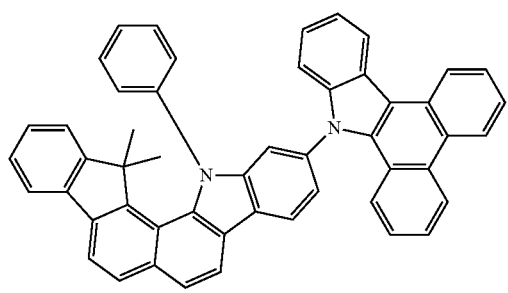
P-136
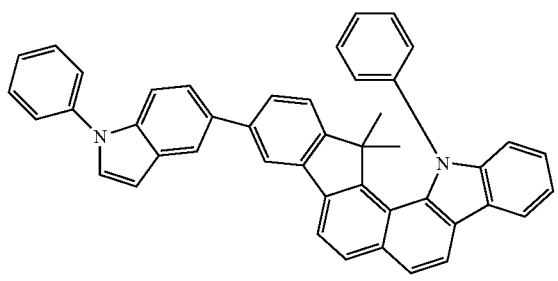

-continued
P-137
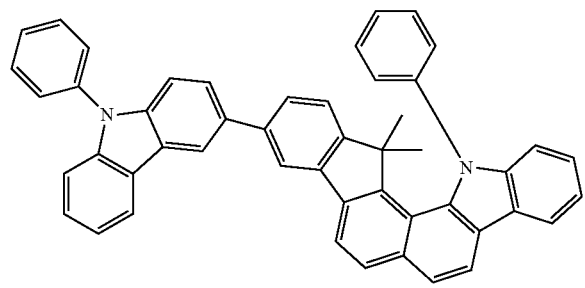
P-138
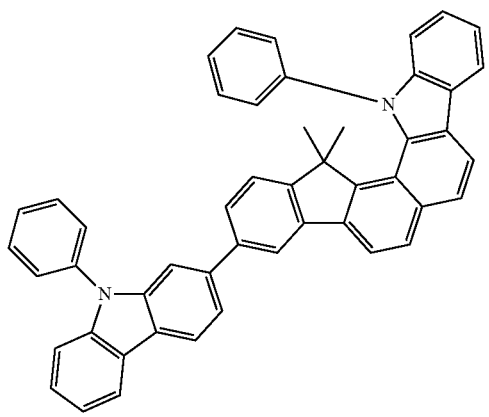
P-139
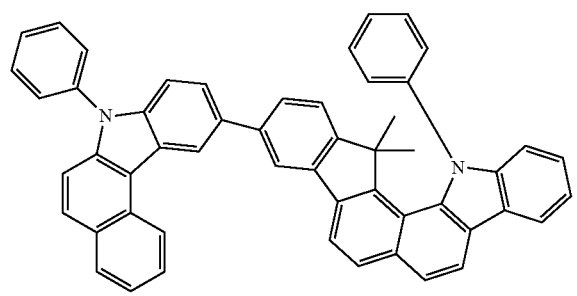
P-140
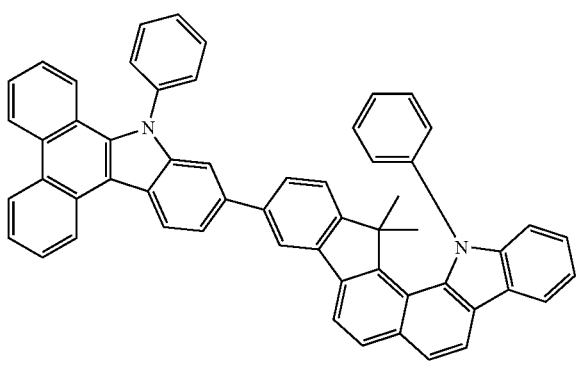
P-141
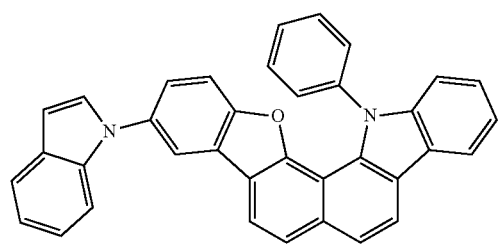
P-142
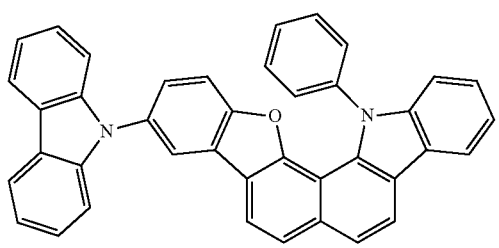
P-143
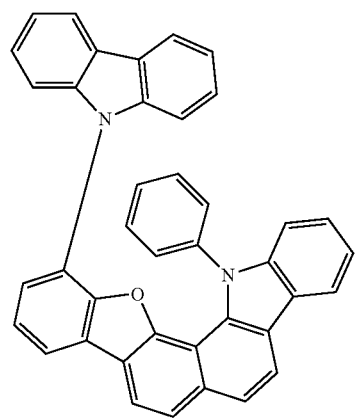
P-144
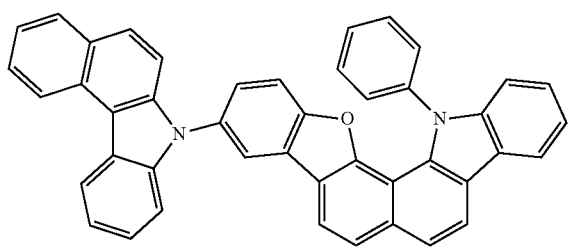

-continued
P-145
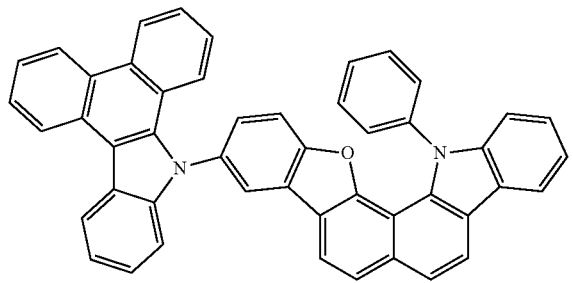
P-146
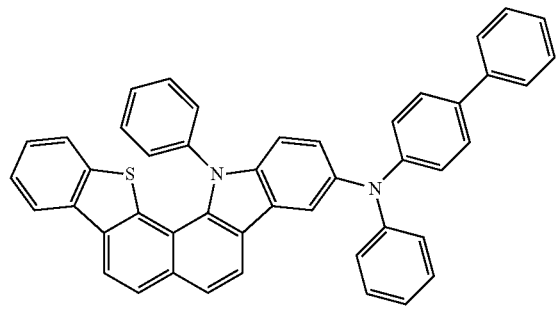
P-147
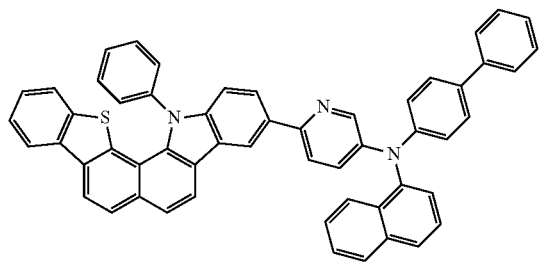
P-148
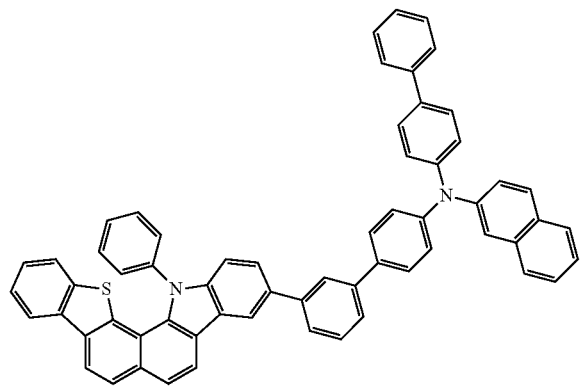
P-149
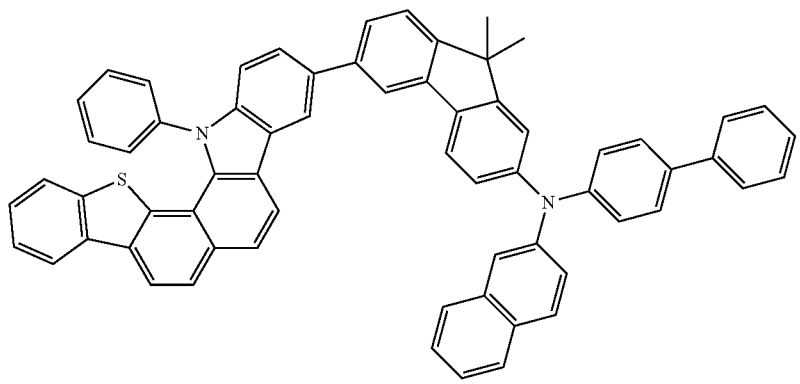
P-150
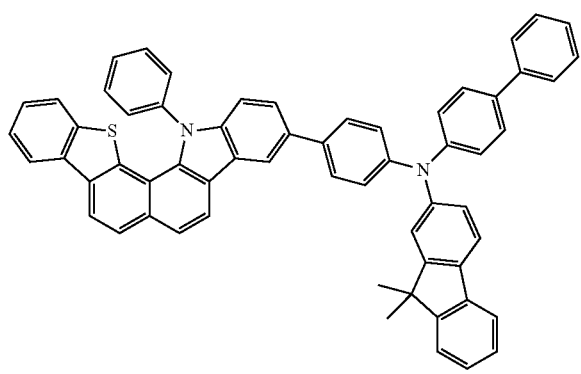
P-151
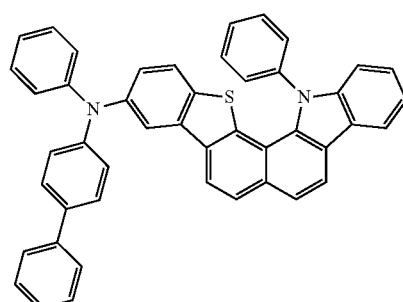

-continued
P-152
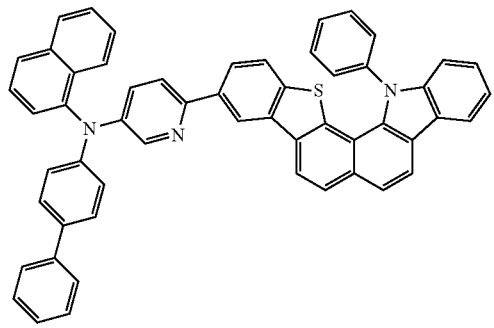
P-153
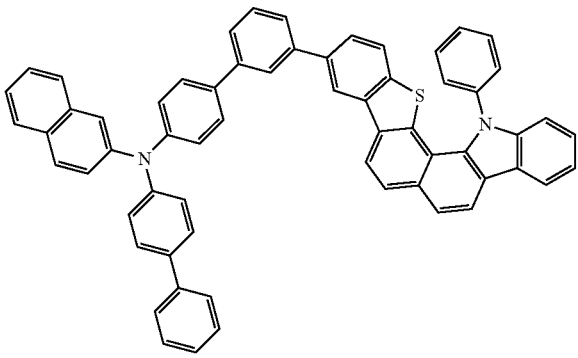
P-154
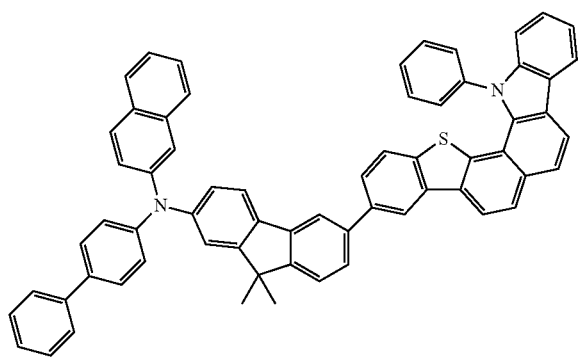
P-155
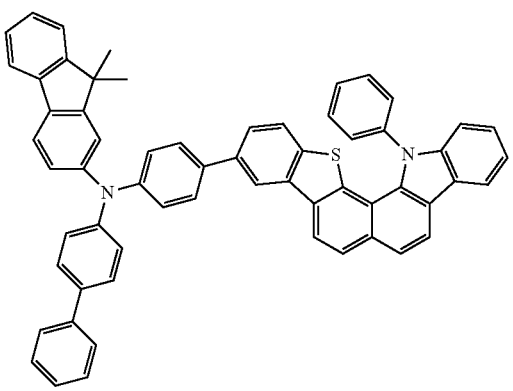
P-156
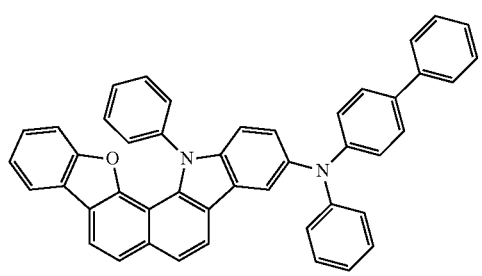
P-157
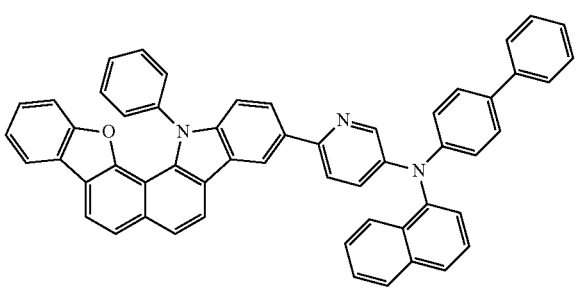
P-158
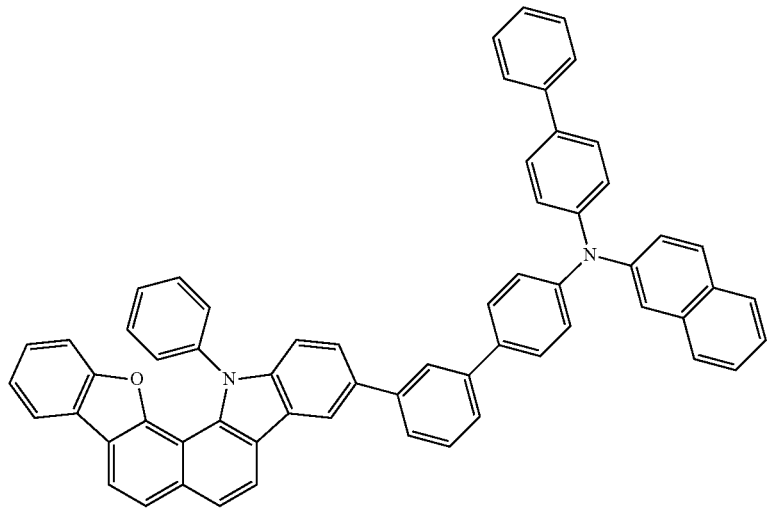

-continued
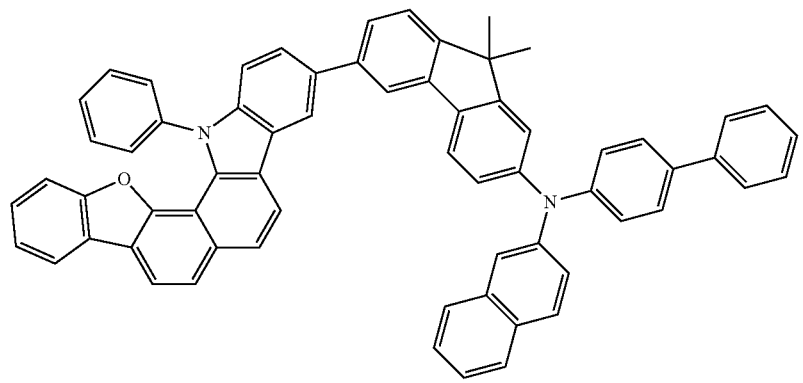
P-159
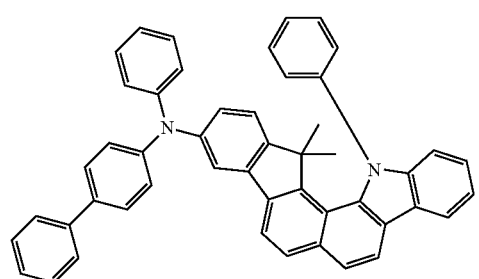
P-160
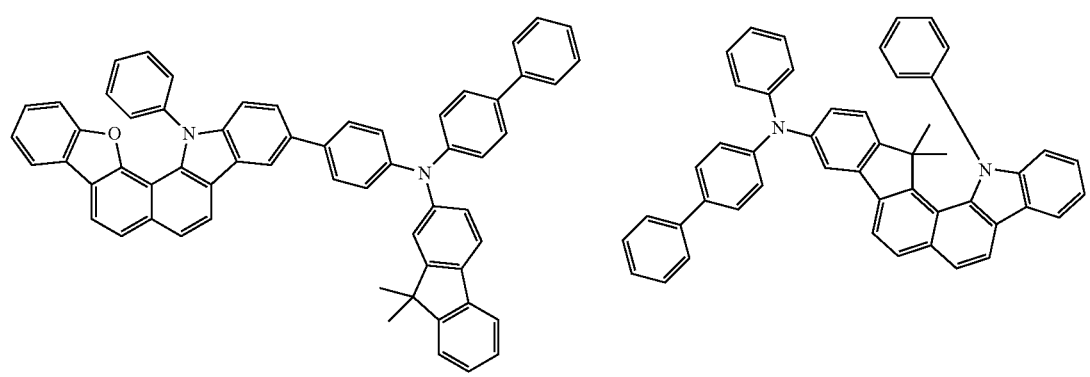
P-161
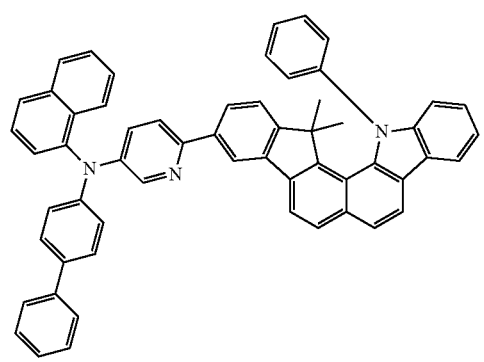
P-162
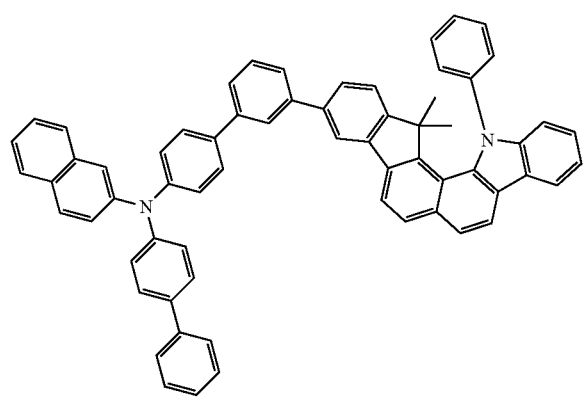
P-163
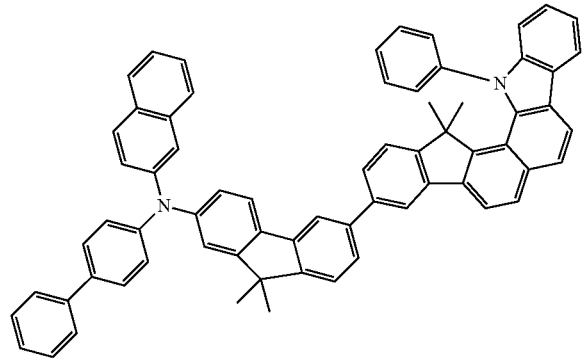
P-164
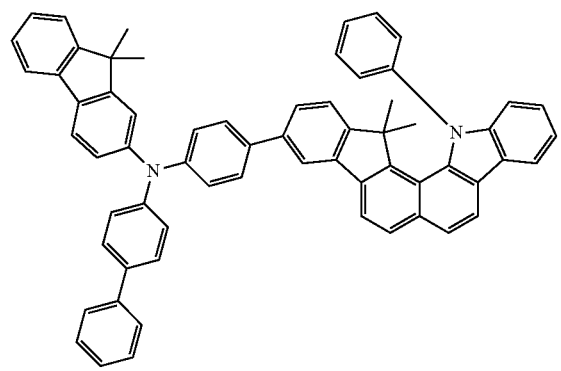
P-165
In another aspect of the present invention, there is provided an organic electric element comprising which can comprise a first electrode, a second electrode, and an organic material layer disposed between the first electrode and the second electrode, and the organic material layer comprises the compound represented by Formula 1 above. The compound by represented Formula 1 can be contained in at least one layer of a light emitting layer, a hole transport layer, and an emission-auxiliary layer of the organic material layer. That is, the compound represented by Formula 1 may be used as a material of a light emitting layer, a hole transport layer, or an emission-auxiliary layer.

Specially, there is provided the organic electric element comprising the organic material layer comprising at least one of the compounds represented by Formula 2 or Formula 3. More specially, there is provided and the organic electric element comprising the organic material layer comprising at least one of the compounds represented by the individual formulas above.

Hereinafter, Synthesis Examples of the inventive compound represented by Formula according to the present invention and Preparation Examples of an organic electric element will be described in detail by way of example. However, the following examples are only for illustrative purposes and are not intended to limit the scope of the invention.

SYNTHESIS EXAMPLE

The final product according to the present invention can be synthesized by reaction between Sub 1 and Sub 2 as illustrated in, but not limited to, the following Reaction Scheme 1.

<Reaction Scheme 1>

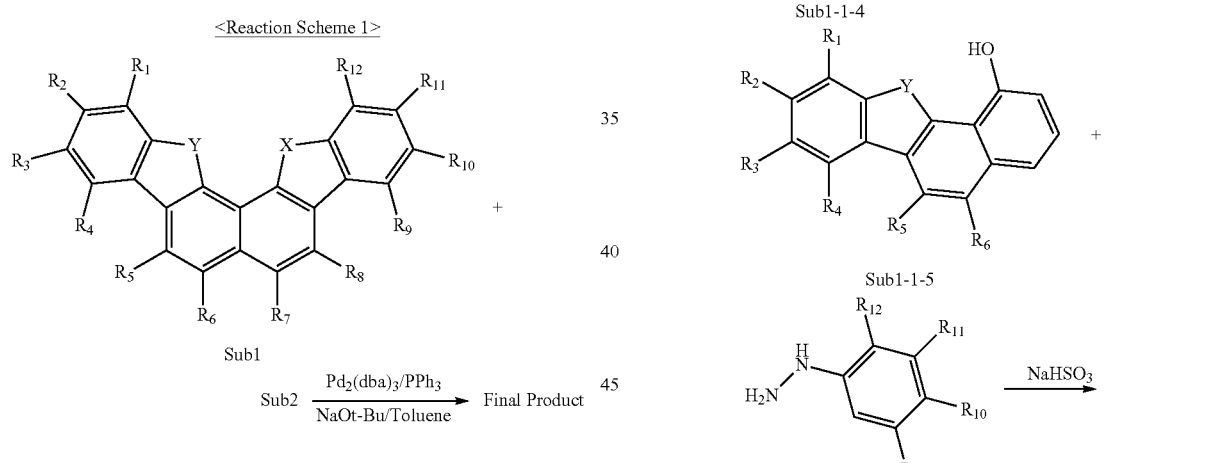

I. Synthesis Method of Sub 1
Sub 1 of Reaction Scheme 1 can be synthesized according to, but not limited to, the following Reaction Scheme 2.
1. Synthesis Method of Sub 1-1

<Reaction Scheme 2>

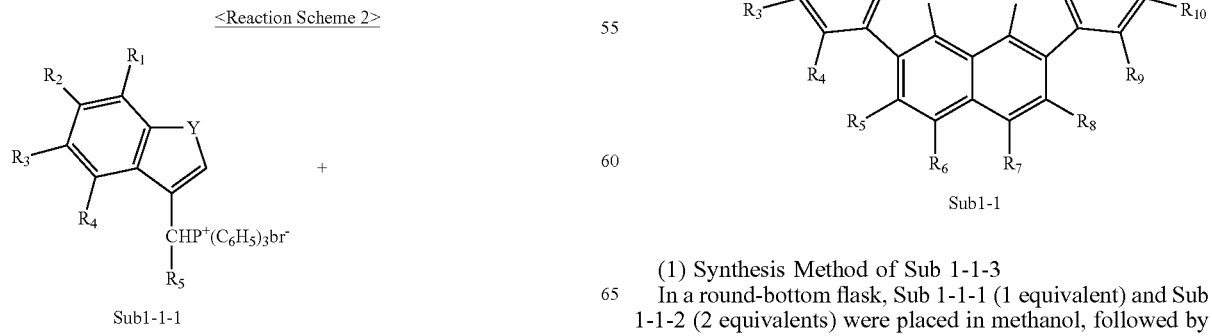

Sub1-1-1

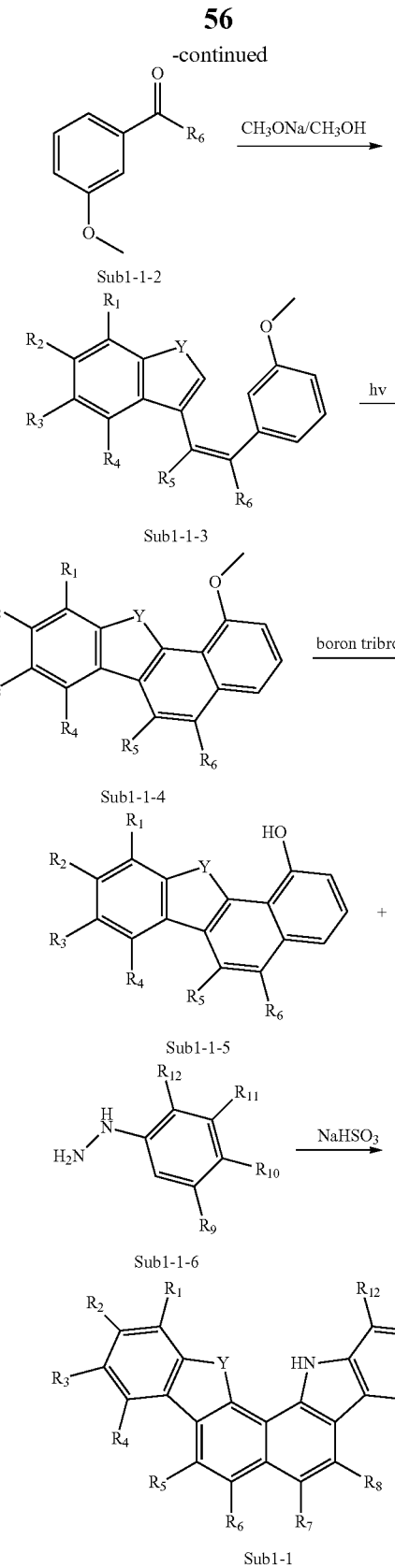

(1) Synthesis Method of Sub 1-1-3
In a round-bottom flask, Sub 1-1-1 (1 equivalent) and Sub 1-1-2 (2 equivalents) were placed in methanol, followed by stirring. Sodium methoxide was placed in the solution, followed by stirring at room temperature for 24 hrs. Upon completion of the reaction, the reaction product was extracted with dichrolomethane and water. The extracted organic layer was dried and concentrated, and then the produced organic material was separated by a silica gel column and recrystallized to obtain Sub 1-1-3.

(2) Synthesis Method of Sub 1-1-4

In a round-bottom flask, Sub 1-1-3 (1 equivalent), and iodine were placed in dry benzene, followed by being subjected to UV treatment with a UV lamp during the generation of bubbles from the solution, and the progression was monitored by TLC. After seven hours, the solvent was removed in a vacuum, followed by recrystallizing with ethanol to obtain Sub 1-1-4.

(3) Synthesis Method of Sub 1-1-5

Sub 1-1-4 (1 equivalent) and boron tribromide were placed in dichrolomethane, followed by stirring at room temperature for 12 hrs. Upon completion of the reaction, the reaction product was extracted with ether and water. The extracted organic layer was dried with $MgSO_4$ and concentrated, and then the produced organic material was separated by a silica gel column and recrystallized to obtain Sub 1-1-5.

(4) Synthesis Method of Sub 1-1

Sub 1-1-5 (1 equivalent), Sub 1-1-6 (3 equivalents) and $NaHSO_3$ (5 equivalents) were placed in distilled water, followed by stirring and refluxing at 100° C. for 15 hrs. Subsequently, a refluxed reactant was cooled, followed by adding distilled water. The produced solid was subjected to vacuum-filtration, and the obtained solid was placed in aqueous solution of HCl, followed by heating to 100° C. Upon completion of the reaction, the reaction product was extracted with a methylchloride for 1 hour, and washed with distilled water and aqueous solution of NaOH. And then the produced organic material was separated by a silica gel column and recrystallized to obtain Sub 1-1.

Meanwhile, examples of Sub 1-1 compounds include, but are not limited to, the following compounds, and Field Desorption Mass Spectrometry (FD-MS) data of the compounds are given in Table 1 below:

Sub1-1-A

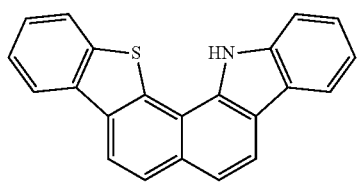

Sub1-1-B

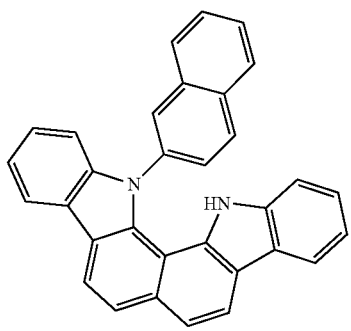

Sub1-1-C

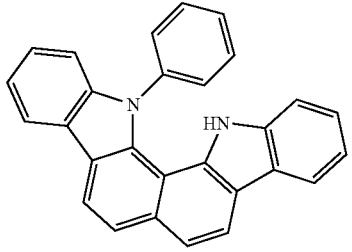

Sub1-1-D

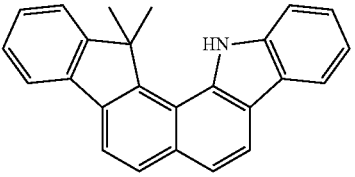

Sub1-1-E

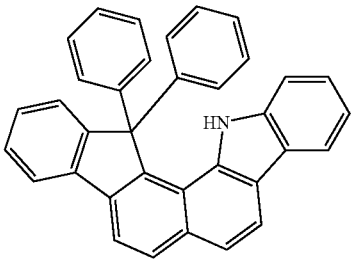

Sub1-1-F

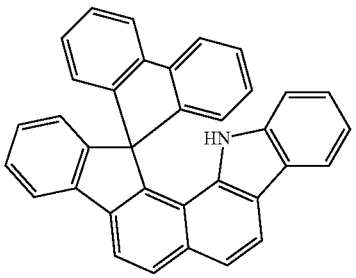

Sub1-1-G

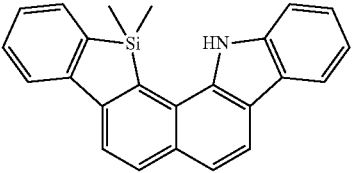

Sub1-1-H

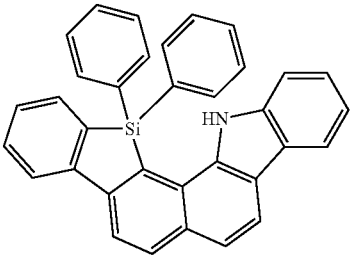

Sub1-1-I
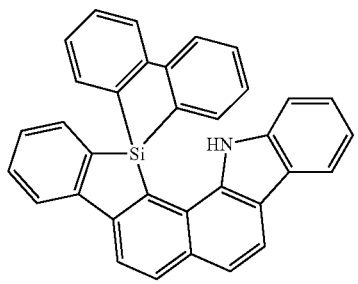
Sub1-1-L
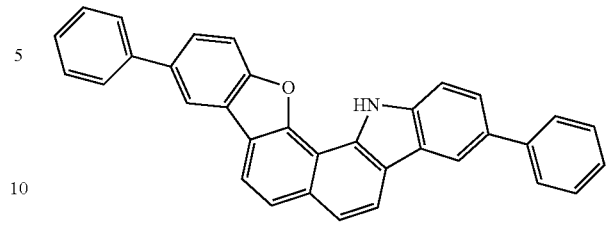
Sub1-1-J
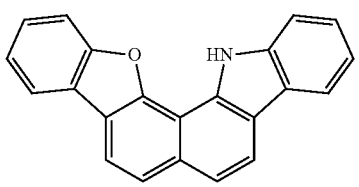
Sub1-1-M
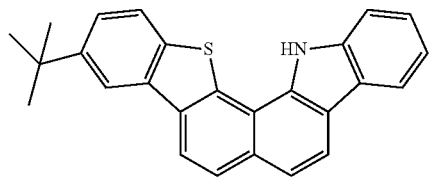
Sub1-1-K
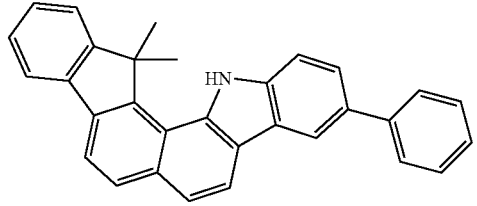
Sub1-1-N
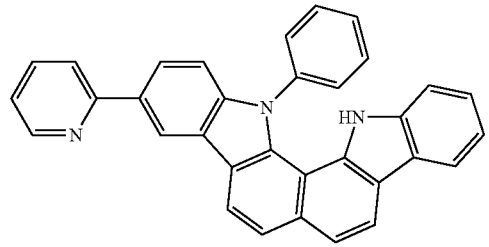
TABLE 1
| Compound | FD-MS | Compound | FD-MS |
| --- | --- | --- | --- |
| Sub 1-1-A | m/z = 323.08($C_{22}H_{13}NS$ = 323.41) | Sub 1-1-B | m/z = 432.16($C_{32}H_{20}N_2$ = 432.51) |
| Sub 1-1-C | m/z = 382.15($C_{28}H_{18}N_2$ = 382.46) | Sub 1-1-D | m/z = 333.15($C_{25}H_{19}N$ = 333.43) |
| Sub 1-1-E | m/z = 457.18($C_{35}H_{23}N$ = 457.56) | Sub 1-1-F | m/z = 455.17($C_{35}H_{21}N$ = 455.55) |
| Sub 1-1-G | m/z = 349.13($C_{24}H_{19}NSi$ = 349.50) | Sub 1-1-H | m/z = 473.16($C_{34}H_{23}NSi$ = 473.64) |
| Sub 1-1-I | m/z = 471.14($C_{34}H_{21}NSi$ = 471.62) | Sub 1-1-J | m/z = 307.10($C_{22}H_{13}NO$ = 307.34) |
| Sub 1-1-K | m/z = 409.18($C_{31}H_{23}N$ = 409.52) | Sub 1-1-L | m/z = 459.16($C_{34}H_{21}NO$ = 459.54) |
| Sub 1-1-M | m/z = 379.14($C_{26}H_{21}NS$ = 379.52) | Sub 1-1-N | m/z = 459.17($C_{33}H_{21}N_3$ = 459.54) |

2. Synthesis Method of Sub 1-2

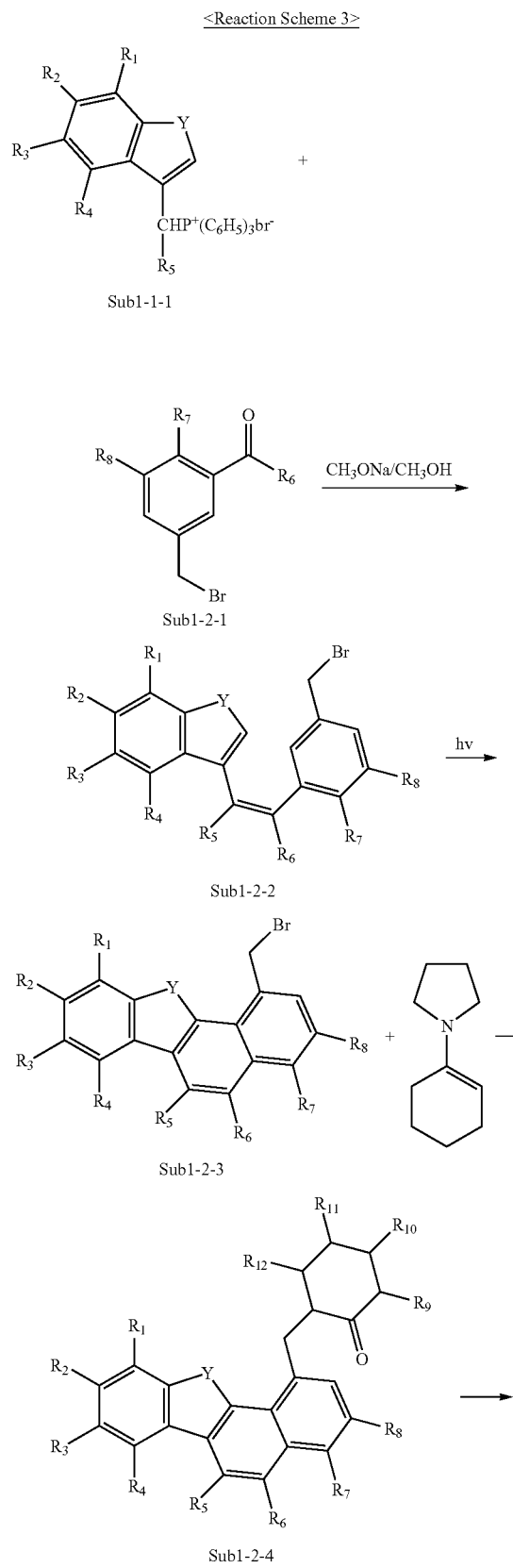

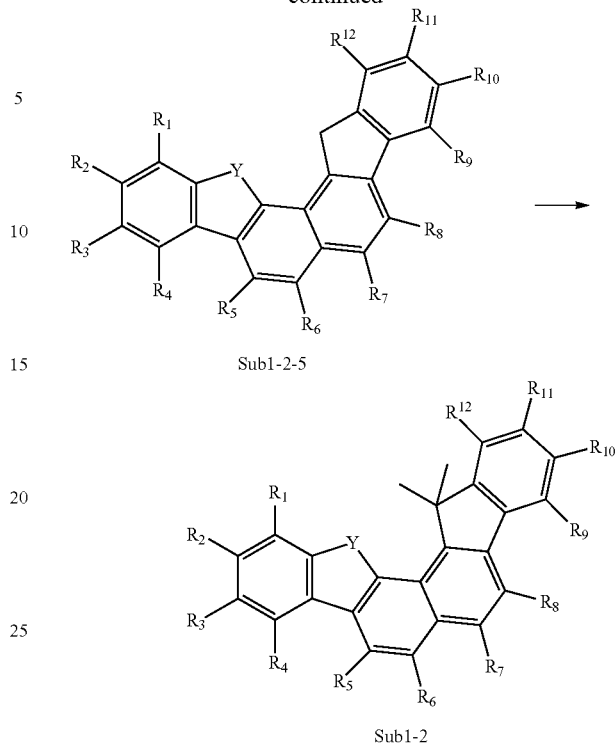

(1) Synthesis Method of Sub 1-2-2

In a round-bottom flask, Sub 1-1-1 (1 equivalent) and Sub 1-2-1 (1 equivalent) were placed in methanol followed by stirring. Sodium methoxide was placed in the solution, followed by stirring at room temperature for 24 hours. Upon completion of the reaction, the reaction product was extracted with a dichrolomethane and water. The extracted organic layer was dried and concentrated, and then the produced organic material was separated by a silica gel column and recrystallized to obtain Sub 1-2-2.

(2) Synthesis Method of Sub 1-2-3

In a round-bottom flask, Sub 1-2-2 (1 equivalent), and iodine were placed in dry benzene, followed by being subjected to UV treatment with a UV lamp during the generation of bubbles from the solution, and the progression was monitored by TLC. After seven hours, the solvent was removed in a vacuum, followed by recrystallizing with ethanol to obtain Sub 1-2-3.

(3) Synthesis Method of Sub 1-2-4

To a solution of Sub 1-2-3 (1 equivalent) in dioxane was added 1-pyrrolidino-1-cyclohexane (1.1 equivalent), followed by refluxing for 18 hours. The refluxed reactant was added with water and heated for 2 hours, followed by being treated with ether and a solution containing 5% HCl and 5% $NaHCO_3$ for work-up. Upon completion of work-up, the produced organic material was separated by a silica gel column and recrystallized to obtain Sub 1-2-4.

(4) Synthesis Method of Sub 1-2-5

Sub 1-2-4 was dissolved with 70 ml of a mixture of $CHCl_3$ and 10% of a methanesulfonic acid, followed by stirring at room temperature for 2 hours. After the reaction was terminated with a bicarbonate solution, the reaction mixture was treated with methylene chloride, $NaHCO_3$ and water for a work-up procedure. Subsequently, the solvent was evaporated, followed by being separated by column chromatography. The Separated product was dissolved, together with 10% Pd/C, in triglyme, followed by being refluxed for 16 hours. And then, the refluxed product was treated with Column chromatography using hexane to obtain Sub 1-2-5.

(5) Synthesis Method of Sub 1-2

A solution of Sub 1-2-5 (1 equivalent) in tetrahydrofuran was quenched to −78□, and n-BULi (1.1 equivalents (1.6M in hexane)) was slowly added to the solution. Upon completion of the reaction for 1 hour, iodine methane (1.3 equivalents) was added to the reaction mixture, followed by slowly heating and stirring at a room temperature for 1 hour, and then cooled again to −78° C., and drops of n-BULi (1.1 equivalents (1.6M in hexane)) was slowly added. Subsequently, upon completion of the reaction for 1 hour, iodine methane (1.3 equivalents) was added to the reaction mixture, followed by slowly heating and stirring at a room temperature for 15 hours. And then, the reaction was terminated by adding an aqueous $NH_2Cl$ solution and distilled water. Subsequently, the organic layer was removed under a reduced pressure, followed by recrystallizing with hexane to obtain Sub 1-2.

Meanwhile, examples of Sub 1-2 compounds include, but are not limited to, the following compounds, and FD-MS data of the compounds are given in Table 2 below:

Sub1-2-A
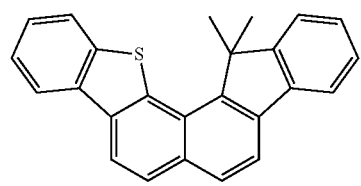

Sub1-2-B
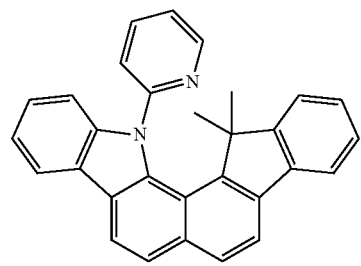

Sub1-2-C
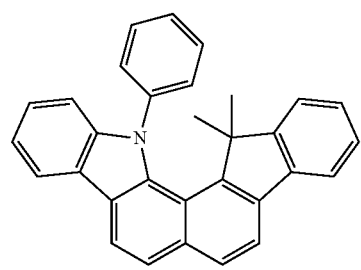

Sub1-2-D
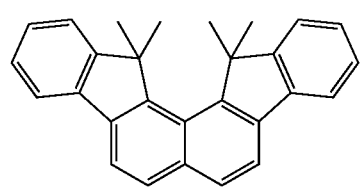

Sub1-2-E
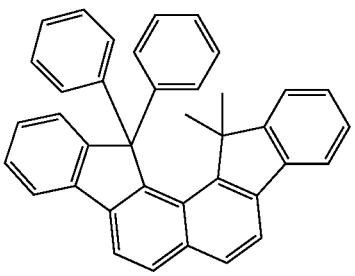

Sub1-2-F
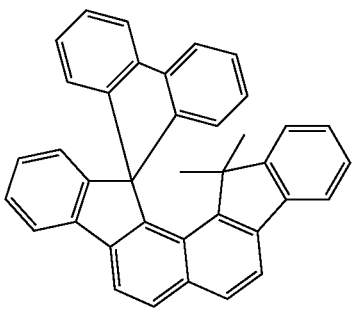

Sub1-2-G
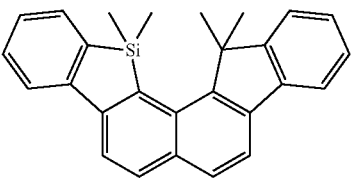

Sub1-2-H
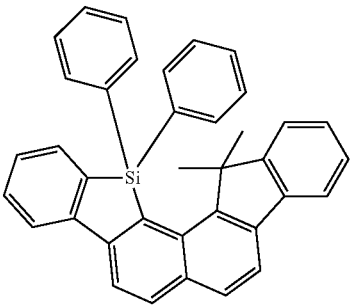

Sub1-2-I
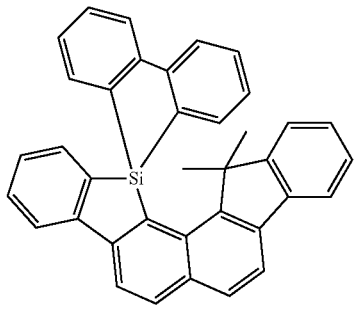

Sub1-2-J
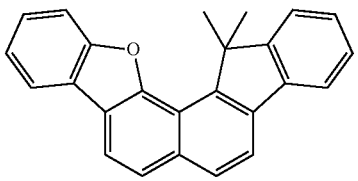

3. Synthesis Method of Sub 1-3
<Reaction Scheme 4>
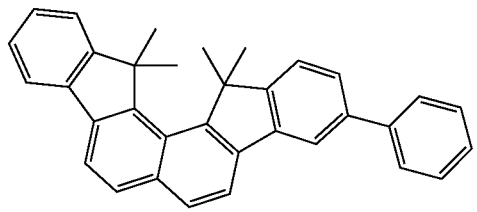
Sub1-2-K
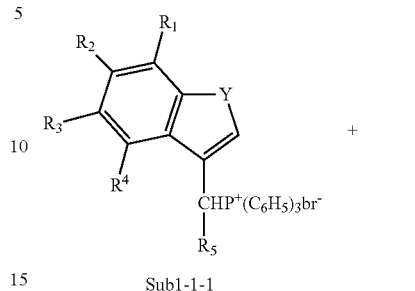
Sub1-1-1
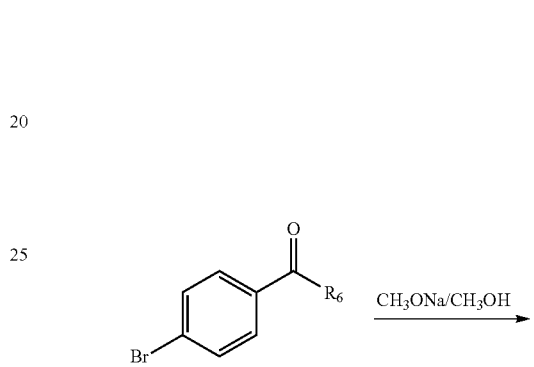
Sub1-3-1
Sub1-2-L
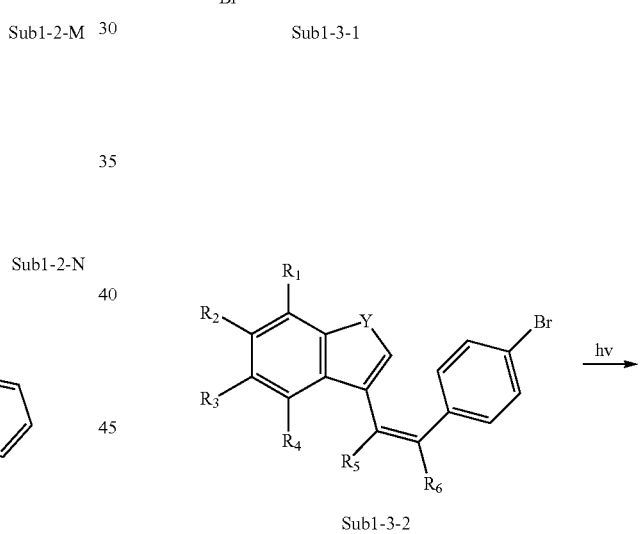
Sub1-3-2
Sub1-2-M
Sub1-2-N
TABLE 2
| Compound | FD-MS | Compound | FD-MS |
|---|---|---|---|
| Sub 1-2-A | m/z = 350.11($C_{25}H_{18}S$ = 350.48) | Sub 1-2-B | m/z = 410.18($C_{30}H_{22}N_2$ = 410.51) |
| Sub 1-2-C | m/z = 409.18($C_{31}H_{23}N$ = 409.52) | Sub 1-2-D | m/z = 360.19($C_{28}H_{24}$ = 360.49) |
| Sub 1-2-E | m/z = 484.22($C_{38}H_{28}$ = 484.63) | Sub 1-2-F | m/z = 482.20($C_{38}H_{26}$ = 482.61) |
| Sub 1-2-G | m/z = 376.16($C_{27}H_{24}Si$ = 376.56) | Sub 1-2-H | m/z = 500.20($C_{37}H_{28}Si$ = 500.70) |
| Sub 1-2-I | m/z = 498.18($C_{37}H_{26}Si$ = 498.69) | Sub 1-2-J | m/z = 334.14($C_{25}H_{18}O$ = 334.41) |
| Sub 1-2-K | m/z = 436.22($C_{34}H_{28}$ = 436.59) | Sub 1-2-L | m/z = 486.20($C_{37}H_{26}O$ = 486.60) |
| Sub 1-2-M | m/z = 406.18($C_{29}H_{26}S$ = 406.58) | Sub 1-2-N | m/z = 486.21($C_{36}H_{26}N_2$ = 486.61) |

-continued

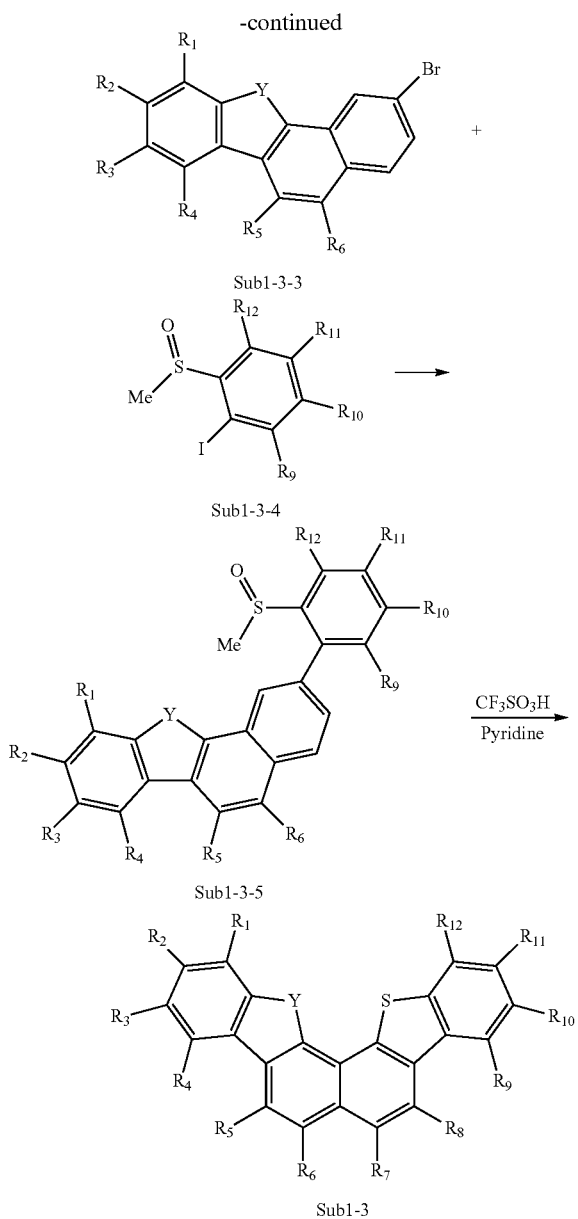

Sub1-3-3

Sub1-3-4

Sub1-3-5

Sub1-3

(1) Synthesis Method of Sub 1-3-2

In a round-bottom flask, Sub 1-1-1 (1 equivalent) and Sub 1-3-1 (1 equivalent) were placed in methanol, followed by stirring at room temperature. Sodium methoxide was placed in the solution, followed by stirring at room temperature for 24 hours. Upon completion of the reaction, the reaction product was extracted with dichrolomethane and water. The extracted organic layer was dried and concentrated, and then the produced organic material was separated by a silica gel column and recrystallized to obtain Sub 1-3-2.

(2) Synthesis Method of Sub 1-3-3

In a round-bottom flask, Sub 1-3-2 (1 equivalent), and iodine were placed in dry benzene, followed by being subjected to UV treatment with a UV lamp during the generation of bubbles from the solution, and the progression was monitored by TLC. After seven hours, the solvent was removed in a vacuum, followed by recrystallizing with ethanol to obtain Sub 1-3-3.

(3) Synthesis Method of Sub 1-3-5

Sub 1-3-3 (1 equivalent), Sub 1-3-4 (1 equivalent), Ph(PPh$_3$) and NaCO$_3$ were dissolved in anhydrous THF and a little water, followed by refluxing for 24 hrs. Upon completion of the reaction, the reactant was cooled to room temperature. And then the reactant was extracted with CH$_2$Cl$_2$ and washed with water, followed by removing water with anhydrous MgSO$_4$. Subsequently, the reactant was treated with a vacuum-filtration, followed by concentrating the organic solvent, and then the produced organic material was separated by a column chromatograph to obtain Sub 1-3-5.

(4) Synthesis Method of Sub 1-3

Sub 1-3-5 was dissolved in solvent of trifluoromethanesulfonic acid, followed by stirring at room temperature for 48 hours. Upon completion of the reaction, the reactant was added in the mixture of water and pyridine, followed by refluxing for 20 minutes. Subsequently, the refluxed reactant was cooled to room temperature, followed by extracting with CH$_2$Cl$_2$ and washing with water. And then a little water from the reactant was removed with anhydrous MgSO$_4$, followed by vacuum-filtration. Subsequently, the product that was produced by concentrating the organic solvent was separated by a column chromatograph to obtain Sub 1-3.

Meanwhile, examples of Sub 1-3 compounds include, but are not limited to, the following compounds, and FD-MS data of the compounds are given in Table 3 below:

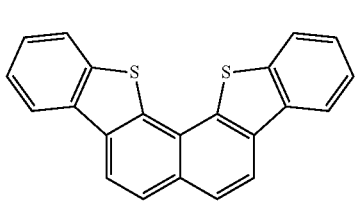

Sub1-3-A

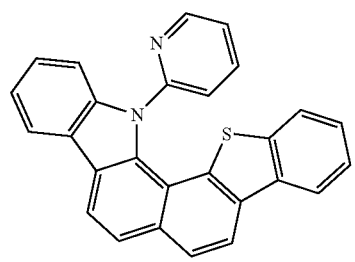

Sub1-3-B

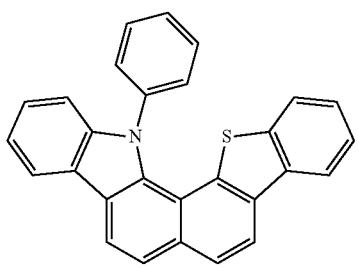

Sub1-3-C

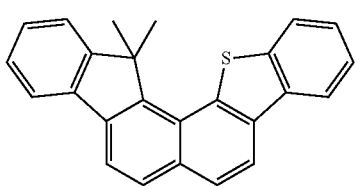

Sub1-3-D

Sub1-3-E
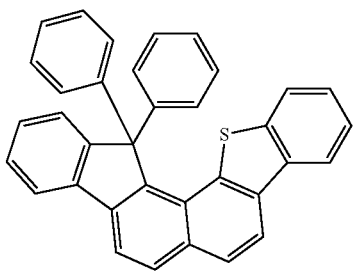
Sub1-3-F
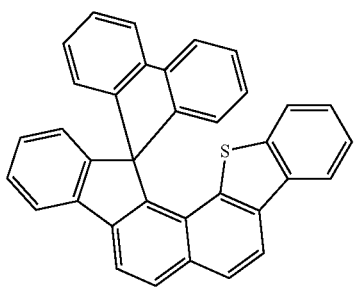
Sub1-3-G
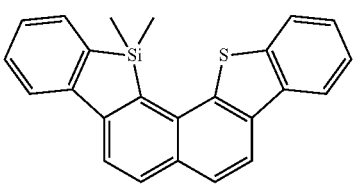
Sub1-3-H
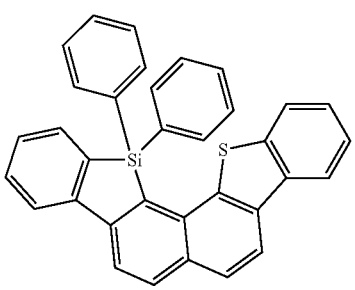
Sub1-3-I
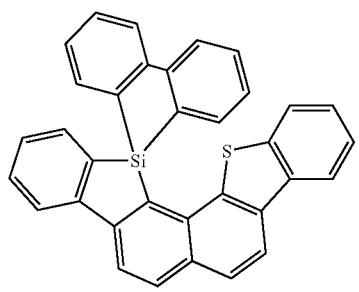
Sub1-3-J
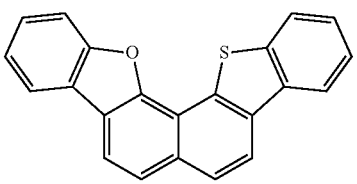
Sub1-3-K
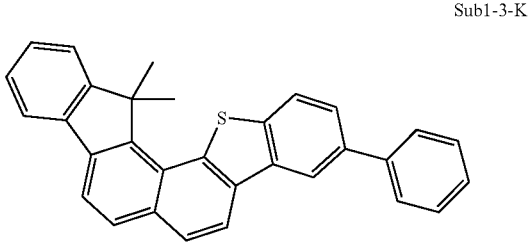
Sub1-3-L
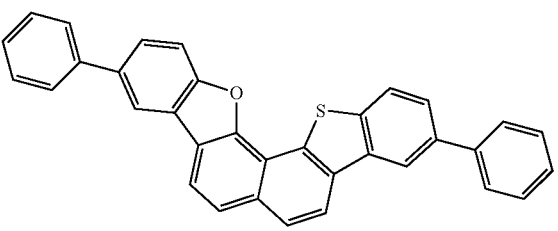
Sub1-3-M
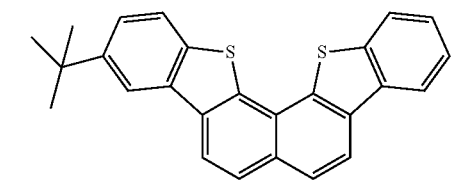
Sub1-3-N
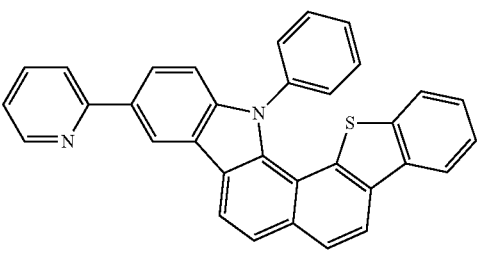

TABLE 3

| Compound | FD-MS | Compound | FD-MS |
|---|---|---|---|
| Sub 1-3-A | m/z = 340.04($C_{22}H_{12}S_2$ = 340.46) | Sub 1-3-B | m/z = 400.10($C_{27}H_{03}N_2S$ = 400.49) |
| Sub 1-3-C | m/z = 399.11($C_{28}H_{17}NS$ = 399.51) | Sub 1-3-D | m/z = 350.11($C_{25}H_{15}S$ = 350.48) |
| Sub 1-3-E | m/z = 474.14($C_{35}H_{22}S$ = 474.61) | Sub 1-3-F | m/z = 472.13($C_{35}H_{20}S$ = 472.60) |
| Sub 1-3-G | m/z = 366.09($C_{24}H_{18}SSi$ = 366.55) | Sub 1-3-H | m/z = 490.12($C_{34}H_{22}SSi$ = 490.69) |
| Sub 1-3-I | m/z = 488.11($C_{34}H_{20}SSi$ = 488.67) | Sub 1-3-J | m/z = 324.06($C_{22}H_{12}OS$ = 324.40) |
| Sub 1-3-K | m/z = 426.14($C_{31}H_{22}S$ = 426.57) | Sub 1-3-L | m/z = 476.12($C_{34}H_{20}OS$ = 476.59) |
| Sub 1-3-M | m/z = 396.10 ($C_{26}H_{20}S_2$ = 396.57) | Sub 1-3-N | m/z = 476.13($C_{33}H_{20}N_2S$ = 476.59) |

II. Examples of Sub 2

Examples of Sub 2 compounds in the reaction scheme 1 include, but are not limited to, the following compounds, and FD-MS data of the compounds are given in Table 4 below:

Sub 2-1

Sub 2-2

Sub 2-3

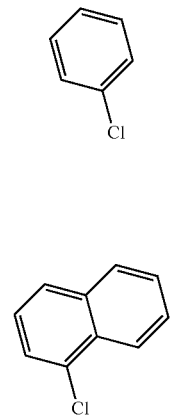

Sub 2-4

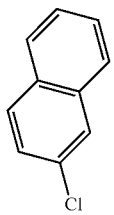

Sub 2-5

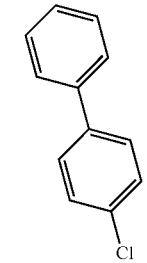

-continued

Sub 2-6

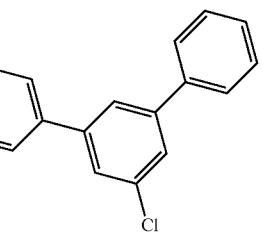

Sub 2-7

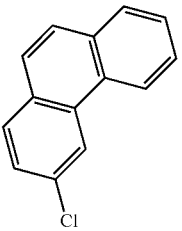

Sub 2-8

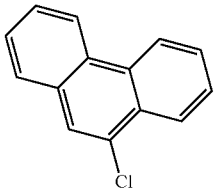

Sub 2-9

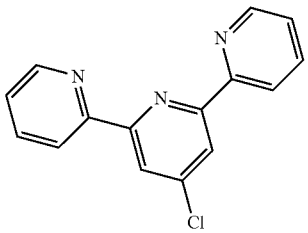

Sub 2-10

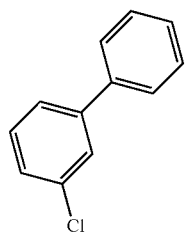

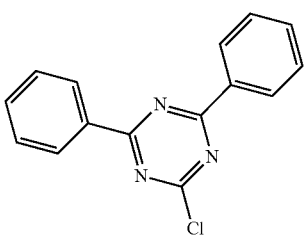

Sub 2-11
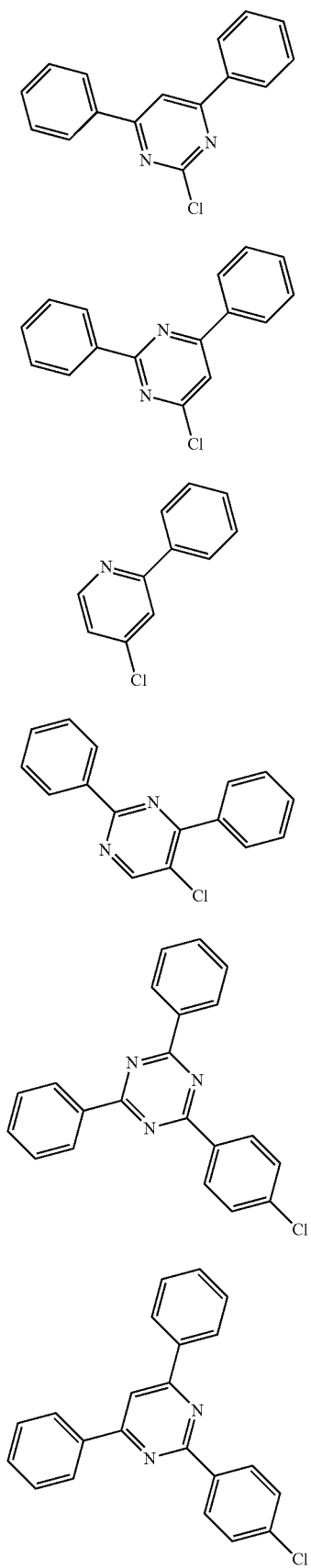
Sub 2-12
Sub 2-13
Sub 2-14
Sub 2-15
Sub 2-16
Sub 2-17
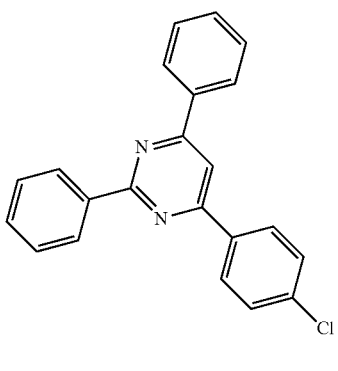
Sub 2-18
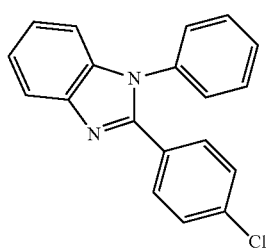
Sub 2-19
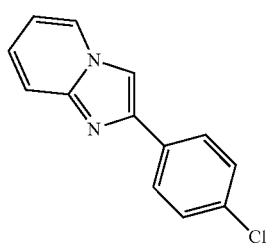
Sub 2-20
Sub 2-21
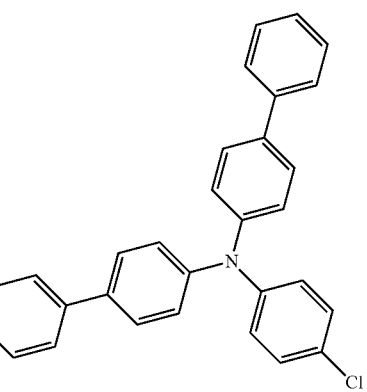

Sub 2-22
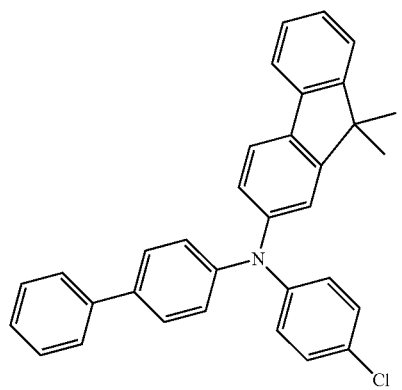
Sub 2-23
Sub 2-24
Sub 2-25
Sub 2-26
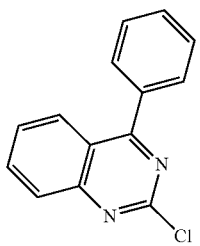
Sub 2-27
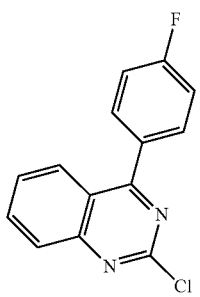
Sub 2-28
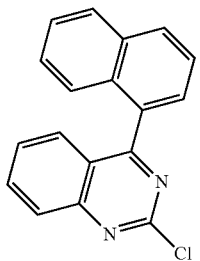
Sub 2-29
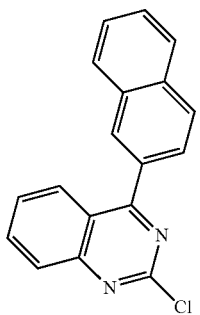
Sub 2-30
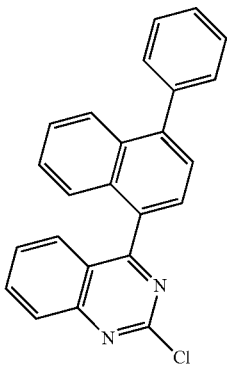

Sub 2-31
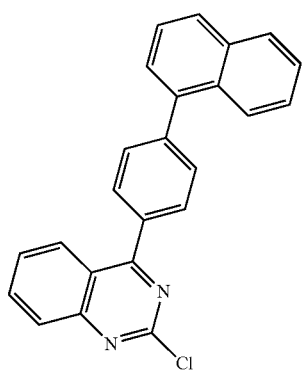
Sub 2-32
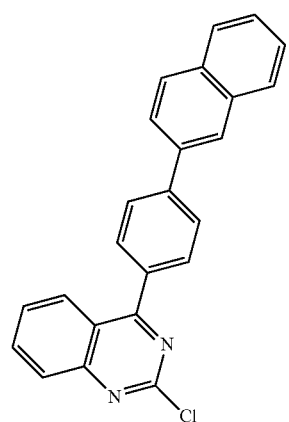
Sub 2-33
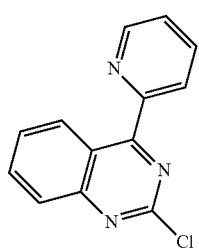
Sub 2-34
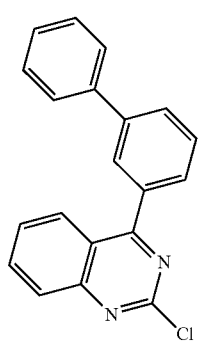
Sub 2-35
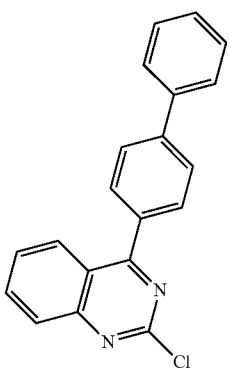
Sub 2-36
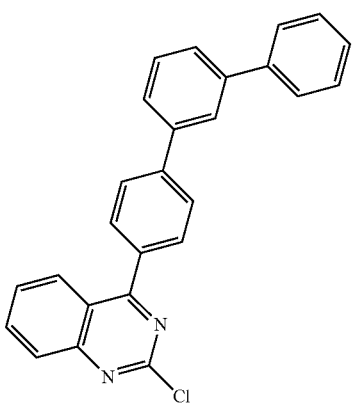
Sub 2-37
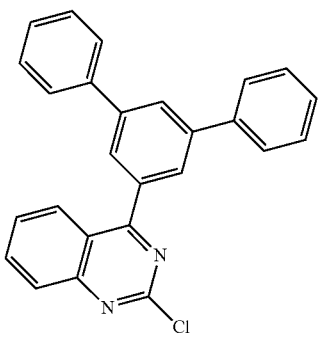
Sub 2-38
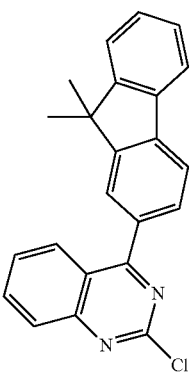

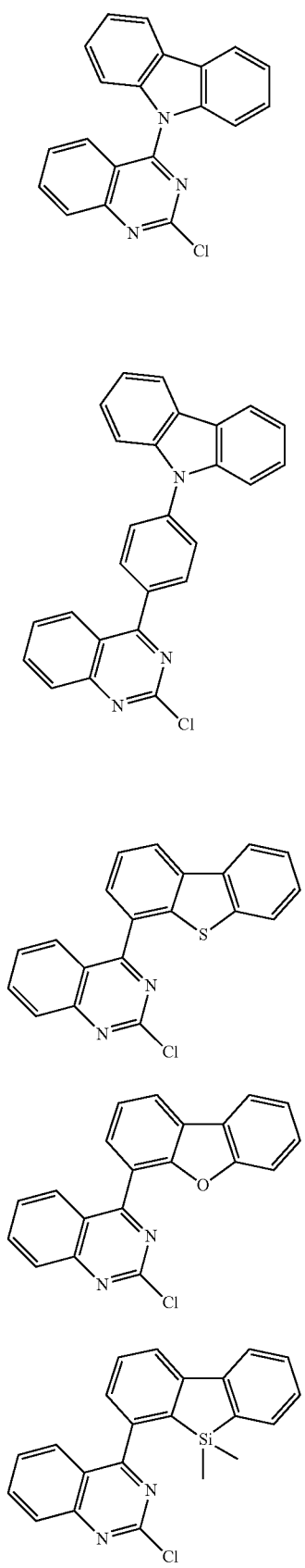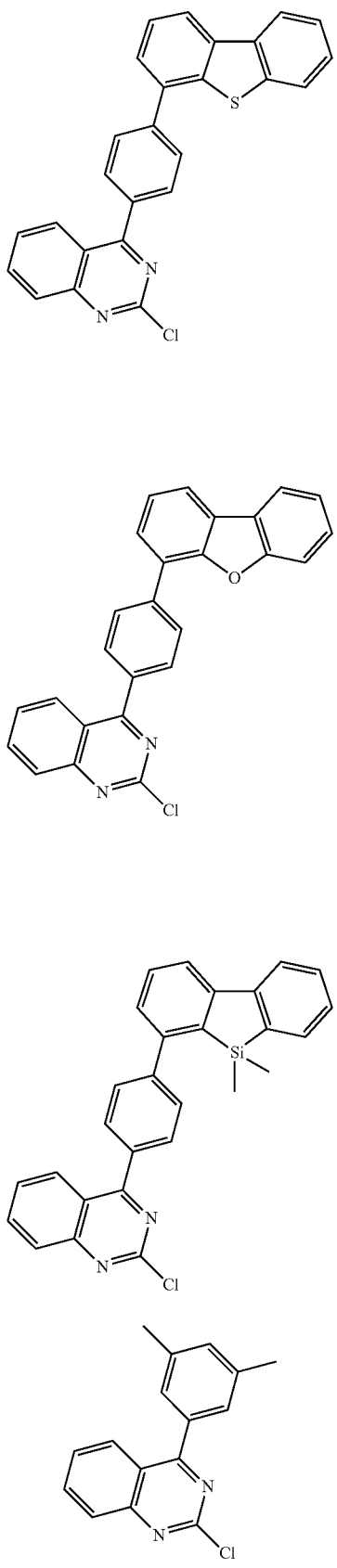

Sub 2-48
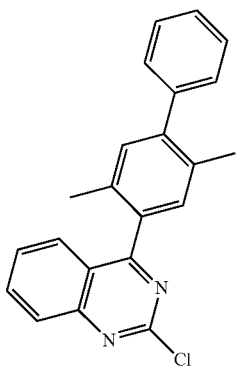
Sub 2-49
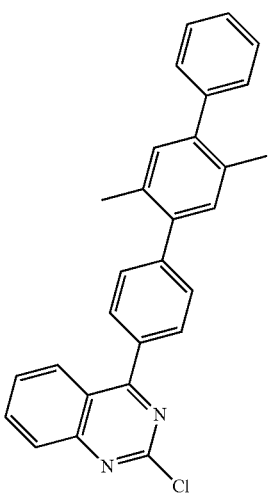
Sub 2-50
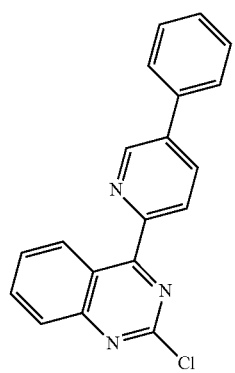
Sub 2-51
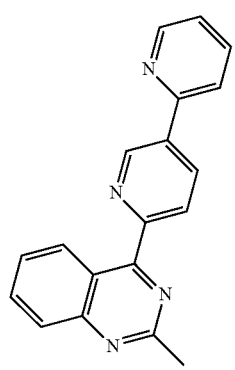
Sub 2-52
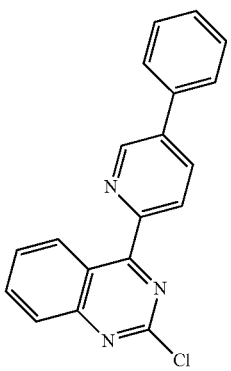
Sub 2-53
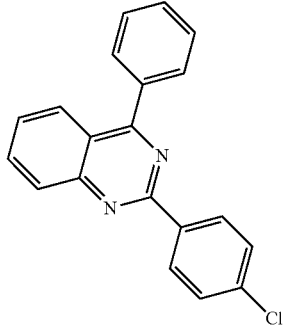
Sub 2-54
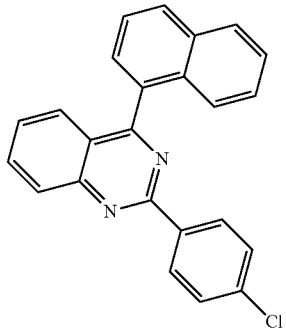
Sub 2-55
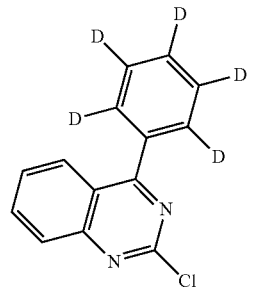
Sub 2-56
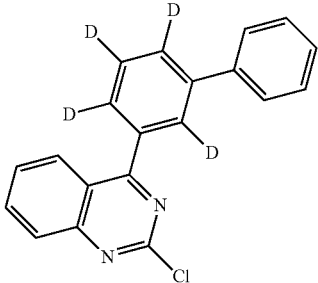

Sub 2-57
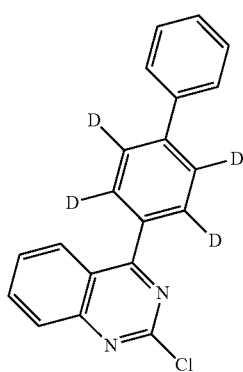
Sub 2-58
Sub 2-59
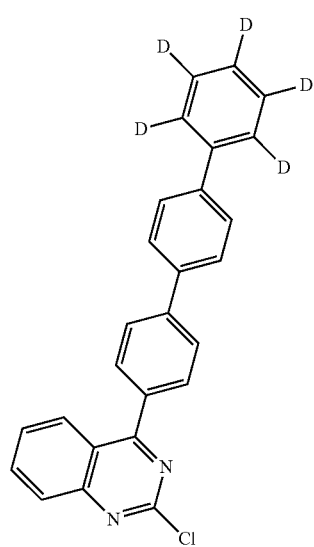
Sub 2-60
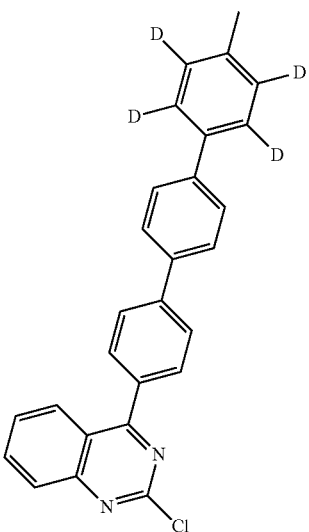
Sub 2-61
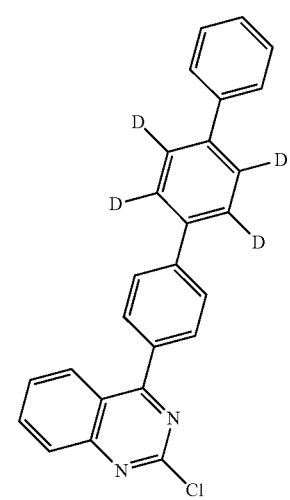
Sub 2-62
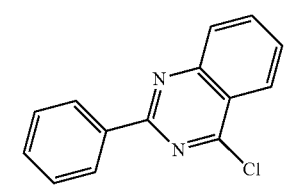
Sub 2-63
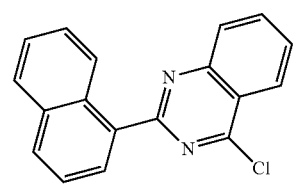

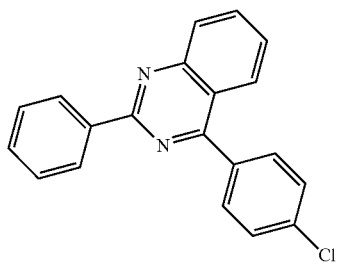

Sub 2-64

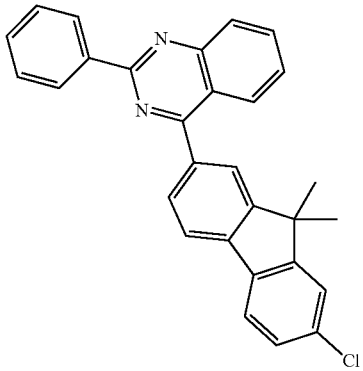

Sub 2-65

TABLE 4

| Compound | FD-MS | Compound | FD-MS |
| --- | --- | --- | --- |
| Sub 2-1 | m/z = 112.01($C_6H_5Cl$ = 112.56) | Sub 2-2 | m/z = 162.02($C_{10}H_7Cl$ = 162.62) |
| Sub 2-3 | m/z = 188.04($C_{12}H_9Cl$ = 188.65) | Sub 2-4 | m/z = 188.04($C_{12}H_9Cl$ = 188.65) |
| Sub 2-5 | m/z = 188.04($C_{12}H_9Cl$ = 188.65) | Sub 2-6 | m/z = 212.04($C_{14}H_9Cl$ = 212.67) |
| Sub 2-7 | m/z = 212.04($C_{14}H_9Cl$ = 212.67) | Sub 2-8 | m/z = 212.04($C_{14}H_9Cl$ = 212.67) |
| Sub 2-9 | m/z = 267.06($C_{15}H_{10}ClN_3$ = 267.71) | Sub 2-10 | m/z = 267.06($C_{15}H_{10}ClN_3$ = 267.71) |
| Sub 2-11 | m/z = 266.06($C_{16}H_{11}ClN_2$ = 266.72) | Sub 2-12 | m/z = 266.06($C_{16}H_{11}ClN_2$ = 266.72) |
| Sub 2-13 | m/z = 189.03($C_{11}H_8ClN$ = 189.64) | Sub 2-14 | m/z = 266.06($C_{16}H_{11}ClN_2$ = 266.72) |
| Sub 2-15 | m/z = 343.09($C_{21}H_{14}ClN_3$ = 343.81) | Sub 2-16 | m/z = 342.09($C_{22}H_{15}ClN_2$ = 342.82) |
| Sub 2-17 | m/z = 342.09($C_{22}H_{15}ClN_2$ = 342.82) | Sub 2-18 | m/z = 304.08($C_{19}H_{13}ClN_2$ = 304.77) |
| Sub 2-19 | m/z = 228.05($C_{13}H_9ClN_2$ = 228.68) | Sub 2-20 | m/z = 239.05($C_{15}H_{10}ClN$ = 239.70) |
| Sub 2-21 | m/z = 431.14($C_{30}H_{22}ClN$ = 431.96) | Sub 2-22 | m/z = 471.18($C_{33}H_{26}ClN$ = 472.02) |
| Sub 2-23 | m/z = 595.21($C_{43}H_{30}ClN$ = 596.16) | Sub 2-24 | m/z = 593.19($C_{43}H_{28}ClN$ = 594.14) |
| Sub 2-25 | m/z = 461.10($C_{30}H_{20}ClNS$ = 462.00) | Sub 2-26 | m/z = 240.05($C_{14}H_9ClN_2$ = 240.69) |
| Sub 2-27 | m/z = 258.04($C_{14}H_8ClFN_2$ = 258.68) | Sub 2-28 | m/z = 290.06($C_{18}H_{11}ClN_2$ = 290.75) |
| Sub 2-29 | m/z = 290.06($C_{18}H_{11}ClN_2$ = 290.75) | Sub 2-30 | m/z = 366.09($C_{24}H_{15}ClN_2$ = 366.84) |
| Sub 2-31 | m/z = 366.09($C_{24}H_{15}ClN_2$ = 366.84) | Sub 2-32 | m/z = 366.09($C_{24}H_{15}ClN_2$ = 366.84) |
| Sub 2-33 | m/z = 241.04($C_{13}H_8ClN_3$ = 241.68) | Sub 2-34 | m/z = 316.08($C_{20}H_{13}ClN_2$ = 316.78) |
| Sub 2-35 | m/z = 316.08($C_{20}H_{13}ClN_2$ = 316.78) | Sub 2-36 | m/z = 392.11 ($C_{26}H_{17}ClN_2$ = 392.88) |
| Sub 2-37 | m/z = 392.11 ($C_{26}H_{17}ClN_2$ = 392.88) | Sub 2-38 | m/z = 356.11 ($C_{23}H_{17}ClN_2$ = 356.85) |
| Sub 2-39 | m/z = 329.07($C_{20}H_{12}ClN_3$ = 329.78) | Sub 2-40 | m/z = 405.10($C_{26}H_{16}ClN_3$ = 405.88) |
| Sub 2-41 | m/z = 346.03($C_{20}H_{11}ClN_2S$ = 346.83) | Sub 2-42 | m/z = 330.06($C_{20}H_{11}ClN_2O$ = 330.77) |
| Sub 2-43 | m/z = 372.08($C_{22}H_{17}ClN_2Si$ = 372.92) | Sub 2-44 | m/z = 422.06($C_{26}H_{15}ClN_2S$ = 422.93) |
| Sub 2-45 | m/z = 406.09($C_{26}H_{15}ClN_2O$ = 406.86) | Sub 2-46 | m/z = 448.12($C_{28}H_{21}ClN_2Si$ = 449.02 |
| Sub 2-47 | m/z = 268.08($C_{16}H_{13}ClN_2$ = 268.74) | Sub 2-48 | m/z = 420.14($C_{28}H_{21}ClN_2$ = 344.84) |
| Sub 2-49 | m/z = 420.14($C_{28}H_{21}ClN_2$ = 420.93) | Sub 2-50 | m/z = 317.07($C_{19}H_{12}ClN_3$ = 317.77) |
| Sub 2-51 | m/z = 318.07($C_{18}H_{11}ClN_4$ = 318.76) | Sub 2-52 | m/z = 317.07($C_{19}H_{12}ClN_3$ = 317.77) |
| Sub 2-53 | m/z = 316.08($C_{20}H_{13}ClN_2$ = 316.78) | Sub 2-54 | m/z = 366.09($C_{24}H_{15}ClN_2$ = 366.84) |
| Sub 2-55 | m/z = 245.08($C_{14}H_4D_5ClN_2$ = 245.72) | Sub 2-56 | m/z = 320.10($C_{20}H_5D_4ClN_2$ = 320.81) |
| Sub 2-57 | m/z = 320.10($C_{20}H_5D_4ClN_2$ = 320.81) | Sub 2-58 | m/z = 320.10($C_{20}H_5D_4ClN_2$ = 320.81) |
| Sub 2-59 | m/z = 397.14($C_{26}H_{12}D_5ClN_2$ = 397.9) | Sub 2-60 | m/z = 410.15($C_{27}H_{15}D_4ClN_2$ = 410.93) |
| Sub 2-61 | m/z = 396.13($C_{26}H_{13}D_4ClN_2$ = 396.9) | Sub 2-62 | m/z = 240.05($C_{14}H_9ClN_2$ = 240.69) |
| Sub 2-63 | m/z = 290.06($C_{18}H_{11}ClN_2$ = 290.75) | Sub 2-64 | m/z = 316.08($C_{20}H_{13}ClN_2$ = 316.78) |
| Sub 2-65 | m/z = 432.14($C_{29}H_{21}ClN_2$ = 432.94) | | |

III. Synthesis Method of Final Products

Sub 1 (1 equivalent) and Sub 2 (1.1 equivalent) were placed in toluene, and Pd$_2$(dba)$_3$ (0.05 equivalent), PPh$_3$ (0.1 equivalent) and NaOt-Bu (3 equivalents) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain final product.

1. Synthesis Method of P-6

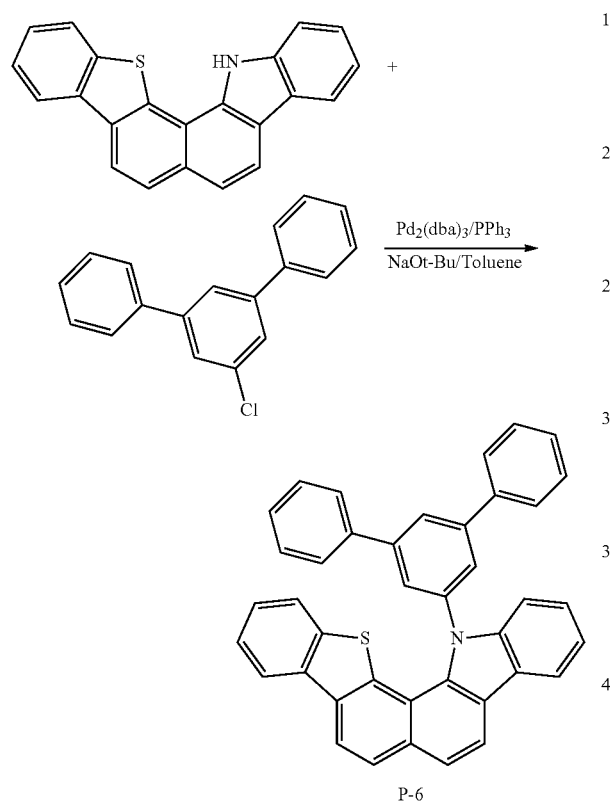

P-6

14H-benzo[4',5']thieno[3',2':5,6]benzo[1,2-a]carbazole (6.5 g, 20 mmol), 5'-chloro-1,1':3', and 1"-terphenyl (6.4 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 7.1 g of product (yield: 64%).

2. Synthesis Method of P-22

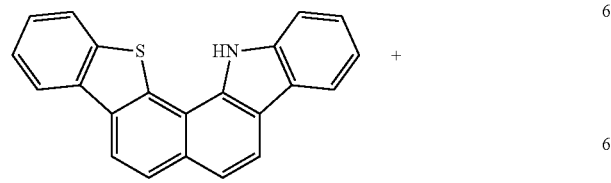

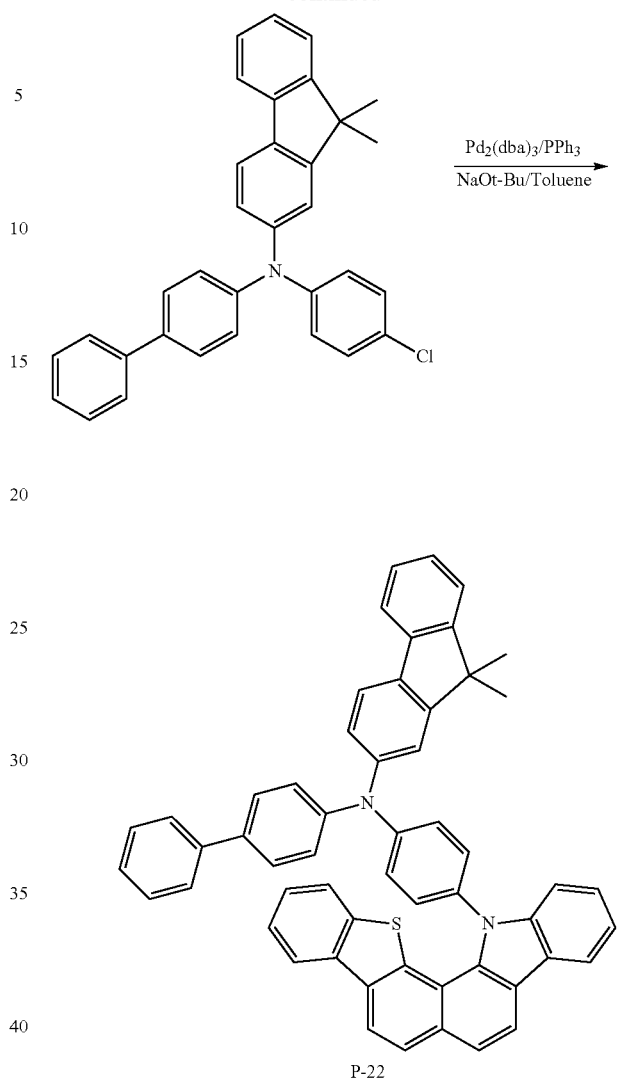

P-22

14H-benzo[4',5']thieno[3',2':5,6]benzo[1,2-a]carbazole (6.5 g, 20 mmol), and N-([1,1'-biphenyl]-4-yl)-N-(4-chlorophenyl)-9,9-dimethyl-9H-fluoren-2-amine (11.3 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 9.3 g of product (yield: 61%).

3. Synthesis Method of P-26

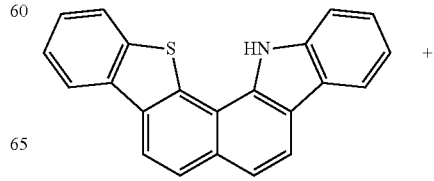

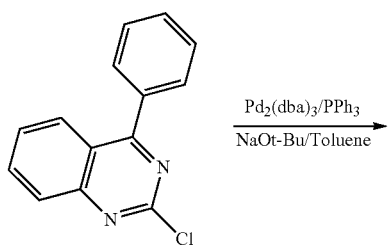

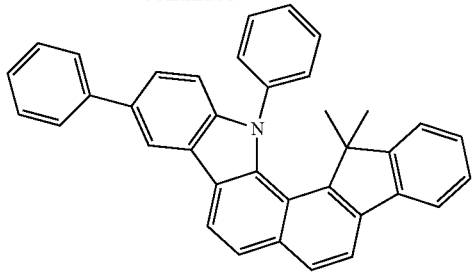

P-72

14,14-dimethyl-10-phenyl-13,14-dihydrofluoreno[1,2-a] carbazole (8.2 g, 20 mmol) and chlorobenzene (2.7 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 5.6 g of product (yield: 58%).

5. Synthesis Method of P-82

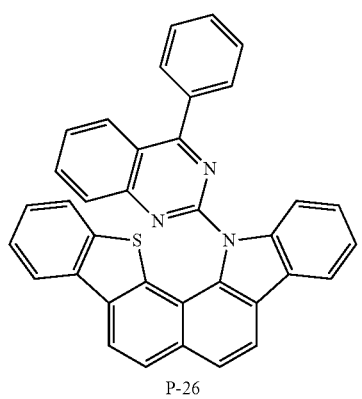

P-26

14H-benzo[4',5']thieno[3',2':5,6]benzo[1,2-a]carbazole (6.5 g, 20 mmol) and 2-chloro-4-phenylquinazoline (5.8 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol)) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 6.6 g of product (yield: 63%).

4. Synthesis Method of P-72

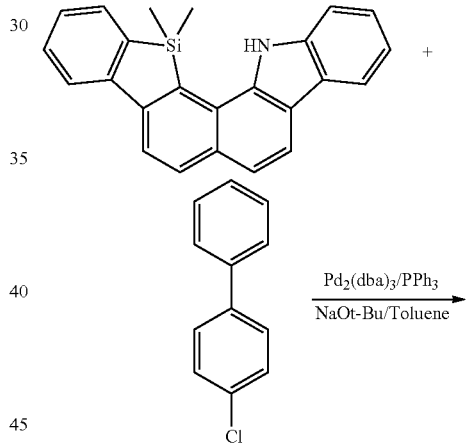

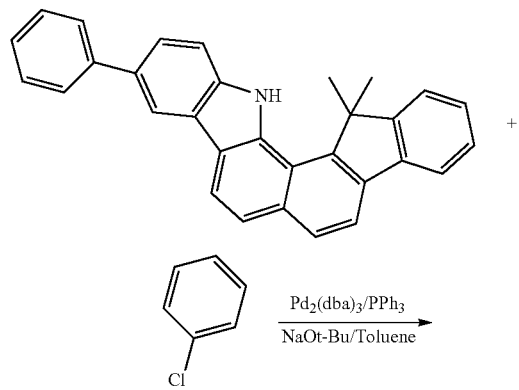

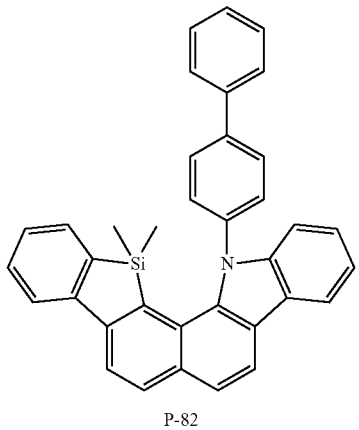

P-82

14,14-dimethyl-13,14-dihydrobenzo[4',5']silolo[3',2':5,6] benzo[1,2-a]carbazole (7.0 g, 20 mmol) and 4-chloro-1,1'-biphenyl (4.5 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 5.5 g of product (yield: 55%).

6. Synthesis Method of P-87

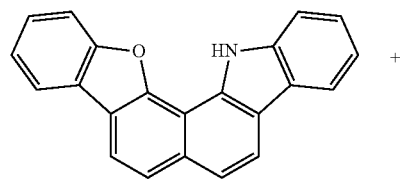

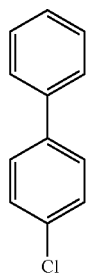

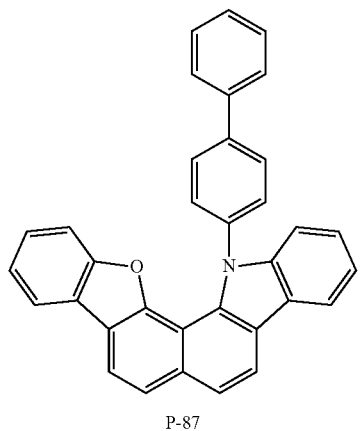

P-87

14H-benzo[2,3]benzofuro[7,6-a]carbazole (6.1 g, 20 mmol) and 4-chloro-1,1'-biphenyl (4.5 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 5.4 g of product (yield: 59%).

7. Synthesis Method of P-107

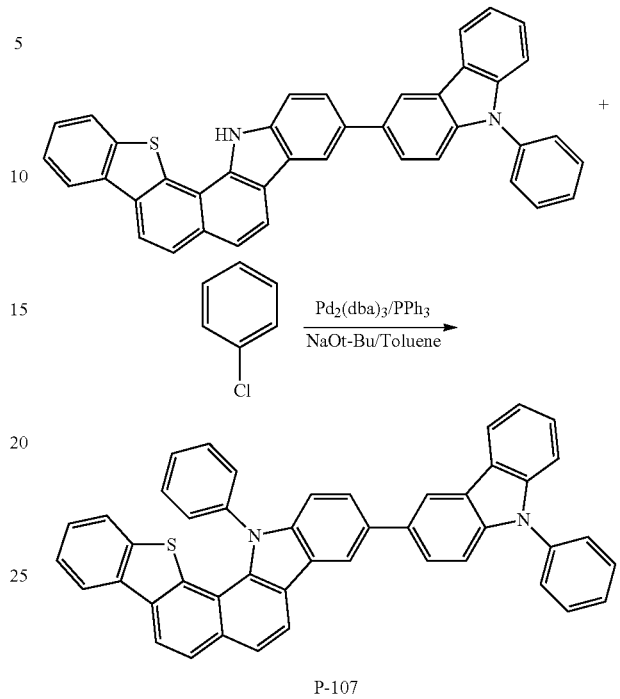

P-107

3-(9-phenyl-9H-carbazol-3-yl)-14H-benzo[4',5']thieno[3',2':5,6]benzo[1,2-a]carbazole (11.3 g, 20 mmol) and chlorobenzene (2.7 g, 24 mmol) were placed in toluene, and Pd$_2$(dba)$_3$ (1.0 g, 1 mmol), PPh$_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with MgSO$_4$ and concentrated, and then the produced organic material was separated by a silica gel column and recrystallized to obtain 7.9 g of product (yield: 62%).

8. Synthesis Method of P-155

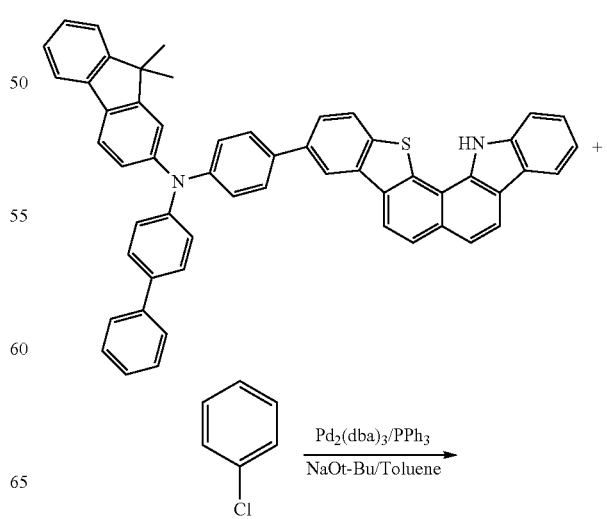

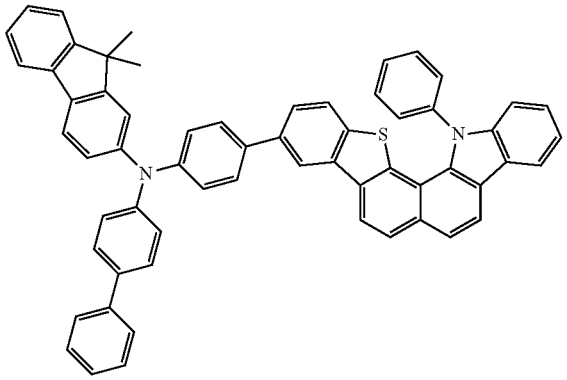

P-155

N-(4-(14H-benzo[4',5']thieno[3',2':5,6]benzo[1,2-a]carbazol-10-yl)phenyl)-N-([1,1'-biphenyl]-4-yl)-9,9-dimethyl-9H-fluoren-2-amine (15.2 g, 20 mmol) and chlorobenzene (2.7 g, 24 mmol) were placed in toluene, and $Pd_2(dba)_3$ (1.0 g, 1 mmol), $PPh_3$ (0.5 g, 2 mmol) and NaOt-Bu (5.8 g, 60 mmol) were added to the reaction solution, followed by refluxing at 100° C. for 24 hours under stirring. Upon completion of the reaction, the reaction product was extracted with ether and water. The extracted organic layer was dried with $MgSO_4$ and concentrated, and then the produced organic material was separated by a silica gel column and recrystallized to obtain 10.5 g of product (yield: 63%).

Meanwhile, FD-MS data of the compounds P-1 to P-165 prepared in the Synthesis Examples of the present invention are given in Table 5 below.

TABLE 5

| Compound | FD-MS | Compound | FD-MS |
|---|---|---|---|
| P-1 | m/z = 399.11($C_{28}H_{17}NS$ = 558.71) | P-2 | m/z = 449.12($C_{32}H_{19}NS$ = 449.56) |
| P-3 | m/z = 449.12($C_{32}H_{19}NS$ = 449.56) | P-4 | m/z = 475.14($C_{34}H_{21}NS$ = 475.60) |
| P-5 | m/z = 475.14($C_{34}H_{21}NS$ = 475.60) | P-6 | m/z = 551.17($C_{40}H_{25}NS$ = 551.70) |
| P-7 | m/z = 551.17($C_{40}H_{25}NS$ = 551.70) | P-8 | m/z = 551.17($C_{40}H_{25}NS$ = 551.70) |
| P-9 | m/z = 554.16($C_{37}H_{22}N_4S$ = 554.66) | P-10 | m/z = 554.16($C_{37}H_{22}N_4S$ = 554.66) |
| P-11 | m/z = 553.16($C_{38}H_{23}N_3S$ = 553.67) | P-12 | m/z = 553.16($C_{38}H_{23}N_3S$ = 553.67) |
| P-13 | m/z = 476.13($C_{33}H_{20}N_2S$ = 476.59) | P-14 | m/z = 553.16($C_{38}H_{23}N_3S$ = 553.67) |
| P-15 | m/z = 630.19($C_{43}H_{26}N_4S$ = 630.76) | P-16 | m/z = 629.19($C_{44}H_{27}N_3S$ = 629.77) |
| P-17 | m/z = 629.19($C_{44}H_{27}N_3S$ = 629.77) | P-18 | m/z = 591.18($C_{41}H_{25}N_3S$ = 591.72) |
| P-19 | m/z = 515.15($C_{35}H_{21}N_3S$ = 515.63) | P-20 | m/z = 526.15($C_{37}H_{22}N_2S$ = 526.65) |
| P-21 | m/z = 718.24($C_{52}H_{34}N_2S$ = 718.90) | P-22 | m/z = 758.28($C_{55}H_{38}N_2S$ = 758.97) |
| P-23 | m/z = 882.31($C_{65}H_{42}N_2S$ = 883.11) | P-24 | m/z = 880.29($C_{65}H_{40}N_2S$ = 881.09) |
| P-25 | m/z = 748.20($C_{52}H_{32}N_2S_2$ = 748.95) | P-26 | m/z = 527.15($C_{36}H_{21}N_3S$ = 527.64) |
| P-27 | m/z = 545.14($C_{36}H_{20}FN_3S$ = 545.63) | P-28 | m/z = 577.16($C_{40}H_{23}N_3S$ = 577.70) |
| P-29 | m/z = 577.16($C_{40}H_{23}N_3S$ = 577.70) | P-30 | m/z = 653.19($C_{46}H_{27}N_3S$ = 656.79) |
| P-31 | m/z = 653.19($C_{46}H_{27}N_3S$ = 656.79) | P-32 | m/z = 653.19($C_{46}H_{27}N_3S$ = 656.79) |
| P-33 | m/z = 528.14($C_{35}H_{20}N_4S$ = 528.63) | P-34 | m/z = 603.18($C_{42}H_{25}N_3S$ = 603.73) |
| P-35 | m/z = 603.18($C_{42}H_{25}N_3S$ = 603.73) | P-36 | m/z = 679.21($C_{48}H_{29}N_3S$ = 679.83) |
| P-37 | m/z = 679.21($C_{48}H_{29}N_3S$ = 679.83) | P-38 | m/z = 643.21($C_{45}H_{29}N_3S$ = 643.80) |
| P-39 | m/z = 616.17($C_{42}H_{24}N_4S$ = 616.73) | P-40 | m/z = 692.20($C_{48}H_{28}N_4S$ = 692.83) |
| P-41 | m/z = 633.13($C_{42}H_{23}N_3S_2$ = 633.78) | P-42 | m/z = 617.16($C_{42}H_{23}N_3OS$ = 617.72) |
| P-43 | m/z = 659.19($C_{44}H_{29}N_3SSi$ = 659.87) | P-44 | m/z = 709.16($C_{48}H_{27}N_3S_2$ = 709.88) |
| P-45 | m/z = 693.19($C_{48}H_{27}N_3OS$ = 693.81) | P-46 | m/z = 735.22($C_{50}H_{33}N_3SSi$ = 735.97) |
| P-47 | m/z = 555.18($C_{38}H_{25}N_3S$ = 555.69) | P-48 | m/z = 631.21($C_{44}H_{29}N_3S$ = 631.79) |
| P-49 | m/z = 707.24($C_{50}H_{33}N_3S$ = 707.88) | P-50 | m/z = 604.17($C_{41}H_{24}N_4S$ = 604.72) |
| P-51 | m/z = 605.17($C_{40}H_{23}N_5S$ = 605.71) | P-52 | m/z = 604.17($C_{41}H_{24}N_4S$ = 604.72) |
| P-53 | m/z = 603.18($C_{42}H_{25}N_3S$ = 603.73) | P-54 | m/z = 653.19($C_{46}H_{27}N_3S$ = 653.79) |
| P-55 | m/z = 532.18($C_{36}H_{16}N_3S$ = 532.67) | P-56 | m/z = 607.20($C_{42}H_{21}D_4N_3S$ = 607.76) |
| P-57 | m/z = 607.20($C_{42}H_{21}D_4N_3S$ = 607.76) | P-58 | m/z = 608.21($C_{42}H_{20}D_5N_3S$ = 608.76) |
| P-59 | m/z = 684.24($C_{48}H_{24}D_5N_3S$ = 684.86) | P-60 | m/z = 697.25($C_{49}H_{27}D_4N_3S$ = 697.88) |
| P-61 | m/z = 683.23($C_{48}H_{25}D_4N_3S$ = 683.85) | P-62 | m/z = 527.15($C_{36}H_{21}N_3S$ = 527.64) |
| P-63 | m/z = 577.16($C_{40}H_{23}N_3S$ = 577.70) | P-64 | m/z = 603.18($C_{42}H_{25}N_3S$ = 603.73) |
| P-65 | m/z = 719.24($C_{51}H_{33}N_3S$ = 719.89) | P-66 | m/z = 340.04($C_{22}H_{12}S_2$ = 340.46) |
| P-67 | m/z = 426.14($C_{31}H_{22}S$ = 426.57) | P-68 | m/z = 476.12($C_{34}H_{20}OS$ = 476.59) |
| P-69 | m/z = 507.11($C_{34}H_{21}NS_2$ = 507.67) | P-70 | m/z = 546.18($C_{38}H_{30}SSi$ = 546.80) |
| P-71 | m/z = 458.18($C_{34}H_{22}N_2$ = 458.55) | P-72 | m/z = 485.21($C_{37}H_{27}N$ = 485.62) |
| P-73 | m/z = 535.19($C_{40}H_{25}NO$ = 535.63) | P-74 | m/z = 586.22($C_{42}H_{34}N_4$ = 586.68) |
| P-75 | m/z = 533.21($C_{41}H_{27}N$ = 533.66) | P-76 | m/z = 360.19($C_{28}H_{24}$ = 360.49) |
| P-77 | m/z = 350.11($C_{25}H_{18}S$ = 350.48) | P-78 | m/z = 458.17($C_{35}H_{22}O$ = 458.55) |
| P-79 | m/z = 537.22($C_{39}H_{27}N_3$ = 537.65) | P-80 | m/z = 376.16($C_{27}H_{24}Si$ = 376.56) |
| P-81 | m/z = 392.14($C_{26}H_{24}Si_2$ = 392.64) | P-82 | m/z = 501.19($C_{36}H_{27}NSi$ = 501.69) |
| P-83 | m/z = 350.11($C_{24}H_{18}OSi$ = 350.48) | P-84 | m/z = 468.17($C_{32}H_{28}Si_2$ = 468.74) |
| P-85 | m/z = 787.31($C_{56}H_{45}NSi_2$ = 788.13) | P-86 | m/z = 308.08($C_{22}H_{12}O_2$ = 308.33) |
| P-87 | m/z = 459.16($C_{34}H_{21}NO$ = 459.54) | P-88 | m/z = 364.15($C_{25}H_{20}O_2$ = 364.44) |
| P-89 | m/z = 384.12($C_{28}H_{16}O_2$ = 364.43) | P-90 | m/z = 703.25($C_{52}H_{33}NO_2$ = 703.82) |
| P-91 | m/z = 642.21($C_{46}H_{30}N_2S$ = 642.81) | P-92 | m/z = 692.23($C_{50}H_{32}N_2S$ = 692.87) |
| P-93 | m/z = 692.23($C_{50}H_{32}N_2S$ = 692.87) | P-94 | m/z = 718.24($C_{52}H_{34}N_2S$ = 718.90) |
| P-95 | m/z = 834.31($C_{61}H_{42}N_2S$ = 835.06) | P-96 | m/z = 626.24($C_{46}H_{30}N_2S$ = 626.74) |
| P-97 | m/z = 676.25($C_{50}H_{32}N_2O$ = 676.80) | P-98 | m/z = 676.25($C_{50}H_{32}N_2O$ = 676.80) |
| P-99 | m/z = 702.27($C_{52}H_{34}N_2O$ = 702.84) | P-100 | m/z = 818.33($C_{61}H_{42}N_2O$ = 819.00) |
| P-101 | m/z = 652.29($C_{49}H_{36}N_2$ = 652.82) | P-102 | m/z = 702.30($C_{53}H_{38}N_2$ = 702.88) |
| P-103 | m/z = 702.30($C_{53}H_{38}N_2$ = 702.88) | P-104 | m/z = 728.32($C_{55}H_{40}N_2$ = 728.92) |
| P-105 | m/z = 844.38($C_{64}H_{48}N_2$ = 845.08) | P-106 | m/z = 590.18($C_{42}H_{26}N_2S$ = 590.73) |
| P-107 | m/z = 640.20($C_{46}H_{28}N_2S$ = 640.79) | P-108 | m/z = 640.20($C_{46}H_{28}N_2S$ = 640.79) |

TABLE 5-continued

| Compound | FD-MS | Compound | FD-MS |
|---|---|---|---|
| P-109 | m/z = 690.21($C_{50}H_{30}N_2S$ = 690.85) | P = 110 | m/z = 740.23($C_{54}H_{32}N_2S$ = 740.91) |
| P-111 | m/z = 514.15($C_{36}H_{22}N_2S$ = 514.64) | P = 112 | m/z = 564.17($C_{40}H_{24}N_2S$ = 564.70) |
| P-113 | m/z = 564.17($C_{40}H_{24}N_2S$ = 564.70) | P = 114 | m/z = 614.18($C_{44}H_{26}N_2S$ = 614.76) |
| P-115 | m/z = 664.20($C_{48}H_{28}N_2S$ = 664.81) | P = 116 | m/z = 590.18($C_{42}H_{26}N_2S$ = 590.73) |
| P-117 | m/z = 640.20($C_{46}H_{28}N_2S$ = 640.79) | P = 118 | m/z = 640.20($C_{46}H_{28}N_2S$ = 640.79) |
| P-119 | m/z = 690.21($C_{50}H_{30}N_2S$ = 690.85) | P-120 | m/z = 740.23($C_{54}H_{32}N_2S$ = 740.91) |
| P-121 | m/z = 514.15($C_{36}H_{22}N_2S$ = 514.64) | P-122 | m/z = 564.17($C_{40}H_{24}N_2S$ = 564.70) |
| P-123 | m/z = 564.17($C_{40}H_{24}N_2S$ = 564.70) | P-124 | m/z = 614.18($C_{44}H_{26}N_2S$ = 614.76) |
| P-125 | m/z = 664.20($C_{48}H_{28}N_2S$ = 664.81) | P-126 | m/z = 574.20($C_{42}H_{26}N_2O$ = 574.67) |
| P-127 | m/z = 624.22($C_{46}H_{28}N_2O$ = 624.73) | P-128 | m/z = 624.22($C_{46}H_{28}N_2O$ = 624.73) |
| P-129 | m/z = 674.24($C_{50}H_{30}N_2O$ = 674.79) | P-130 | m/z = 724.25($C_{54}H_{32}N_2O$ = 724.84) |
| P-131 | m/z = 524.23($C_{39}H_{28}N_2$ = 524.65) | P-132 | m/z = 574.24($C_{43}H_{30}N_2$ = 574.71) |
| P-133 | m/z = 574.24($C_{43}H_{30}N_2$ = 574.7) | P-134 | m/z = 624.26($C_{47}H_{32}N_2$ = 624.77) |
| P-135 | m/z = 674.27($C_{51}H_{34}N_2$ = 674.83) | P-136 | m/z = 600.26($C_{45}H_{32}N_2$ = 600.75) |
| P-137 | m/z = 650.27($C_{49}H_{34}N_2$ = 650.81) | P-138 | m/z = 650.27($C_{49}H_{34}N_2$ = 650.81) |
| P-139 | m/z = 700.29($C_{53}H_{36}N_2$ = 700.87) | P-140 | m/z = 750.30($C_{57}H_{38}N_2$ = 750.93) |
| P-141 | m/z = 498.17($C_{36}H_{27}N_2O$ = 498.57) | P-142 | m/z = 548.19($C_{40}H_{24}N_2O$ = 548.63) |
| P-143 | m/z = 548.19($C_{40}H_{24}N_2O$ = 548.63) | P-144 | m/z = 598.20($C_{44}H_{26}N_2O$ = 598.69) |
| P-145 | m/z = 648.22($C_{48}H_{28}N_2O$ = 648.75) | P-146 | m/z = 642.21($C_{46}H_{30}N_2S$ = 642.81) |
| P-147 | m/z = 769.26($C_{55}H_{35}N_3S$ = 769.95) | P-148 | m/z = 844.29($C_{62}H_{40}N_2S$ = 845.06) |
| P-149 | m/z = 884.32($C_{65}H_{44}N_2S$ = 885.12) | P-150 | m/z = 834.31($C_{61}H_{42}N_2S$ = 835.06) |
| P-151 | m/z = 642.21($C_{46}H_{30}N_2S$ = 642.81) | P-152 | m/z = 769.26($C_{55}H_{35}N_3S$ = 769.95) |
| P-153 | m/z = 844.29($C_{62}H_{40}N_2S$ = 845.06) | P-154 | m/z = 884.32($C_{65}H_{44}N_2S$ = 885.12) |
| P-155 | m/z = 834.31($C_{61}H_{42}N_2S$ = 835.06) | P-156 | m/z = 626.24($C_{46}H_{30}N_2O$ = 626.74) |
| P-157 | m/z = 753.28($C_{55}H_{35}N_3O$ = 753.89) | P-158 | m/z = 828.31($C_{62}H_{40}N_2O$ = 828.99) |
| P-159 | m/z = 868.35($C_{65}H_{44}N_2O$ = 869.06) | P-160 | m/z = 818.33($C_{61}H_{42}N_2O$ = 819.00) |
| P-161 | m/z = 652.29($C_{49}H_{36}N_2$ = 652.82) | P-162 | m/z = 779.33($C_{58}H_{41}N_3$ = 779.97) |
| P-163 | m/z = 854.37($C_{65}H_{46}N_2$ = 855.07) | P-164 | m/z = 894.40($C_{68}H_{50}N_2$ = 895.14) |
| P-165 | m/z = 844.38($C_{64}H_{48}N_2$ = 845.08) | | |

Fabrication and Evaluation of Organic Electronic Element

EXAMPLE 1

Red Organic Light Emitting Diode (a Phosphorescent Red Host)

Organic light emitting diodes (OLEDs) were fabricated according to a conventional method by using a compound of the present invention as a phosphorescent host material. First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 20 nm on the hole injection layer to form a hole transport layer. Subsequently, a light emitting layer with a thickness of 30 nm was deposited on the hole transport layer by doping the hole transport layer with the compound P-26 of the present invention as a host material and bis-(1-phenylisoquinolyl)iridium(III)acetylacetonate (hereinafter abbreviated as "(piq)$_2$Ir(acac)") as a dopant material in a weight ratio of 95:5. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alg$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

EXAMPLE 2 to EXAMPLE 65

Red Organic Light Emitting Diode (a Phosphorescent Red Host)

The OLED was manufactured in the same manner as described in Example 1, except that any one of the compounds P-27 to P-90 of the present invention in the Table 6 below was used as the host material of the a light emitting layer, instead of the inventive compound P-26.

COMPARATIVE EXAMPLE 1

An OLED was manufactured in the same manner as described in Example 1, except that Comparative Compound 1 represented below was used as the host material of the a light emitting layer, instead of the inventive compound P-26.

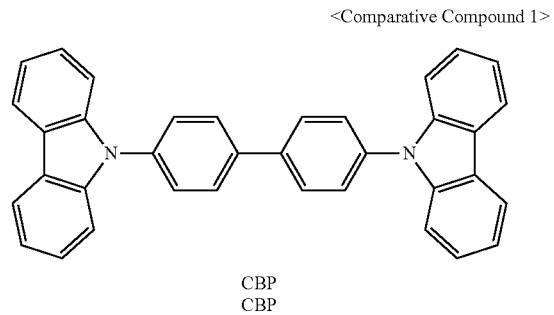

<Comparative Compound 1>

CBP
CBP

COMPARATIVE EXAMPLE 2

An OLED was manufactured in the same manner as described in Example 1, except that Comparative Compound 2 represented below was used as the host material of the a light emitting layer, instead of the inventive compound P-26.

<Comparative Compound 2>

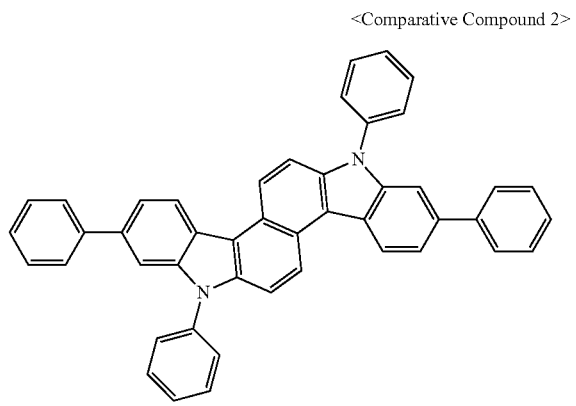 [SMILES: c1ccc(-c2ccc3c4c5ccc6c(c5ccc4n(-c4ccccc4)c3c2)c2ccc(-c3ccccc3)cc2n6-c2ccccc2)cc1]

COMPARATIVE EXAMPLE 3

An OLED was manufactured in the same manner as described in Example 1, except that Comparative Compound 3 represented below was used as the host material of the a light emitting layer, instead of the inventive compound P-26.

<Comparative Compound 3>

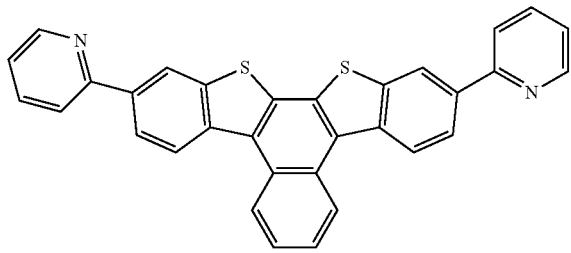

COMPARATIVE EXAMPLE 4

An OLED was manufactured in the same manner as described in Example 1, except that Comparative Compound 4 represented below was used as the host material of the a light emitting layer, instead of the inventive compound P-26.

<Comparative Compound 4>

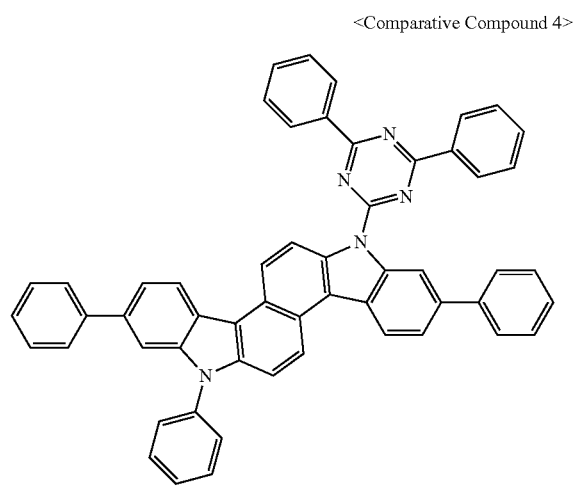 [SMILES: c1ccc(-c2ccc3c4c5ccc6c(c5ccc4n(-c4ccccc4)c3c2)c2ccc(-c3ccccc3)cc2n6-c2nc(-c3ccccc3)nc(-c3ccccc3)n2)cc1]

A forward bias DC voltage was applied to each of the OLEDs manufactured through the Examples 1 to 65 and Comparative Example 1 to 4, and electro-luminescence (EL) characteristics of the OLED were measured by PR-650 (Photoresearch). Also, T90 life span was measured by life span measuring equipment (Mcscience) at a reference brightness of 300 cd/m². Table 6 below shows evaluation results of OLEDs manufactured the Examples and Comparative Examples.

TABLE 6

|  | Compound | Voltage (V) | Current Density (mA/cm²) | Brightness (cd/m²) | Efficiency (cd/A) | Lifetime T (90) | CIE (x, y) |
|---|---|---|---|---|---|---|---|
| comp. Ex (1) | comp. Com1 | 6.5 | 6.5 | 300.0 | 4.6 | 54.2 | (0.66, 0.32) |
| comp. Ex (2) | comp. Com2 | 6.1 | 6.6 | 300.0 | 4.5 | 89.8 | (0.67, 0.32) |
| comp. Ex (3) | comp. Com3 | 6.2 | 7.4 | 300.0 | 4.1 | 83.4 | (0.66, 0.32) |
| comp. Ex (4) | comp. Com4 | 5.9 | 5.8 | 300.0 | 5.2 | 93.7 | (0.66, 0.32) |
| Ex. (1) | Com. (P-26) | 5.3 | 4.7 | 300.0 | 6.4 | 101.5 | (0.65, 0.32) |
| Ex. (2) | Com. (P-27) | 5.3 | 4.3 | 300.0 | 6.9 | 119.8 | (0.66, 0.32) |
| Ex. (3) | Com. (P-28) | 5.6 | 4.4 | 300.0 | 6.8 | 143.9 | (0.66, 0.33) |
| Ex. (4) | Com. (P-29) | 5.4 | 4.9 | 300.0 | 6.1 | 142.9 | (0.66, 0.32) |
| Ex. (5) | Com. (P-30) | 5.8 | 4.7 | 300.0 | 6.4 | 138.5 | (0.65, 0.32) |
| Ex. (6) | Com. (P-31) | 5.6 | 5.0 | 300.0 | 6.0 | 132.6 | (0.66, 0.32) |
| Ex. (7) | Com. (P-32) | 5.7 | 4.7 | 300.0 | 6.4 | 115.9 | (0.66, 0.32) |
| Ex. (8) | Com. (P-33) | 5.7 | 4.5 | 300.0 | 6.7 | 99.9 | (0.67, 0.32) |
| Ex. (9) | Com. (P-34) | 5.4 | 4.8 | 300.0 | 6.2 | 122.7 | (0.66, 0.32) |
| Ex. (10) | Com. (P-35) | 5.5 | 4.5 | 300.0 | 6.6 | 143.7 | (0.66, 0.33) |
| Ex. (11) | Com. (P-36) | 5.6 | 4.4 | 300.0 | 6.7 | 98.7 | (0.66, 0.32) |
| Ex. (12) | Com. (P-37) | 5.6 | 4.8 | 300.0 | 6.3 | 117.4 | (0.65, 0.32) |
| Ex. (13) | Com. (P-38) | 5.3 | 4.6 | 300.0 | 6.5 | 128.3 | (0.66, 0.32) |
| Ex. (14) | Com. (P-39) | 5.4 | 4.8 | 300.0 | 6.3 | 145.8 | (0.66, 0.33) |
| Ex. (15) | Com. (P-40) | 5.6 | 4.8 | 300.0 | 6.2 | 132.2 | (0.66, 0.32) |
| Ex. (16) | Com. (P-41) | 5.6 | 4.5 | 300.0 | 6.7 | 109.0 | (0.65, 0.32) |
| Ex. (17) | Com. (P-42) | 5.4 | 4.8 | 300.0 | 6.3 | 94.6 | (0.66, 0.32) |

TABLE 6-continued

| | Compound | Voltage (V) | Current Density (mA/cm$^2$) | Brightness (cd/m$^2$) | Efficiency (cd/A) | Lifetime T (90) | CIE (x, y) |
|---|---|---|---|---|---|---|---|
| Ex. (18) | Com. (P-43) | 5.4 | 4.4 | 300.0 | 6.8 | 112.1 | (0.66, 0.32) |
| Ex. (19) | Com. (P-44) | 5.5 | 4.3 | 300.0 | 6.9 | 133.9 | (0.66, 0.32) |
| Ex. (20) | Com. (P-45) | 5.4 | 4.7 | 300.0 | 6.4 | 135.3 | (0.67, 0.32) |
| Ex. (21) | Com. (P-46) | 5.5 | 4.6 | 300.0 | 6.6 | 116.0 | (0.66, 0.32) |
| Ex. (22) | Com. (P-47) | 5.8 | 4.3 | 300.0 | 7.0 | 137.8 | (0.66, 0.33) |
| Ex. (23) | Com. (P-48) | 5.5 | 4.8 | 300.0 | 6.3 | 127.7 | (0.66, 0.32) |
| Ex. (24) | Com. (P-49) | 5.6 | 4.5 | 300.0 | 6.6 | 109.3 | (0.65, 0.32) |
| Ex. (25) | Com. (P-50) | 5.7 | 4.3 | 300.0 | 6.9 | 119.1 | (0.66, 0.32) |
| Ex. (26) | Com. (P-51) | 5.5 | 4.9 | 300.0 | 6.1 | 90.2 | (0.66, 0.33) |
| Ex. (27) | Com. (P-52) | 5.8 | 4.9 | 300.0 | 6.2 | 124.7 | (0.66, 0.32) |
| Ex. (28) | Com. (P-53) | 5.5 | 4.4 | 300.0 | 6.8 | 124.0 | (0.65, 0.32) |
| Ex. (29) | Com. (P-54) | 5.7 | 4.9 | 300.0 | 6.1 | 149.1 | (0.66, 0.32) |
| Ex. (30) | Com. (P-55) | 5.4 | 4.4 | 300.0 | 6.8 | 135.5 | (0.66, 0.32) |
| Ex. (31) | Com. (P-56) | 5.7 | 4.6 | 300.0 | 6.5 | 106.6 | (0.67, 0.32) |
| Ex. (32) | Com. (P-57) | 5.6 | 4.7 | 300.0 | 6.4 | 99.7 | (0.66, 0.32) |
| Ex. (33) | Com. (P-58) | 5.6 | 4.6 | 300.0 | 6.6 | 93.2 | (0.66, 0.33) |
| Ex. (34) | Com. (P-59) | 5.7 | 4.3 | 300.0 | 6.9 | 129.4 | (0.66, 0.32) |
| Ex. (35) | Com. (P-60) | 5.4 | 4.3 | 300.0 | 7.0 | 99.1 | (0.65, 0.32) |
| Ex. (36) | Com. (P-61) | 5.4 | 4.8 | 300.0 | 6.2 | 112.7 | (0.66, 0.32) |
| Ex. (37) | Com. (P-62) | 5.4 | 4.8 | 300.0 | 6.3 | 109.9 | (0.66, 0.33) |
| Ex. (38) | Com. (P-63) | 5.7 | 4.5 | 300.0 | 6.7 | 119.8 | (0.66, 0.32) |
| Ex. (39) | Com. (P-64) | 5.5 | 4.4 | 300.0 | 6.8 | 140.2 | (0.65, 0.32) |
| Ex. (40) | Com. (P-65) | 5.5 | 5.0 | 300.0 | 6.0 | 127.6 | (0.66, 0.32) |
| Ex. (41) | Com. (P-66) | 5.9 | 5.0 | 300.0 | 6.0 | 107.9 | (0.66, 0.32) |
| Ex. (42) | Com. (P-67) | 5.9 | 5.4 | 300.0 | 5.6 | 120.7 | (0.66, 0.32) |
| Ex. (43) | Com. (P-68) | 6.0 | 5.5 | 300.0 | 5.5 | 96.5 | (0.67, 0.32) |
| Ex. (44) | Com. (P-69) | 6.0 | 5.0 | 300.0 | 6.0 | 127.9 | (0.66, 0.32) |
| Ex. (45) | Com. (P-70) | 6.0 | 6.0 | 300.0 | 5.0 | 92.6 | (0.66, 0.33) |
| Ex. (46) | Com. (P-71) | 5.9 | 5.7 | 300.0 | 5.3 | 123.5 | (0.66, 0.32) |
| Ex. (47) | Com. (P-72) | 5.9 | 5.3 | 300.0 | 5.6 | 102.7 | (0.65, 0.32) |
| Ex. (48) | Com. (P-73) | 5.9 | 5.2 | 300.0 | 5.8 | 143.9 | (0.66, 0.32) |
| Ex. (49) | Com. (P-74) | 6.0 | 5.6 | 300.0 | 5.3 | 108.9 | (0.66, 0.33) |
| Ex. (50) | Com. (P-75) | 6.0 | 5.2 | 300.0 | 5.7 | 118.2 | (0.66, 0.32) |
| Ex. (51) | Com. (P-76) | 5.9 | 5.1 | 300.0 | 5.9 | 140.9 | (0.65, 0.32) |
| Ex. (52) | Com. (P-77) | 5.8 | 5.8 | 300.0 | 5.1 | 108.1 | (0.66, 0.32) |
| Ex. (53) | Com. (P-78) | 5.8 | 5.3 | 300.0 | 5.6 | 94.9 | (0.66, 0.32) |
| Ex. (54) | Com. (P-79) | 6.0 | 5.3 | 300.0 | 5.6 | 97.6 | (0.67, 0.32) |
| Ex. (55) | Com. (P-80) | 5.9 | 5.6 | 300.0 | 5.4 | 106.1 | (0.66, 0.32) |
| Ex. (56) | Com. (P-81) | 5.9 | 6.0 | 300.0 | 5.0 | 128.2 | (0.66, 0.33) |
| Ex. (57) | Com. (P-82) | 6.0 | 5.3 | 300.0 | 5.7 | 97.9 | (0.66, 0.32) |
| Ex. (58) | Com. (P-83) | 5.8 | 5.1 | 300.0 | 5.8 | 112.2 | (0.65, 0.32) |
| Ex. (59) | Com. (P-84) | 5.9 | 5.0 | 300.0 | 6.0 | 121.1 | (0.66, 0.32) |
| Ex. (60) | Com. (P-85) | 5.9 | 5.1 | 300.0 | 5.9 | 127.4 | (0.66, 0.33) |
| Ex. (61) | Com. (P-86) | 5.9 | 5.0 | 300.0 | 6.0 | 117.9 | (0.66, 0.32) |
| Ex. (62) | Com. (P-87) | 5.8 | 5.0 | 300.0 | 6.0 | 107.9 | (0.65, 0.32) |
| Ex. (63) | Com. (P-88) | 5.9 | 5.4 | 300.0 | 5.6 | 120.7 | (0.66, 0.32) |
| Ex. (64) | Com. (P-89) | 6.0 | 5.5 | 300.0 | 5.5 | 96.5 | (0.66, 0.32) |
| Ex. (65) | Com. (P-90) | 5.9 | 5.0 | 300.0 | 6.0 | 127.9 | (0.66, 0.32) |

As is apparent from the data of Table 6, the organic electroluminescent device using the material of the present invention in a red light emitting layer has a significant improvement in luminous efficiency, longevity, and color purity. In particular, when a comparison is made between the compounds of the present invention and Comparative Compounds 2 and 3, which are similar in structure to the compounds of the present invention, the device using the quinazoline-substituted compound according to the present invention exhibited higher luminous efficiency and a longer lifespan than those using the Comparative Compounds.

EXAMPLE 66

Green Organic Light Emitting Diode (a Phosphorescent Green Host)

Organic light emitting diodes (OLEDs) were fabricated according to a conventional method by using a compound of the present invention as a phosphorescent host material. First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Subsequently, a light emitting layer with a thickness of 30 nm was deposited on the hole transport layer by doping the hole transport layer with the compound P-1 of the present invention as a host material and tris(2-phenylpyridine)-iridium (hereinafter abbreviated as "Ir(ppy)$_3$") as a dopant material in a weight ratio of 95:5. Next, a film of BAlq was vacuum-deposited with a thickness of 10 nm on the light emitting layer to form a hole blocking layer, and a film of Alq$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

EXAMPLE 67 To EXAMPLE 125

Green Organic Light Emitting Diode (a Phosphorescent Green Host)

The OLED was manufactured in the same manner as described in Example 1, except that any one of the compounds P-2 to P-20, and P-106 to P-145 of the present invention in the Table 7 below was used as the host material of the a light emitting layer, instead of the inventive compound P-1.

COMPARATIVE EXAMPLE 5

An OLED was manufactured in the same manner as described in Example 66, except that Comparative Compound 1 represented above was used as the host material of the a light emitting layer, instead of the inventive compound P-1.

COMPARATIVE EXAMPLE 6

An OLED was manufactured in the same manner as described in Example 66, except that Comparative Compound 2 represented above was used as the host material of the a light emitting layer, instead of the inventive compound P-1.

COMPARATIVE EXAMPLE 7

An OLED was manufactured in the same manner as described in Example 66, except that Comparative Compound 3 represented above was used as the host material of the a light emitting layer, instead of the inventive compound P-1.

COMPARATIVE EXAMPLE 8

An OLED was manufactured in the same manner as described in Example 66, except that Comparative Compound 4 represented above was used as the host material of the a light emitting layer, instead of the inventive compound P-1.

A forward bias DC voltage was applied to each of the OLEDs manufactured through the Examples 66 to 125 and Comparative Example 5 to 8, and electro-luminescence (EL) characteristics of the OLED were measured by PR-650 (Photoresearch). Also, T90 life span was measured by life span measuring equipment (Mcscience) at a reference brightness of 300 cd/m$^2$. Table 7 below shows evaluation results of OLEDs manufactured the Examples and Comparative Examples.

TABLE 7

|  | Compound | Voltage (V) | Current Density (mA/cm$^2$) | Brightness (cd/m$^2$) | Efficiency (cd/A) | Lifetime T (90) | CIE (x, y) |
| --- | --- | --- | --- | --- | --- | --- | --- |
| comp. Ex (5) | comp. Com1 | 6.3 | 7.7 | 300.0 | 3.9 | 60.3 | (0.31, 0.60) |
| comp. Ex (6) | comp. Com2 | 5.9 | 7.8 | 300.0 | 3.8 | 62.5 | (0.32, 0.61) |
| comp. Ex (7) | comp. Com3 | 5.8 | 6.8 | 300.0 | 4.4 | 55.7 | (0.31, 0.61) |
| comp. Ex (8) | comp. Com4 | 5.6 | 6.1 | 300.0 | 4.9 | 70.1 | (0.32, 0.61) |
| Ex. (66) | Com. (P-1) | 5.3 | 5.6 | 300.0 | 5.4 | 131.1 | (0.33, 0.61) |
| Ex. (67) | Com. (P-2) | 5.5 | 4.8 | 300.0 | 6.3 | 137.8 | (0.33, 0.60) |
| Ex. (68) | Com. (P-3) | 5.3 | 5.0 | 300.0 | 6.0 | 110.5 | (0.33, 0.60) |
| Ex. (69) | Com. (P-4) | 5.5 | 5.8 | 300.0 | 5.2 | 99.1 | (0.31, 0.61) |
| Ex. (70) | Com. (P-5) | 5.3 | 4.8 | 300.0 | 6.2 | 130.8 | (0.31, 0.60) |
| Ex. (71) | Com. (P-6) | 5.5 | 5.1 | 300.0 | 5.9 | 107.7 | (0.33, 0.61) |
| Ex. (72) | Com. (P-7) | 5.3 | 5.8 | 300.0 | 5.2 | 123.3 | (0.32, 0.60) |
| Ex. (73) | Com. (P-8) | 5.3 | 5.6 | 300.0 | 5.4 | 133.3 | (0.32, 0.61) |
| Ex. (74) | Com. (P-9) | 5.3 | 4.8 | 300.0 | 6.2 | 135.0 | (0.33, 0.60) |
| Ex. (75) | Com. (P-10) | 5.5 | 4.9 | 300.0 | 6.1 | 134.7 | (0.30, 0.60) |
| Ex. (76) | Com. (P-11) | 5.3 | 4.6 | 300.0 | 6.5 | 105.1 | (0.30, 0.61) |
| Ex. (77) | Com. (P-12) | 5.4 | 5.9 | 300.0 | 5.1 | 125.4 | (0.32, 0.61) |
| Ex. (78) | Com. (P-13) | 5.4 | 5.1 | 300.0 | 5.8 | 97.6 | (0.31, 0.61) |
| Ex. (79) | Com. (P-14) | 5.4 | 5.3 | 300.0 | 5.7 | 117.6 | (0.31, 0.60) |
| Ex. (80) | Com. (P-15) | 5.5 | 4.9 | 300.0 | 6.1 | 123.5 | (0.31, 0.61) |
| Ex. (81) | Com. (P-16) | 5.3 | 5.1 | 300.0 | 5.9 | 91.4 | (0.32, 0.61) |
| Ex. (82) | Com. (P-17) | 5.4 | 5.0 | 300.0 | 6.0 | 96.2 | (0.31, 0.61) |
| Ex. (83) | Com. (P-18) | 5.4 | 5.1 | 300.0 | 5.9 | 114.4 | (0.33, 0.60) |
| Ex. (84) | Com. (P-19) | 5.3 | 4.7 | 300.0 | 6.3 | 124.2 | (0.31, 0.61) |
| Ex. (85) | Com. (P-20) | 5.5 | 4.8 | 300.0 | 6.3 | 127.7 | (0.32, 0.61) |
| Ex. (86) | Com. (P-106) | 5.6 | 4.5 | 300.0 | 6.7 | 135.0 | (0.31, 0.60) |
| Ex. (87) | Com. (P-107) | 5.5 | 4.8 | 300.0 | 6.3 | 119.0 | (0.32, 0.61) |
| Ex. (88) | Com. (P-108) | 5.6 | 4.8 | 300.0 | 6.2 | 101.1 | (0.31, 0.61) |
| Ex. (89) | Com. (P-109) | 5.3 | 5.2 | 300.0 | 5.8 | 124.5 | (0.33, 0.61) |
| Ex. (90) | Com. (P-110) | 5.5 | 4.7 | 300.0 | 6.4 | 115.8 | (0.33, 0.60) |
| Ex. (91) | Com. (P-111) | 5.5 | 4.8 | 300.0 | 6.2 | 116.4 | (0.33, 0.61) |
| Ex. (92) | Com. (P-112) | 5.3 | 4.5 | 300.0 | 6.7 | 104.2 | (0.31, 0.61) |
| Ex. (93) | Com. (P-113) | 5.5 | 5.8 | 300.0 | 5.2 | 146.8 | (0.31, 0.61) |
| Ex. (94) | Com. (P-114) | 5.5 | 5.8 | 300.0 | 5.2 | 99.5 | (0.33, 0.61) |
| Ex. (95) | Com. (P-115) | 5.5 | 5.7 | 300.0 | 5.2 | 107.0 | (0.32, 0.60) |
| Ex. (96) | Com. (P-116) | 5.5 | 4.6 | 300.0 | 6.5 | 149.6 | (0.32, 0.61) |
| Ex. (97) | Com. (P-117) | 5.4 | 5.6 | 300.0 | 5.4 | 143.7 | (0.33, 0.61) |
| Ex. (98) | Com. (P-118) | 5.6 | 5.7 | 300.0 | 5.3 | 105.7 | (0.30, 0.60) |
| Ex. (99) | Com. (P-119) | 5.4 | 4.4 | 300.0 | 6.8 | 118.0 | (0.30, 0.61) |
| Ex. (100) | Com. (P-120) | 5.4 | 4.4 | 300.0 | 6.8 | 140.0 | (0.32, 0.61) |
| Ex. (101) | Com. (P-121) | 5.6 | 4.4 | 300.0 | 6.9 | 144.9 | (0.31, 0.61) |
| Ex. (102) | Com. (P-122) | 5.5 | 4.6 | 300.0 | 6.5 | 90.2 | (0.31, 0.60) |
| Ex. (103) | Com. (P-123) | 5.5 | 4.6 | 300.0 | 6.6 | 144.4 | (0.31, 0.61) |
| Ex. (104) | Com. (P-124) | 5.3 | 5.8 | 300.0 | 5.1 | 97.1 | (0.32, 0.61) |

TABLE 7-continued

| | Compound | Voltage (V) | Current Density (mA/cm²) | Brightness (cd/m²) | Efficiency (cd/A) | Lifetime T (90) | CIE (x, y) |
|---|---|---|---|---|---|---|---|
| Ex. (105) | Com. (P-125) | 5.6 | 4.6 | 300.0 | 6.6 | 110.7 | (0.31, 0.61) |
| Ex. (106) | Com. (P-126) | 5.4 | 5.7 | 300.0 | 5.3 | 123.2 | (0.33, 0.60) |
| Ex. (107) | Com. (P-127) | 5.6 | 4.5 | 300.0 | 6.6 | 116.8 | (0.31, 0.60) |
| Ex. (108) | Com. (P-128) | 5.4 | 5.7 | 300.0 | 5.2 | 145.1 | (0.32, 0.61) |
| Ex. (109) | Com. (P-129) | 5.5 | 4.5 | 300.0 | 6.7 | 128.4 | (0.31, 0.60) |
| Ex. (110) | Com. (P-130) | 5.4 | 4.5 | 300.0 | 6.7 | 125.8 | (0.32, 0.61) |
| Ex. (111) | Com. (P-131) | 5.4 | 4.3 | 300.0 | 7.0 | 116.3 | (0.31, 0.61) |
| Ex. (112) | Com. (P-132) | 5.3 | 5.9 | 300.0 | 5.1 | 92.7 | (0.33, 0.61) |
| Ex. (113) | Com. (P-133) | 5.5 | 4.7 | 300.0 | 6.3 | 119.6 | (0.33, 0.60) |
| Ex. (114) | Com. (P-134) | 5.6 | 4.9 | 300.0 | 6.1 | 118.7 | (0.33, 0.60) |
| Ex. (115) | Com. (P-135) | 5.4 | 4.3 | 300.0 | 7.0 | 147.3 | (0.31, 0.61) |
| Ex. (116) | Com. (P-136) | 5.6 | 4.6 | 300.0 | 6.5 | 124.6 | (0.31, 0.60) |
| Ex. (117) | Com. (P-137) | 5.5 | 4.5 | 300.0 | 6.7 | 146.9 | (0.33, 0.61) |
| Ex. (118) | Com. (P-138) | 5.5 | 5.5 | 300.0 | 5.5 | 119.5 | (0.32, 0.60) |
| Ex. (119) | Com. (P-139) | 5.4 | 4.4 | 300.0 | 6.8 | 142.9 | (0.32, 0.61) |
| Ex. (120) | Com. (P-140) | 5.4 | 4.6 | 300.0 | 6.5 | 147.0 | (0.33, 0.60) |
| Ex. (121) | Com. (P-141) | 5.4 | 5.3 | 300.0 | 5.7 | 139.1 | (0.30, 0.60) |
| Ex. (122) | Com. (P-142) | 5.6 | 4.6 | 300.0 | 6.5 | 107.3 | (0.30, 0.61) |
| Ex. (123) | Com. (P-143) | 5.4 | 5.2 | 300.0 | 5.8 | 93.7 | (0.32, 0.61) |
| Ex. (124) | Com. (P-144) | 5.4 | 5.6 | 300.0 | 5.3 | 134.2 | (0.31, 0.61) |
| Ex. (125) | Com. (P-145) | 5.4 | 5.7 | 300.0 | 5.3 | 116.0 | (0.31, 0.60) |

As is apparent from the data of Table 7, the organic electroluminescent device using the material of the present invention in a green light emitting layer has a significant improvement in luminous efficiency, longevity, and color purity. In particular, when a comparison is made between the compounds of the present invention and Comparative Compounds 2 and 3, which are similar in structure to the compounds of the present invention, the device using the compound according to the present invention exhibited higher luminous efficiency and a longer lifespan than those using the Comparative Compounds.

EXAMPLE 126

Green Organic Light Emitting Diode (Emission-Auxiliary Layer)

Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Next, the inventive compound P-21 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 4,4'-N,N'-dicarbazole-biphenyl ((hereinafter abbreviated as "CBP") as a host material and Ir(ppy)$_3$ as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

EXAMPLE 127 to EXAMPLE 130

Green Organic Light Emitting Diode (Emission-Auxiliary Layer)

The OLED was manufactured in the same manner as described in Example 126, except that any one of the compounds P-22 to P-25 of the present invention in the Table 8 below was used as the material of a Emission-Auxiliary layer, instead of the inventive compound P-21.

COMPARATIVE EXAMPLE 9

An OLED was manufactured in the same manner as described in Example 126, except that a Emission-Auxiliary layer was not formed.

COMPARATIVE EXAMPLE 10

An OLED was manufactured in the same manner as described in Example 126, except that Comparative Compound 5 represented below was used as the material of a Emission-Auxiliary layer, instead of the inventive compound P-21.

<Comparative Compound 5>

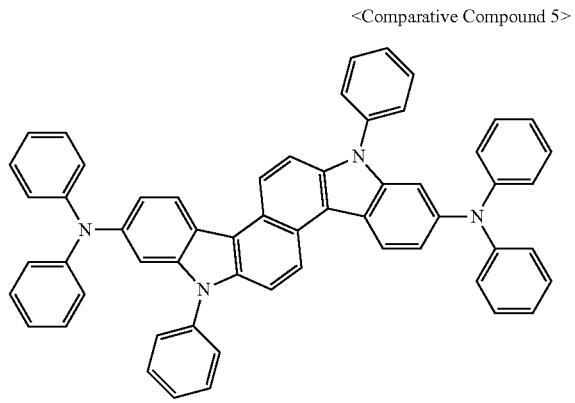 [SMILES: c1ccc(N(c2ccccc2)c2ccc3c4c5ccc6c(c5ccc4n(-c4ccccc4)c3c2)c2ccc(N(c3ccccc3)c3ccccc3)cc2n6-c2ccccc2)cc1]

COMPARATIVE EXAMPLE 11

An OLED was manufactured in the same manner as described in Example 126, except that Comparative Compound 6 represented below was used as the material of a Emission-Auxiliary layer, instead of the inventive compound P-21.

<Comparative Compound 6>

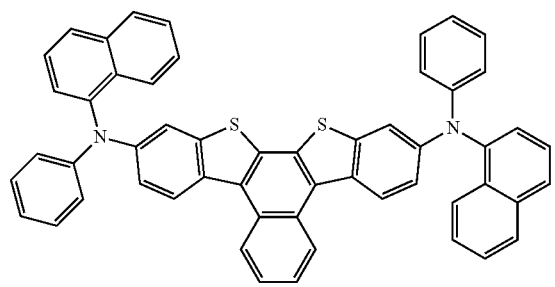

A forward bias DC voltage was applied to each of the OLEDs manufactured through the Examples 126 to 130 and Comparative Examples 9 to 11, and electro-luminescence (EL) characteristics of the OLED were measured by PR-650 (Photoresearch). Also, T90 life span was measured by life span measuring equipment (Mcscience) at a reference brightness of 300 cd/m$^2$. Table 8 below shows evaluation results of OLEDs manufactured the Examples and Comparative Examples.

EXAMPLE 131

Green Organic Light Emitting Diode (a Hole Transport Layer)

Organic light emitting diodes (OLEDs) were fabricated according to a conventional method by using a compound of the present invention as a hole transport layer material. First, an ITO layer (anode) was formed on a glass substrate, and a film of 2-TNATA was vacuum-deposited on the ITO layer to form a hole injection layer with a thickness of 60 nm. Subsequently, a film of the compound P-91 of the present invention was vacuum-deposited on the hole injection layer to form a hole transport layer with a thickness of 20 nm. Subsequently, a light emitting layer with a thickness of 30 nm was deposited on the hole transport layer by doping the hole transport layer with the CBP as a host material and Ir(ppy)$_3$ as a dopant material in a weight ratio of 90:10. Next, a film of BAlq was vacuum-deposited with a thickness of 10 nm on the light emitting layer to form a hole blocking layer, and a film of Alg$_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

TABLE 8

| | Compound | Voltage (V) | Current Density (mA/cm$^2$) | Brightness (cd/m2) | Efficiency (cd/A) | Lifetime T (90) | CIE (x, y) |
|---|---|---|---|---|---|---|---|
| comp. Ex (9) | — | 6.3 | 9.0 | 300.0 | 3.3 | 62.8 | (0.66, 0.32) |
| comp. Ex (10) | comp. Com 4 | 6.2 | 8.0 | 300.0 | 3.8 | 76.3 | (0.67, 0.32) |
| comp. Ex (11) | comp. Com 5 | 6.2 | 8.5 | 300.0 | 3.5 | 58.2 | (0.66, 0.32) |
| Ex. (126) | Com. (P-21) | 5.8 | 6.5 | 300.0 | 4.6 | 139.7 | (0.66, 0.33) |
| Ex. (127) | Com. (P-22) | 5.9 | 7.3 | 300.0 | 4.1 | 104.2 | (0.66, 0.32) |
| Ex. (128) | Com. (P-23) | 5.9 | 6.1 | 300.0 | 4.9 | 127.5 | (0.65, 0.32) |
| Ex. (129) | Com. (P-24) | 5.8 | 6.0 | 300.0 | 5.0 | 125.3 | (0.66, 0.32) |
| Ex. (130) | Com. (P-25) | 5.8 | 6.3 | 300.0 | 4.8 | 100.4 | (0.66, 0.33) |

As can be seen from the data of Table 8, a device using the compound of the present invention in the auxiliary light emitting layer was reduced in driving voltage and significantly increased in longevity, compared to that using no auxiliary light emitting layers, or using Comparative Compound 5 or 6 in the auxiliary light emitting layer. This can be accounted for by the fact that the exclusive use of the compound of the present invention in the auxiliary light emitting layer allows for a higher T1 value and a deeper HOMO energy level, thereby bringing about a reduction in driving voltage and an improvement in luminous efficiency and longevity of the device.

EXAMPLE 132 to EXAMPLE 165

Green Organic Light Emitting Diode (a Hole Transport Layer)

The OLED was manufactured in the same manner as described in Example 131, except that any one of the compounds P-92 to P-105 and P-146 to P-165 of the present invention in the Table 9 below was used as the hole transport layer material, instead of the inventive compound P-91.

COMPARATIVE EXAMPLE 12

An OLED was manufactured in the same manner as described in Example 131, except that Comparative Compound 7 represented below was used as the hole transport layer material, instead of the inventive compound P-91.

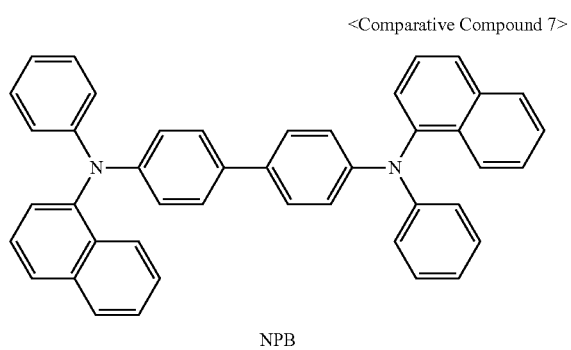 [SMILES: c1ccc(N(c2ccc(-c3ccc(N(c4ccccc4)c4cccc5ccccc45)cc3)cc2)c2cccc3ccccc23)cc1 ; "NPB"]

<Comparative Compound 7>

NPB

COMPARATIVE EXAMPLE 13

An OLED was manufactured in the same manner as described in Example 131, except that Comparative Compound 5 represented above was used as the hole transport layer material, instead of the inventive compound P-91.

COMPARATIVE EXAMPLE 14

An OLED was manufactured in the same manner as described in Example 131, except that Comparative Compound 6 represented above was used as the hole transport layer material, instead of the inventive compound P-91.

A forward bias DC voltage was applied to each of the OLEDs manufactured through the Examples 131 to 165 and Comparative Examples 12 to 14, and electro-luminescence (EL) characteristics of the OLED were measured by PR-650 (Photoresearch). Also, T90 life span was measured by life span measuring equipment (Mcscience) at a reference brightness of 300 cd/m². Table 9 below shows evaluation results of OLEDs manufactured the Examples and Comparative Examples.

TABLE 9

| | Compound | Voltage (V) | Current Density (mA/cm²) | Brightness (cd/m²) | Efficiency (cd/A) | Lifetime T (90) | CIE (x, y) |
|---|---|---|---|---|---|---|---|
| comp. Ex (12) | comp. Com 7 | 5.7 | 7.0 | 300.0 | 4.3 | 75.4 | (0.33, 0.61) |
| comp. Ex (13) | comp. Com 5 | 5.5 | 5.6 | 300.0 | 5.3 | 94.3 | (0.32, 0.60) |
| comp. Ex (14) | comp. Com 6 | 5.3 | 5.8 | 300.0 | 5.2 | 90.8 | (0.31, 0.61) |
| Ex. (131) | Com. (P-91) | 4.7 | 4.9 | 300.0 | 6.2 | 121.3 | (0.31, 0.61) |
| Ex. (132) | Com. (P-92) | 4.7 | 4.6 | 300.0 | 6.5 | 125.8 | (0.31, 0.60) |
| Ex. (133) | Com. (P-93) | 4.7 | 4.4 | 300.0 | 6.9 | 98.6 | (0.33, 0.61) |
| Ex. (134) | Com. (P-94) | 4.6 | 4.4 | 300.0 | 6.8 | 116.6 | (0.32, 0.60) |
| Ex. (135) | Com. (P-95) | 4.9 | 4.6 | 300.0 | 6.5 | 121.8 | (0.32, 0.61) |
| Ex. (136) | Com. (P-96) | 4.8 | 4.9 | 300.0 | 6.1 | 149.7 | (0.33, 0.60) |
| Ex. (137) | Com. (P-97) | 4.7 | 4.9 | 300.0 | 6.1 | 109.1 | (0.30, 0.60) |
| Ex. (138) | Com. (P-98) | 4.8 | 4.6 | 300.0 | 6.6 | 103.7 | (0.30, 0.61) |
| Ex. (139) | Com. (P-99) | 4.8 | 4.3 | 300.0 | 7.0 | 131.8 | (0.32, 0.61) |
| Ex. (140) | Com. (P-100) | 4.6 | 4.8 | 300.0 | 6.3 | 103.7 | (0.31, 0.61) |
| Ex. (141) | Com. (P-101) | 4.6 | 5.0 | 300.0 | 6.0 | 142.2 | (0.31, 0.60) |
| Ex. (142) | Com. (P-102) | 4.8 | 4.5 | 300.0 | 6.7 | 120.0 | (0.31, 0.60) |
| Ex. (143) | Com. (P-103) | 4.8 | 4.7 | 300.0 | 6.3 | 101.2 | (0.32, 0.61) |
| Ex. (144) | Com. (P-104) | 4.5 | 4.5 | 300.0 | 6.7 | 127.7 | (0.31, 0.61) |
| Ex. (145) | Com. (P-105) | 4.6 | 4.3 | 300.0 | 6.9 | 98.0 | (0.33, 0.61) |
| Ex. (146) | Com. (P-146) | 4.6 | 5.0 | 300.0 | 6.0 | 101.0 | (0.31, 0.61) |
| Ex. (147) | Com. (P-147) | 4.8 | 4.9 | 300.0 | 6.1 | 93.1 | (0.32, 0.61) |
| Ex. (148) | Com. (P-148) | 4.7 | 4.5 | 300.0 | 6.6 | 104.8 | (0.32, 0.61) |
| Ex. (149) | Com. (P-149) | 4.6 | 4.8 | 300.0 | 6.3 | 107.9 | (0.33, 0.60) |
| Ex. (150) | Com. (P-150) | 4.8 | 4.4 | 300.0 | 6.9 | 138.7 | (0.30, 0.61) |
| Ex. (151) | Com. (P-151) | 4.6 | 4.3 | 300.0 | 7.0 | 108.7 | (0.31, 0.61) |
| Ex. (152) | Com. (P-152) | 4.6 | 4.6 | 300.0 | 6.5 | 102.7 | (0.31, 0.60) |
| Ex. (153) | Com. (P-153) | 4.5 | 4.5 | 300.0 | 6.6 | 125.1 | (0.33, 0.61) |
| Ex. (154) | Com. (P-154) | 4.7 | 4.9 | 300.0 | 6.2 | 142.7 | (0.32, 0.61) |
| Ex. (155) | Com. (P-155) | 4.8 | 4.9 | 300.0 | 6.1 | 129.1 | (0.33, 0.60) |
| Ex. (156) | Com. (P-156) | 4.6 | 4.4 | 300.0 | 6.8 | 103.5 | (0.30, 0.61) |
| Ex. (157) | Com. (P-157) | 4.6 | 4.4 | 300.0 | 6.8 | 119.1 | (0.31, 0.61) |
| Ex. (158) | Com. (P-158) | 4.6 | 4.7 | 300.0 | 6.3 | 138.8 | (0.31, 0.60) |
| Ex. (159) | Com. (P-159) | 4.8 | 5.0 | 300.0 | 6.1 | 137.7 | (0.33, 0.61) |
| Ex. (160) | Com. (P-160) | 4.7 | 4.3 | 300.0 | 7.0 | 148.1 | (0.32, 0.60) |
| Ex. (161) | Com. (P-161) | 4.7 | 4.5 | 300.0 | 6.6 | 132.7 | (0.32, 0.61) |
| Ex. (162) | Com. (P-162) | 5.0 | 4.6 | 300.0 | 6.5 | 134.1 | (0.33, 0.60) |
| Ex. (163) | Com. (P-163) | 4.9 | 4.5 | 300.0 | 6.6 | 114.6 | (0.30, 0.60) |
| Ex. (164) | Com. (P-164) | 4.7 | 5.0 | 300.0 | 6.1 | 146.6 | (0.30, 0.61) |
| Ex. (165) | Com. (P-165) | 5.0 | 4.6 | 300.0 | 6.6 | 140.7 | (0.32, 0.61) |

As can be seen from the data of Table 9, when the compound of the present invention is used as a material of the hole transporting layer, the driving voltage could be reduced, and light emitting efficiency, lifespan, and color purity could be remarkably improved compared to the comparative examples. In particular, comparing the results based on the element to which the compound of the present invention was applied with those based on the elements to which Comparative Compounds 5 and 6 having a structure similar to that of the compound of the present invention were applied, it could be confirmed that the element to which the compound of the present invention was applied has higher light emitting efficiency, a longer lifespan, and a low driving voltage.

It is obvious that even though the compounds of the present invention are used in the other organic layers of the organic electrical light emitting element, for example, a hole injection layer, an electron injection layer, and an electron transporting layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

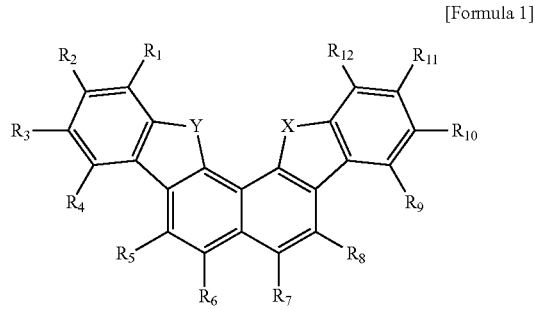

[Formula 1]

wherein,
i) $R_1$ to $R_{12}$ are independently selected from the group consisting of hydrogen, deuterium, tritium, halogen, a $C_6$-$C_{60}$ aryl group, a $C_2$-$C_{60}$ heterocyclic group containing at least one heteroatom selected from O, N, S, Si, and P, a $C_1$-$C_{60}$ alkyl group, a $C_2$-$C_{60}$ alkenyl group, a fluorenyl group, and -$L^1$-N(R')(R") or ii) any adjacent groups of $R_1$ to $R_{12}$ can be independently linked together to form at least one fused ring and any of the other $R_1$ to $R_{12}$ that don't form a fused ring is the same as defined in the above i), X and Y may be independently NR', S, O, CR'R" or SiR'R", wherein i) R' and R" are independently selected from the group consisting of a $C_6$-$C_{60}$ aryl group, a $C_2$-$C_{60}$ heterocyclic group containing at least one heteroatom selected from O, N, S, Si, and P, a fluorenyl group, a $C_1$-$C_{60}$ alkyl group and -L-N(Ar$_1$)(Ar$_2$) or ii) R' and R" can be optionally linked together to form a spiro compound with C or Si to which they are linked,
wherein L is selected from the group consisting of a single bond, a $C_6$-$C_{60}$ arylene group, a fluorenylene group, and a $C_2$-$C_{60}$ heterocyclic group containing at least one heteroatom selected from O, N, S, Si, and P and a divalent aliphatic hydrocarbon group, wherein Ar$_1$ and Ar$_2$ are independently selected from the group consisting of a $C_6$-$C_{60}$ aryl group, a fluorenyl group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, and a $C_1$-$C_{30}$ alkoxy group,
with the proviso that the aryl group, fluorenyl group, heterocyclic group, alkyl group, alkenyl group, alkoxy group, arylene group, fluorenylene group and aliphatic hydrocarbon group of Ar$_1$, Ar$_2$, L, $R_1$ to $R_{12}$, R' and R" can be optionally substituted by one or more substituents selected from the group consisting of deuterium, halogen, a silane group, a siloxane group, a boron group, a germanium group, a cyano group, a nitro group, amine group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound as claimed in claim 1, wherein the compound is represented by one of Formulas below:

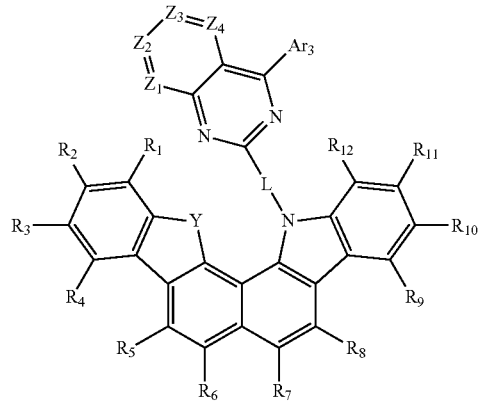

[Formula 2]

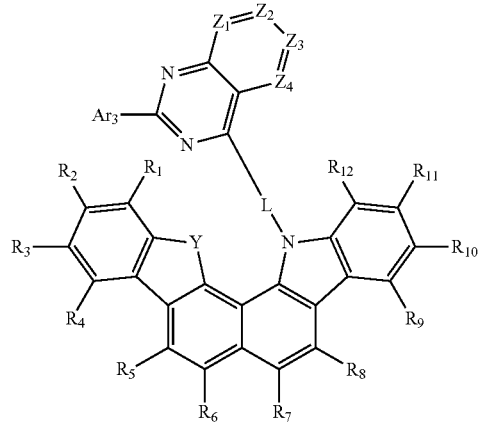

[Formula 3]

wherein,

Ar$_3$ is selected from the group consisting of a C$_6$-C$_{60}$ aryl group, a C$_2$-C$_{20}$ alkenyl group, a C$_2$-C$_{60}$ heterocyclic group containing at least one heteroatom selected from the group consisting of O, N, S, Si, and P, a C$_1$-C$_{50}$ alkyl group, and a substituted with a C$_1$-C$_{20}$ alkyl group or unsubstituted fluorenyl group, Z$_1$ to Z$_4$ are independently CR' or N, and R$_1$ to R$_{12}$, Y, L and R' are the same as defined in claim 1.

3. The compound as claimed in claim 1, being any one of the compounds below:

P-1
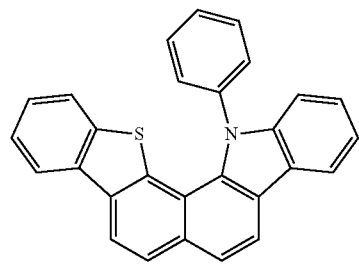

P-2
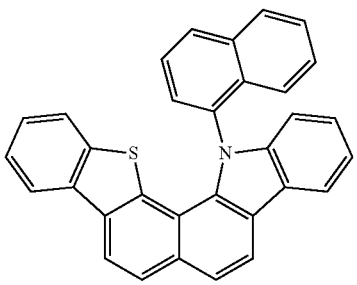

P-3
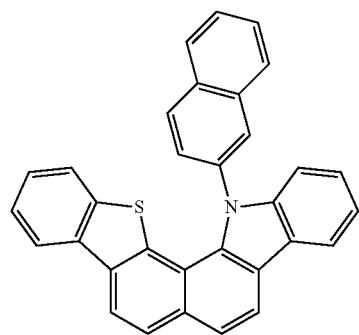

P-4
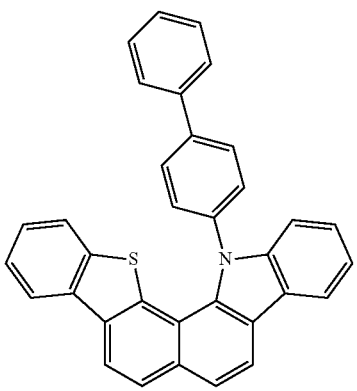

P-5
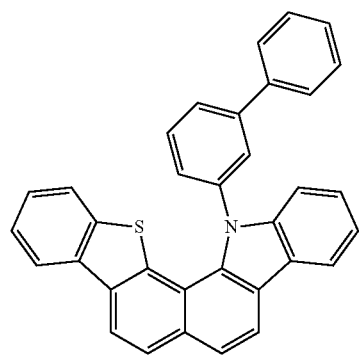

P-6
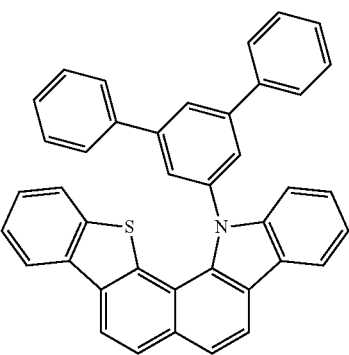

P-7
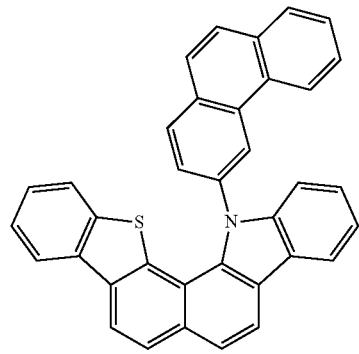

P-8
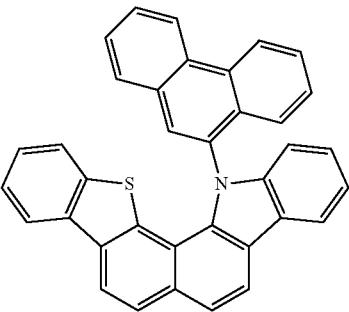

-continued
P-9
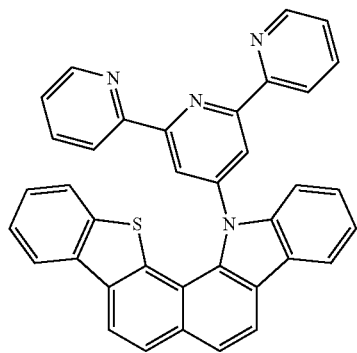
P-10
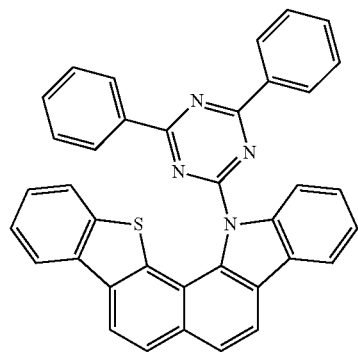
P-11
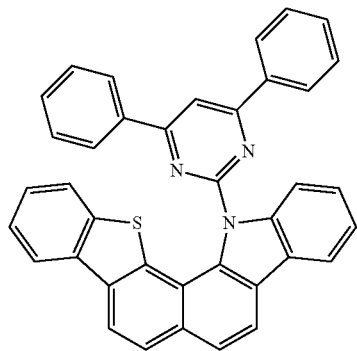
P-12
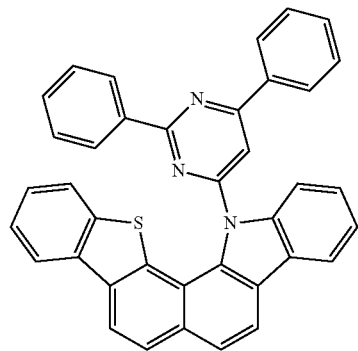
P-13
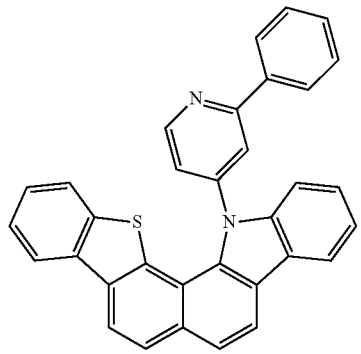
P-14
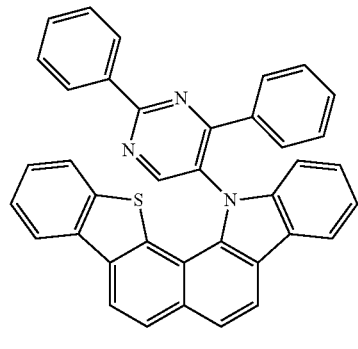
P-15
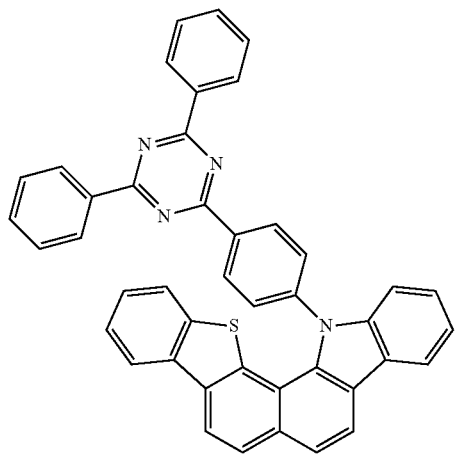
P-16
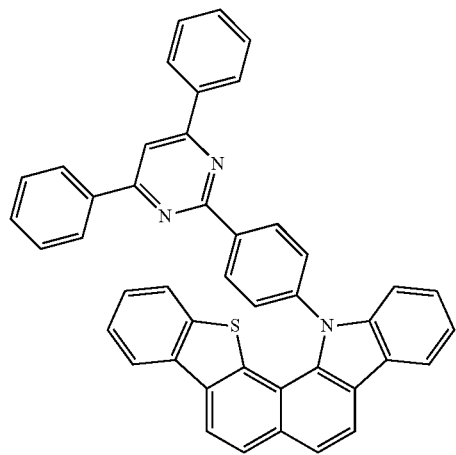

-continued
P-17
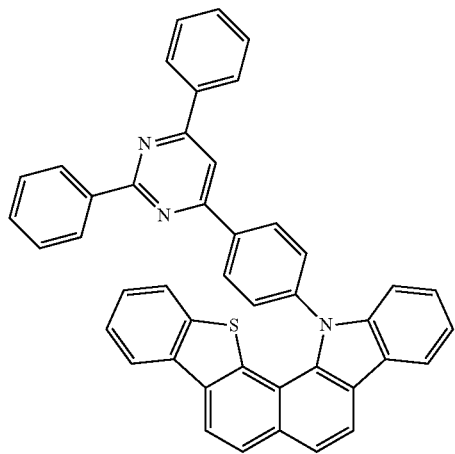
P-18
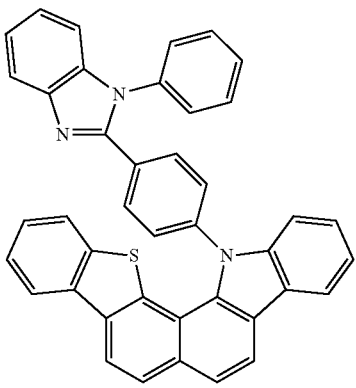
P-19
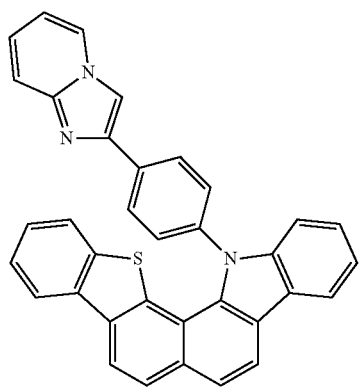
P-20
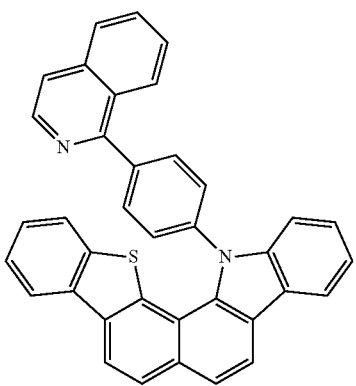
P-21
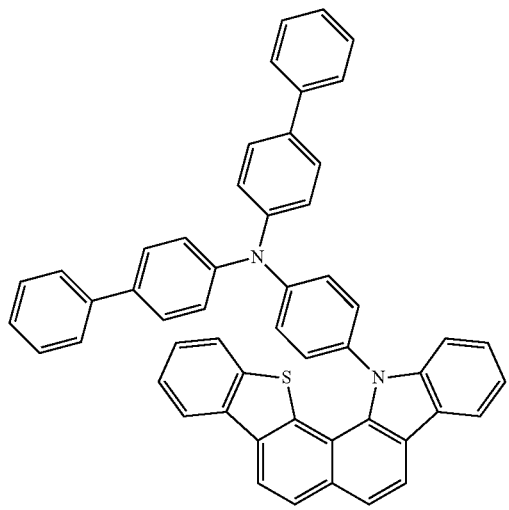
P-22
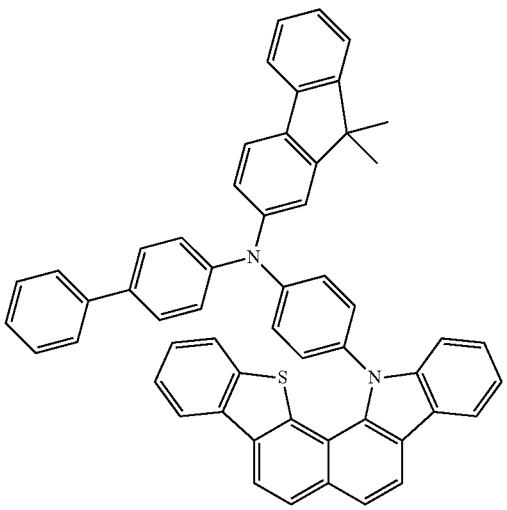

-continued
P-23
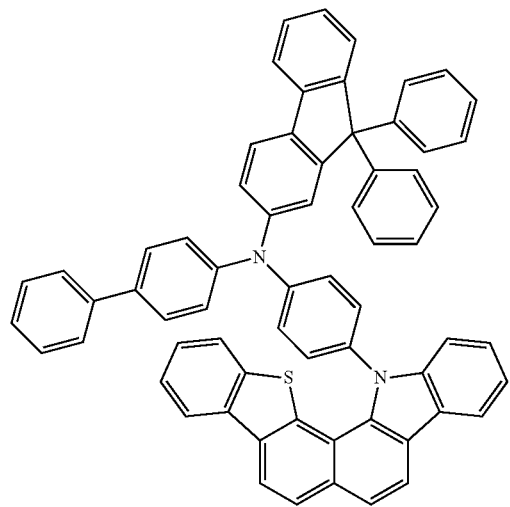
P-24
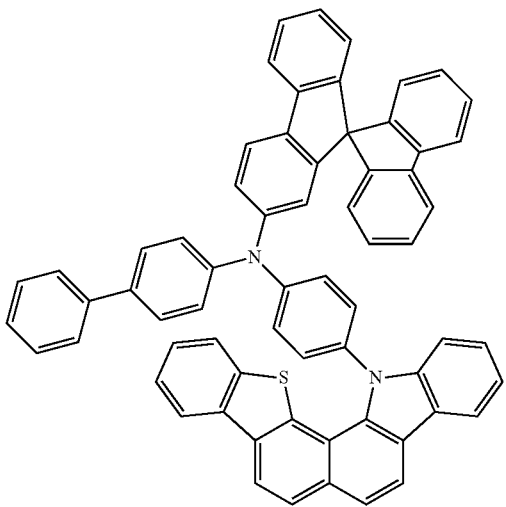
P-25
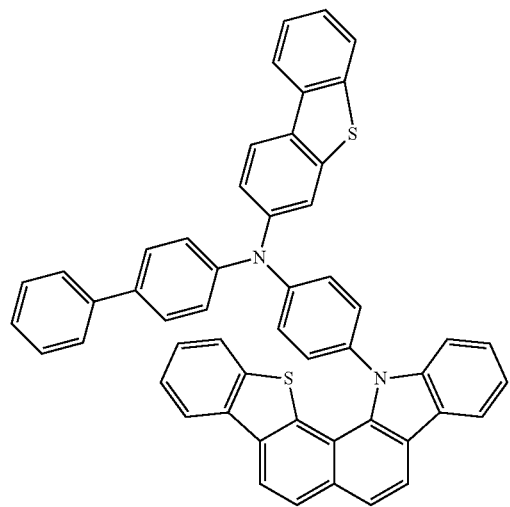
P-26
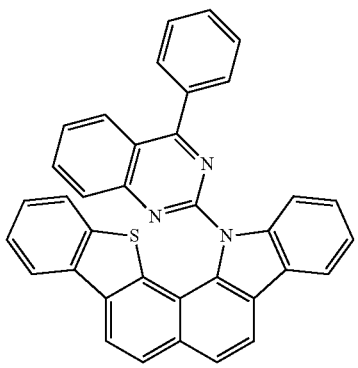
P-27
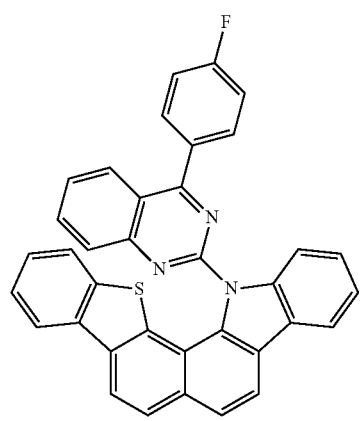
P-28
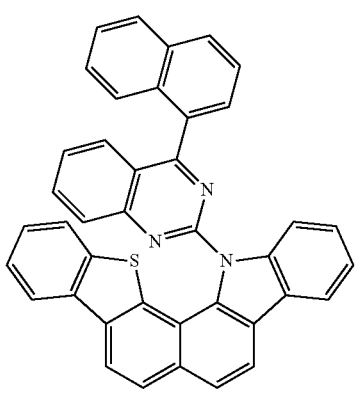

-continued
P-29
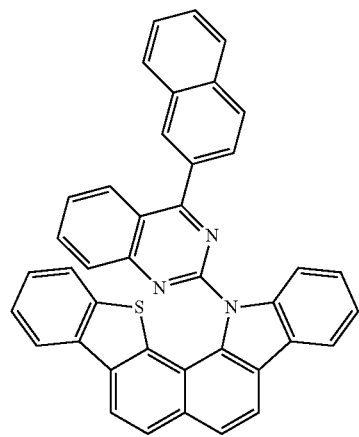
P-30
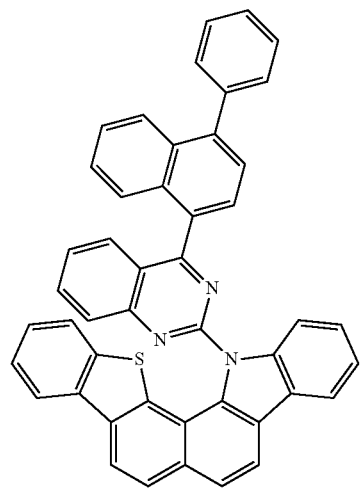
P-31
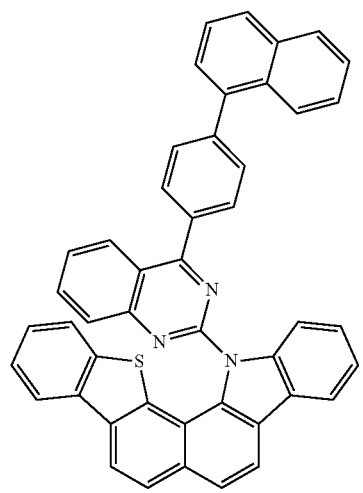
P-32
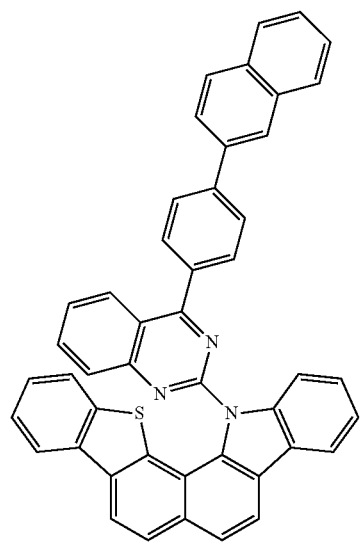
P-33
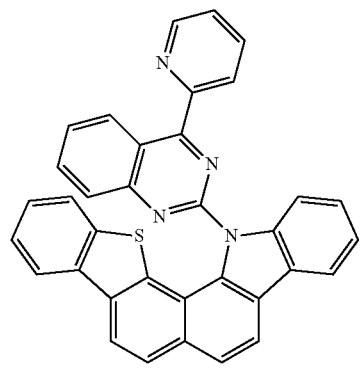
P-34
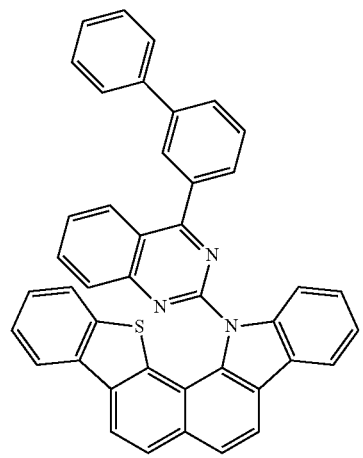

-continued
P-35
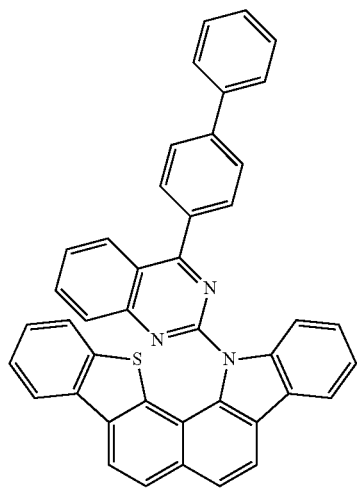
P-36
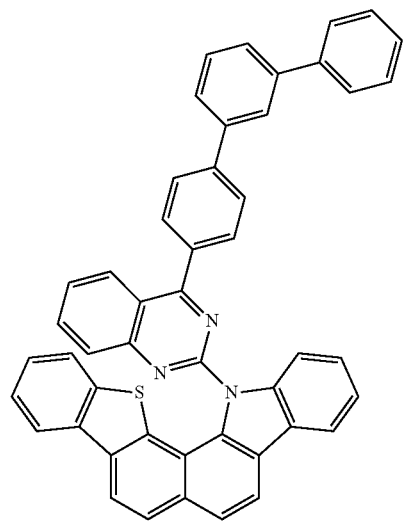
P-37
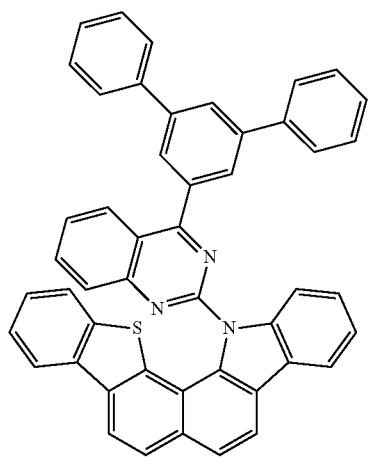
P-38
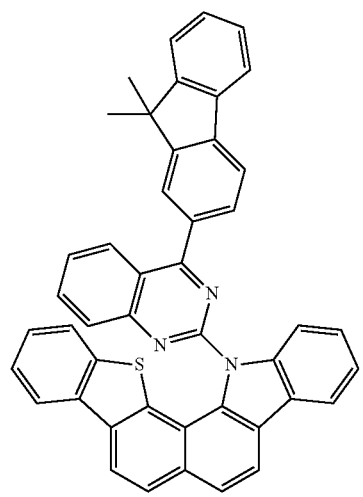
P-39
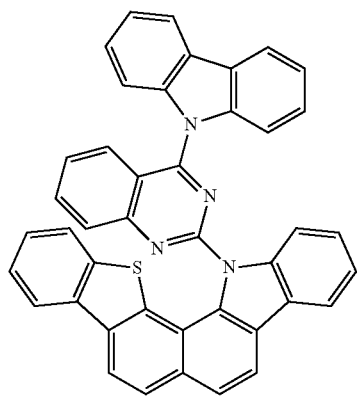
P-40
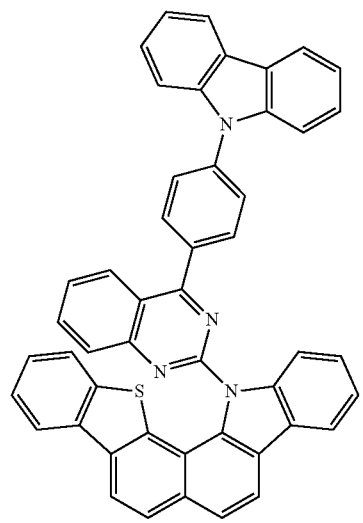

-continued
P-41
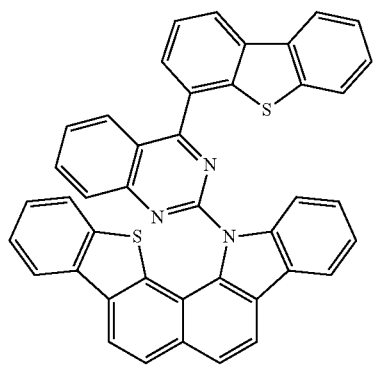
P-42
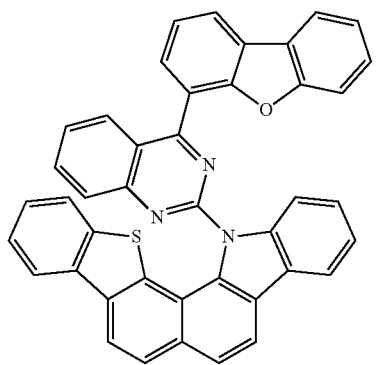
P-43
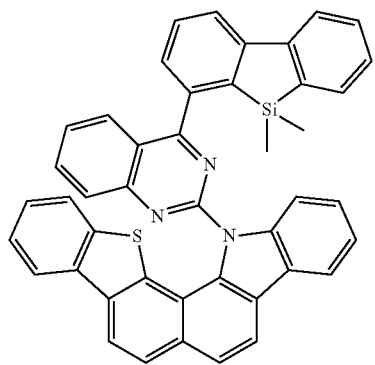
P-44
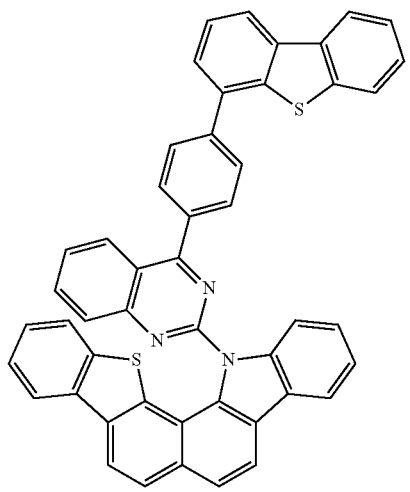
P-45
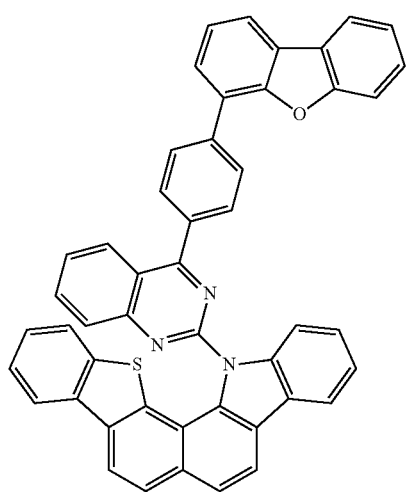
P-46
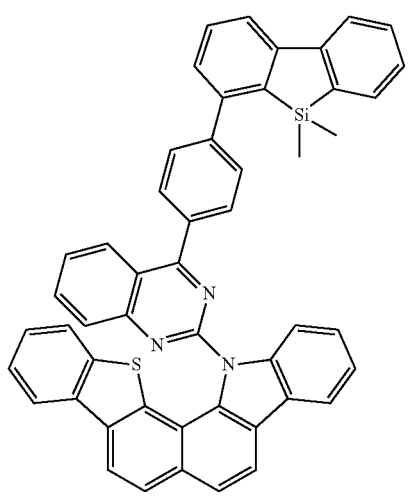

-continued
P-47
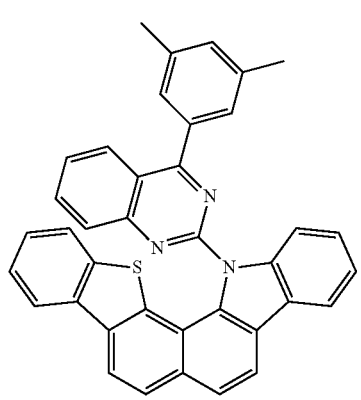
P-48
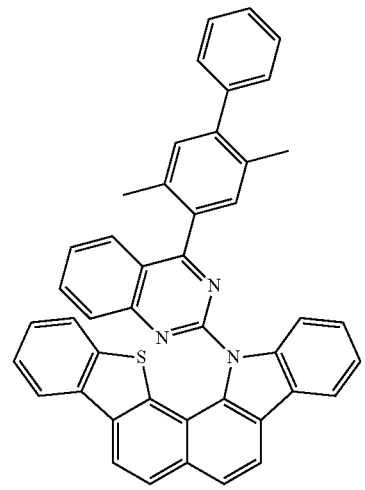
P-49
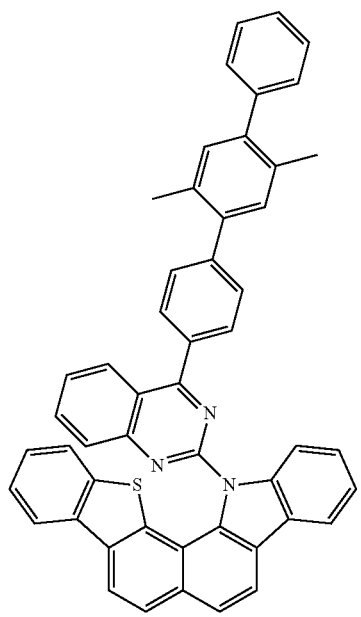
P-50
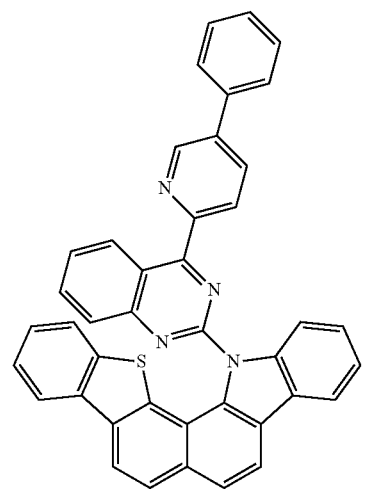
P-51
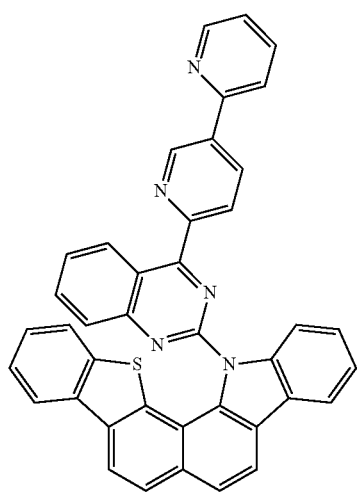
P-52
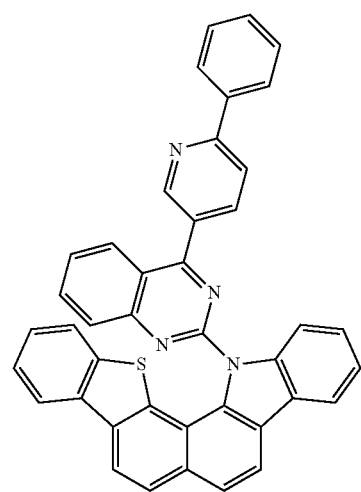

-continued
P-53
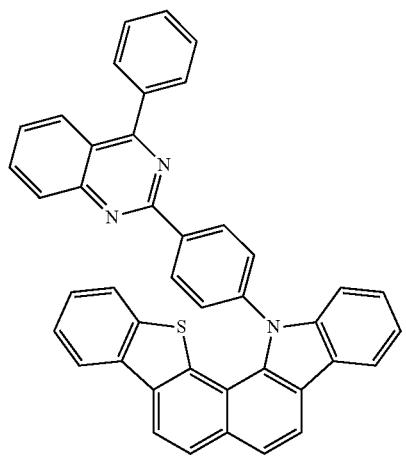
P-54
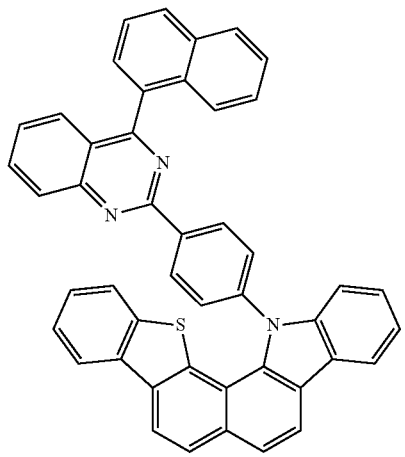
P-55
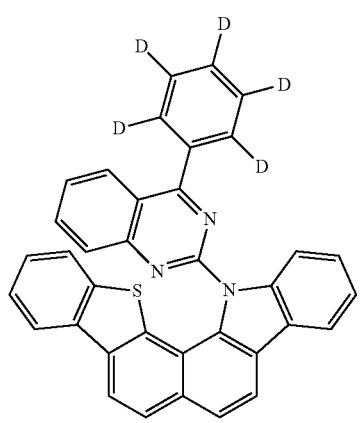
P-56
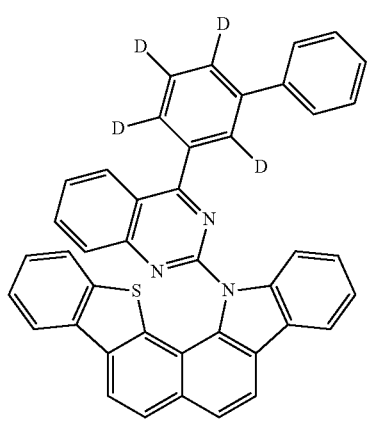
P-58
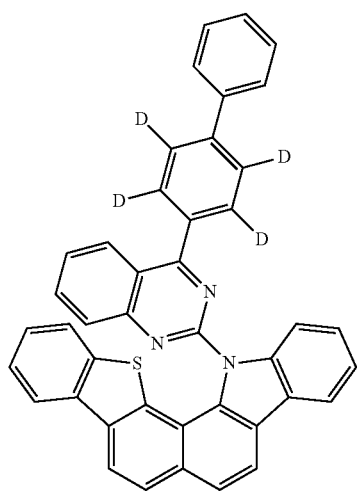
P-57
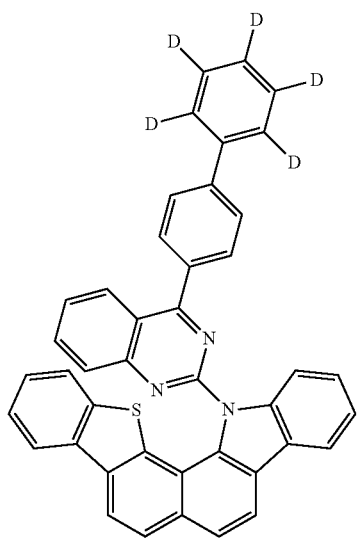

-continued
P-59
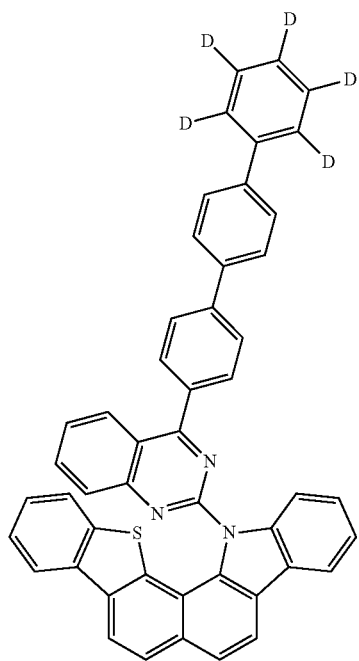
P-60
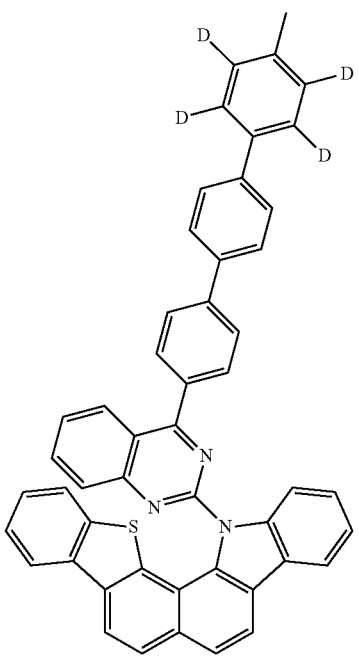
P-61
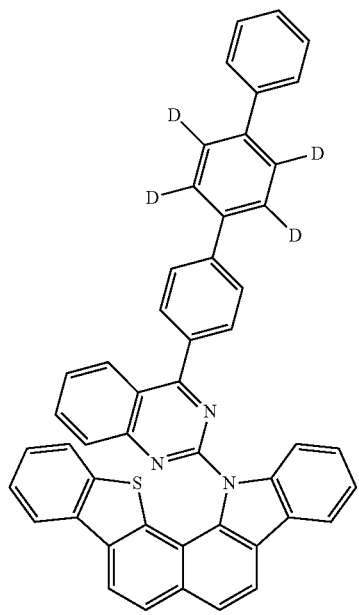
P-62
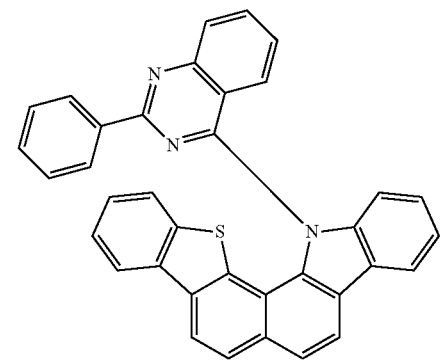
P-63
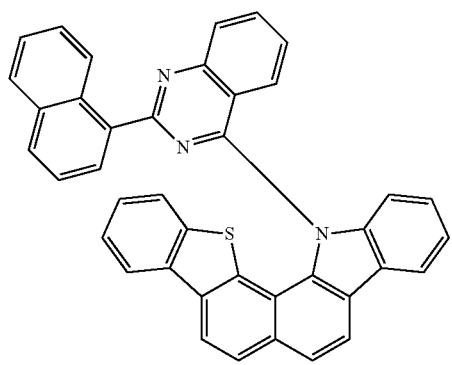
P-64
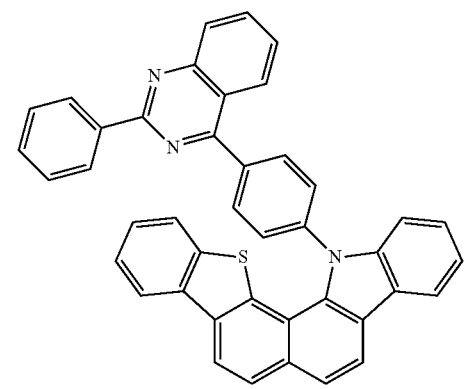

-continued
P-65
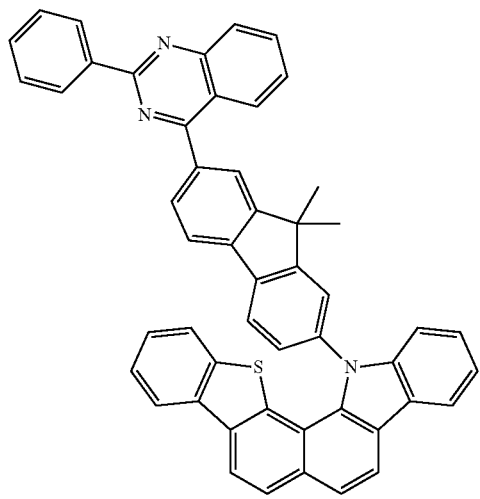
P-66
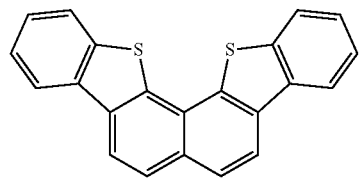
P-67
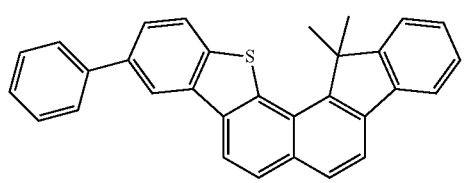
P-68
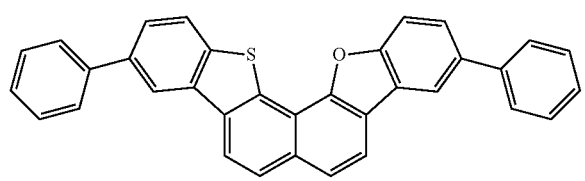
P-69
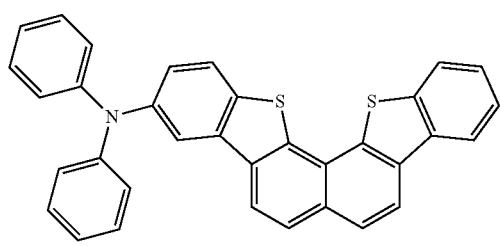
P-70
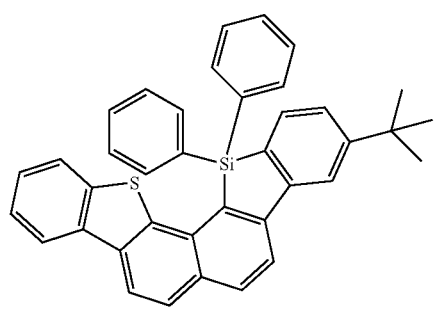
P-71
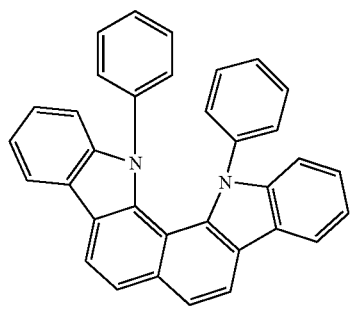
P-72
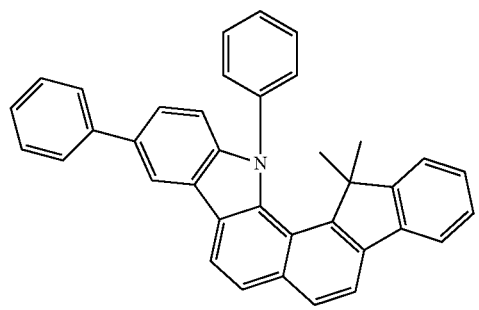

-continued
P-73
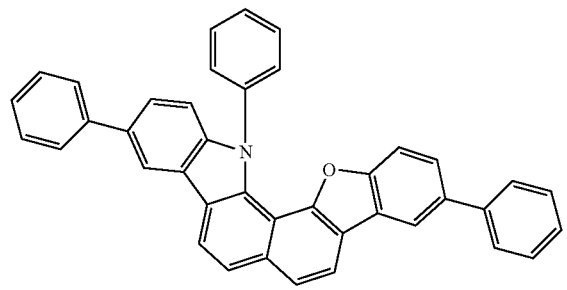
P-74
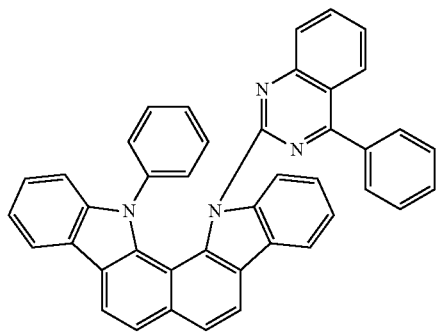
P-75
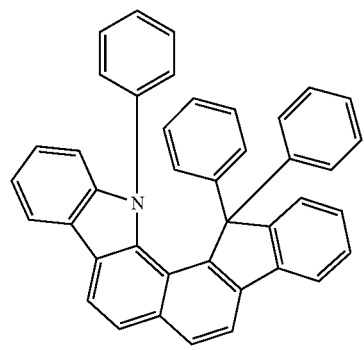
P-76
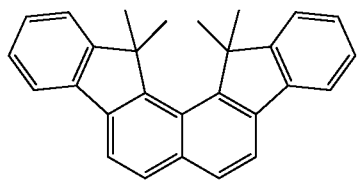
P-77
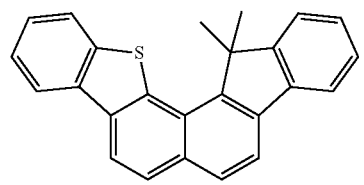
P-78
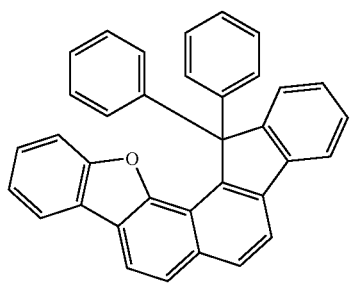
P-79
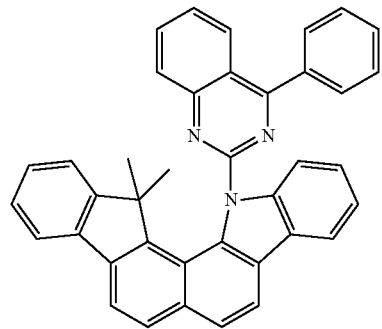
P-80
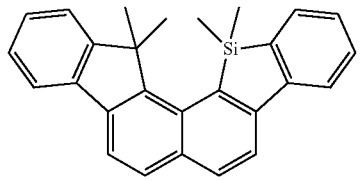

-continued
P-81
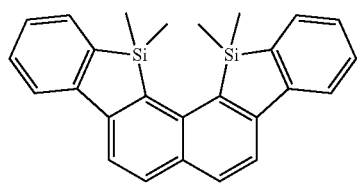
P-82
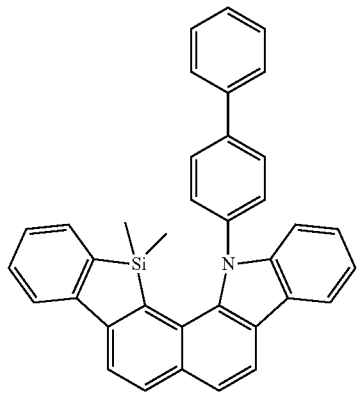
P-83
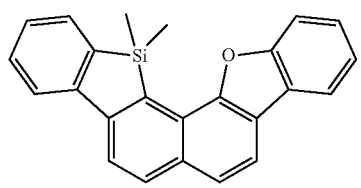
P-84
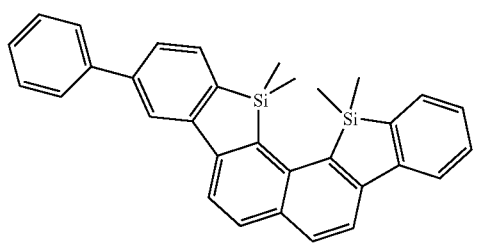
P-85
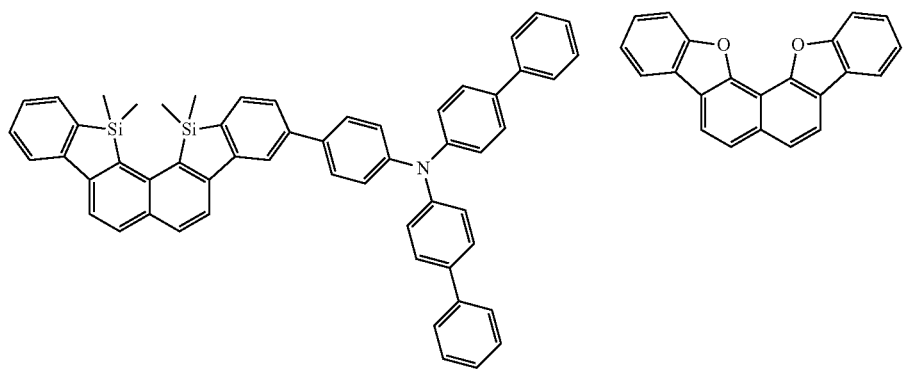
P-86
P-87
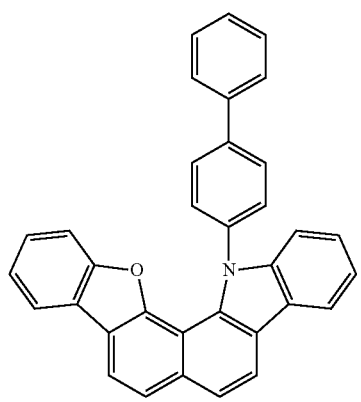
P-88
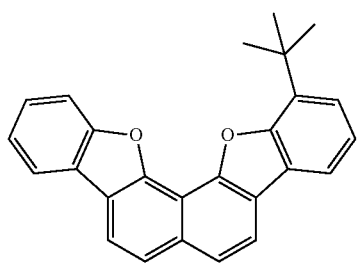

-continued
P-89
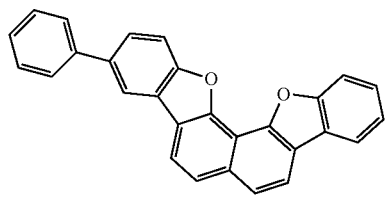
P-90
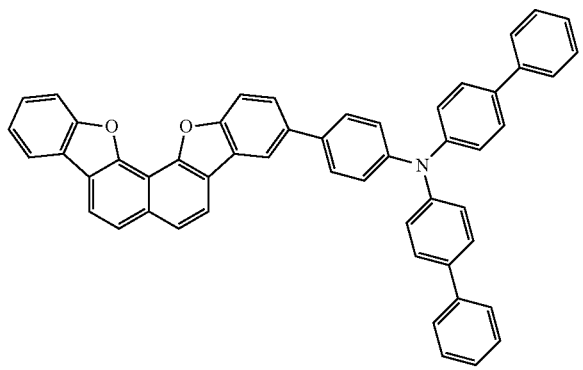
P-91
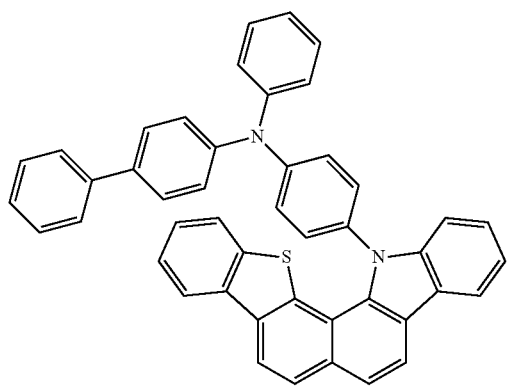
P-92
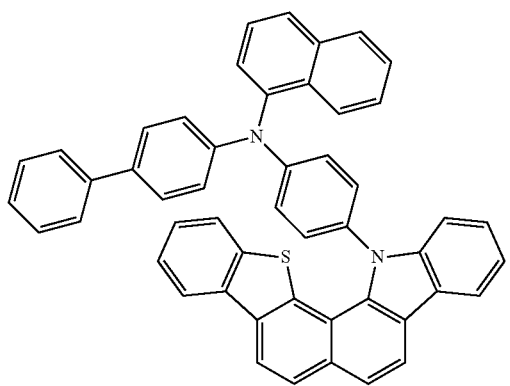
P-93
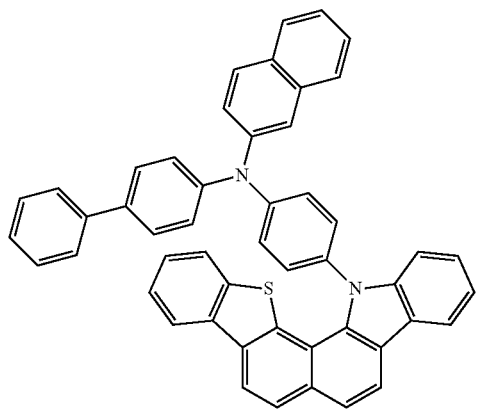
P-94
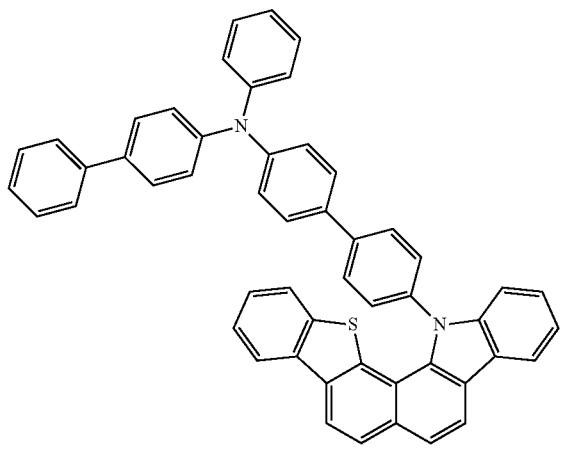

-continued
P-95
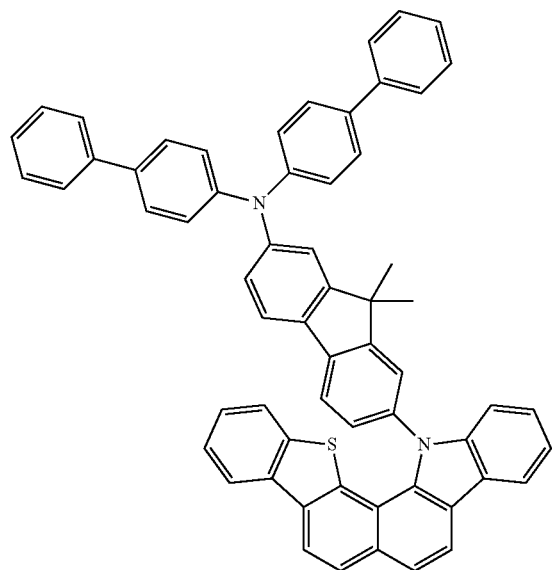
P-96
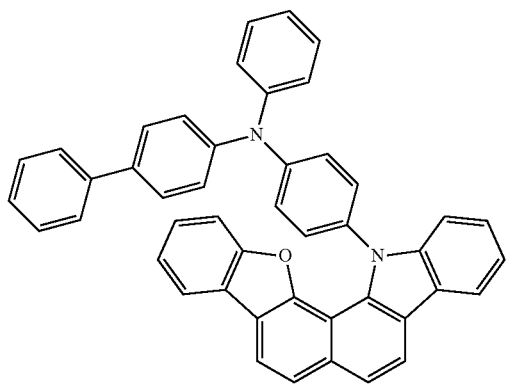
P-97
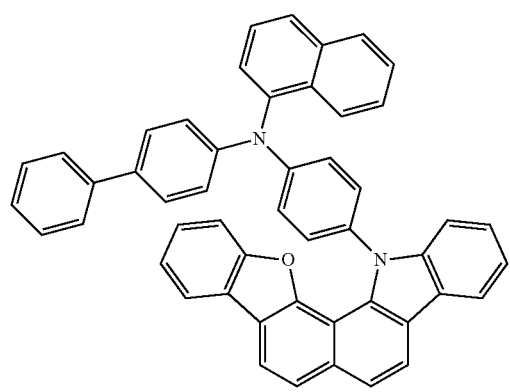
P-98
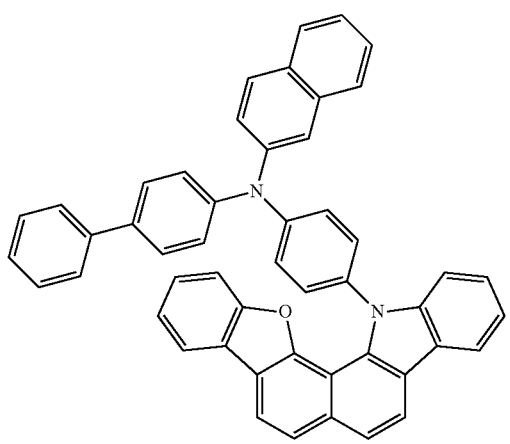
P-99
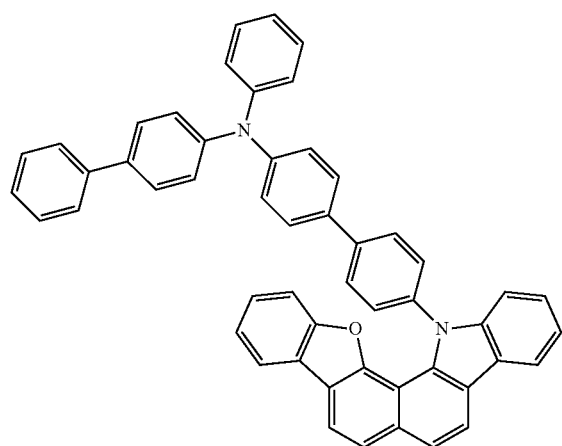
P-100
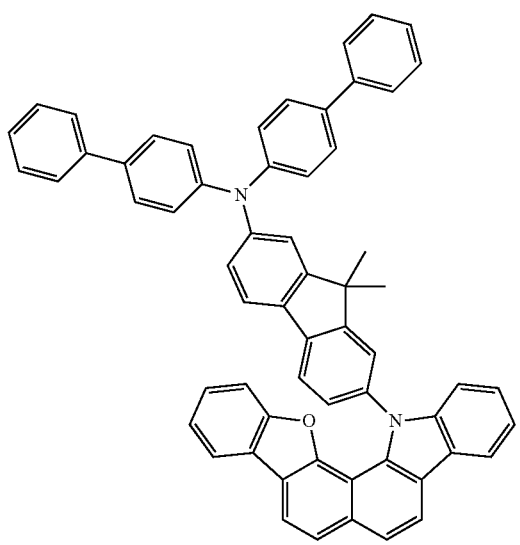

-continued
P-101
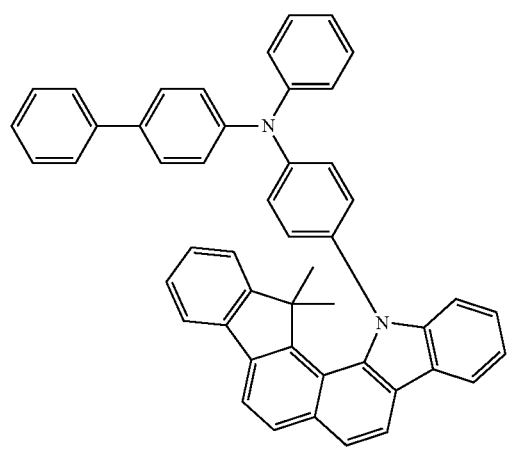
P-102
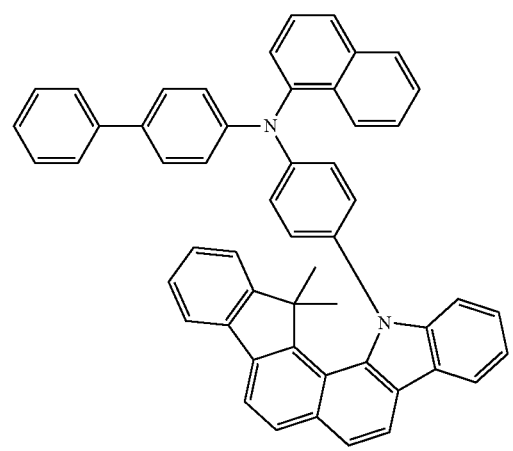
P-103
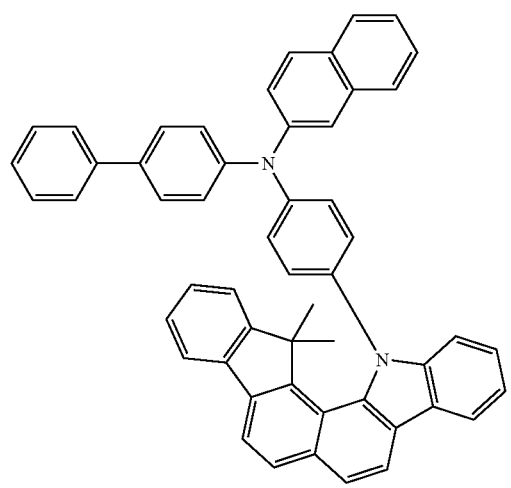
P-104
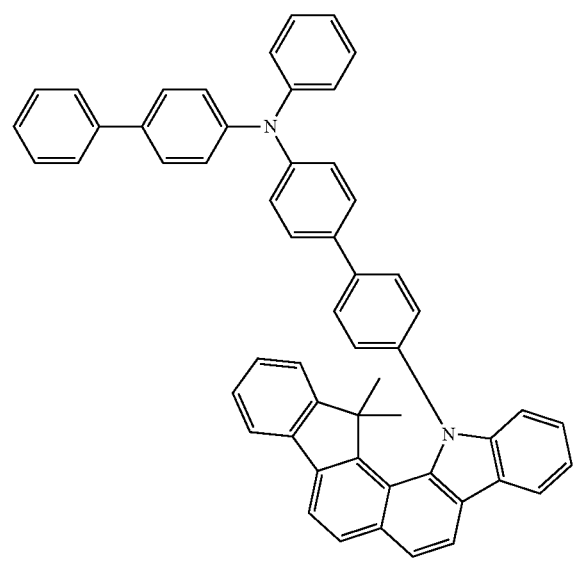
P-105
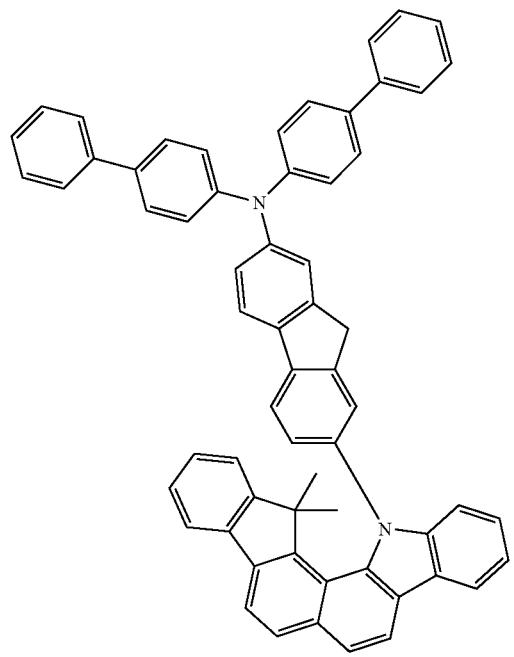
P-106
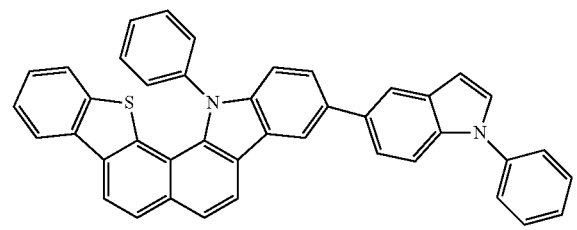

-continued
P-107
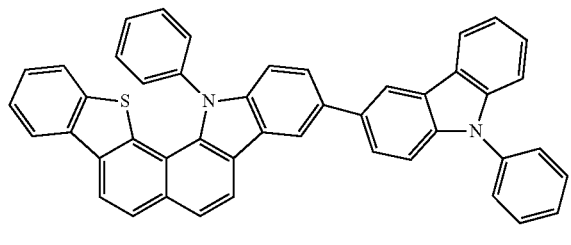
P-108
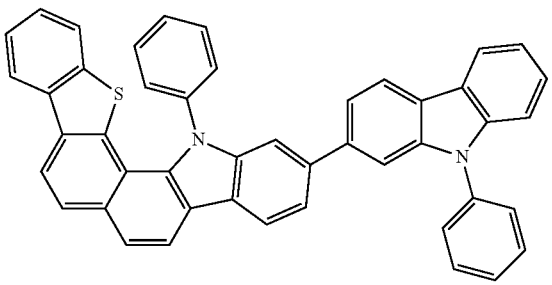
P-109
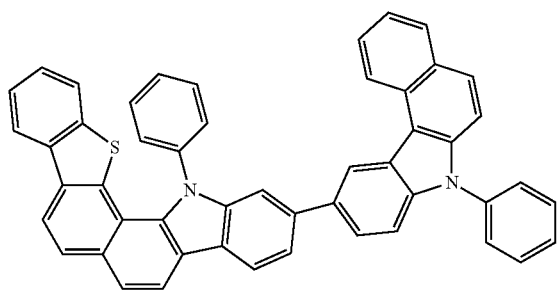
P-110
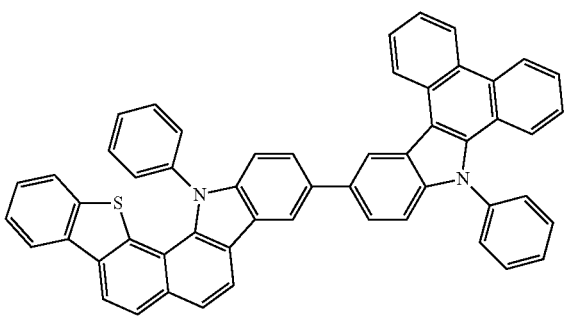
P-111
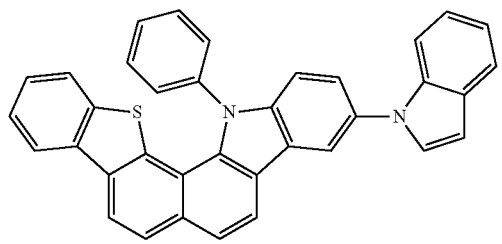
P-112
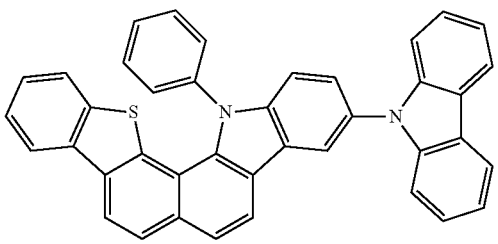
P-113
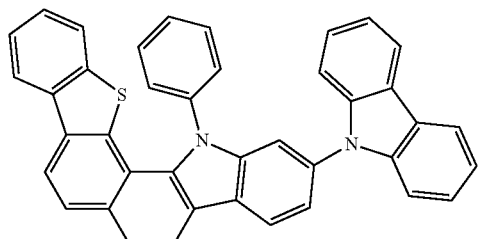
P-114
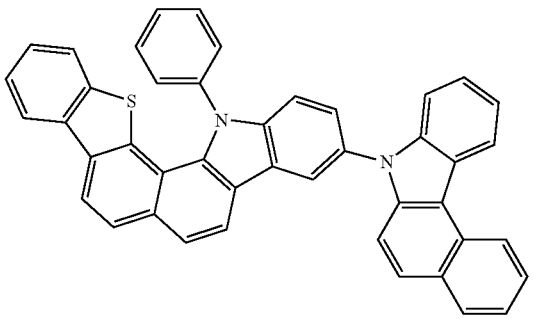
P-115
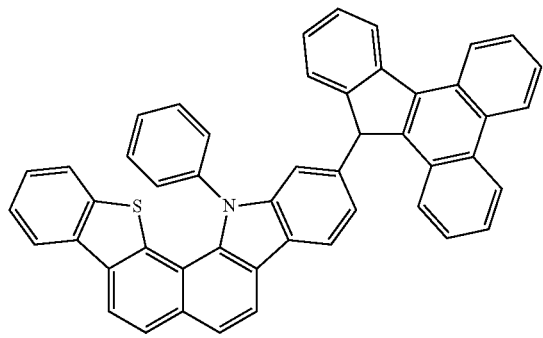
P-116
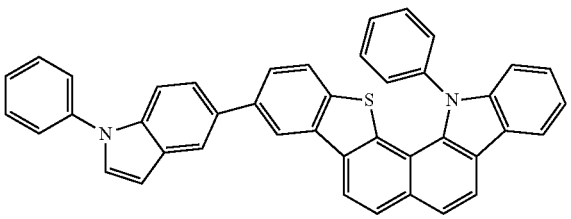

-continued
P-117
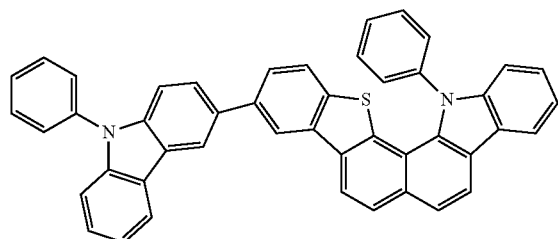
P-118
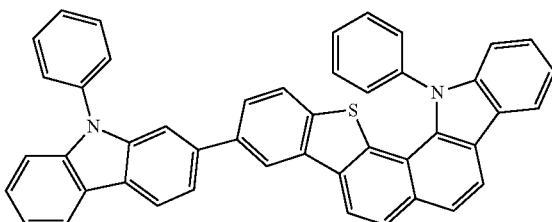
P-119
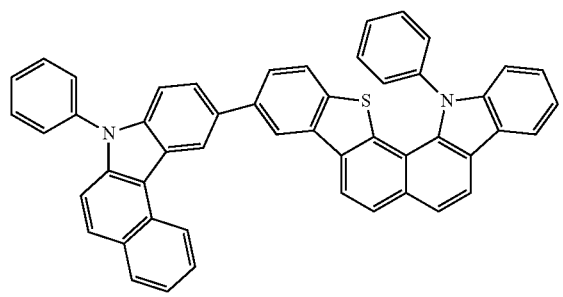
P-120
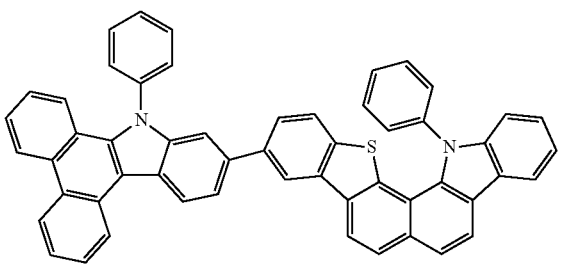
P-121
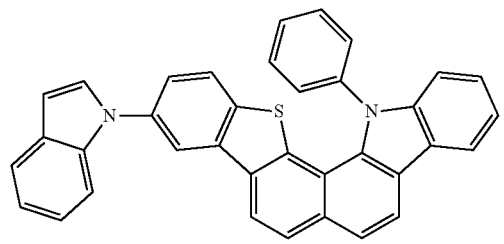
P-122
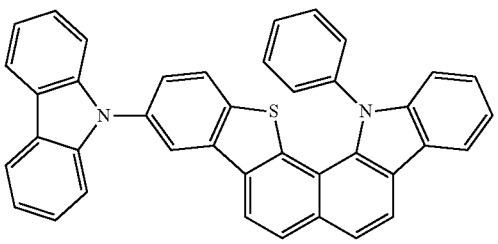
P-123
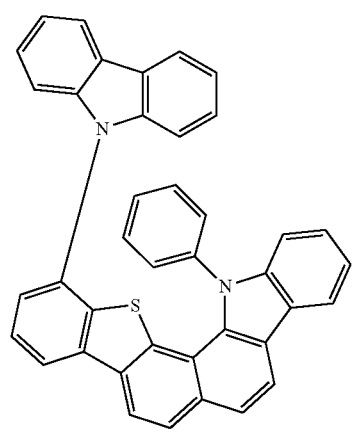
P-124
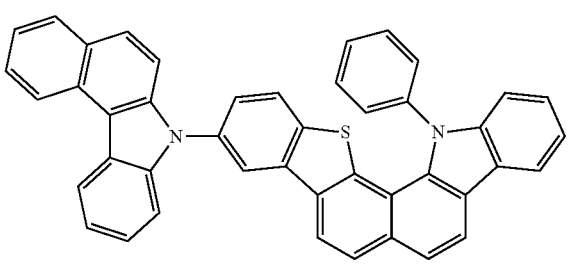
P-125
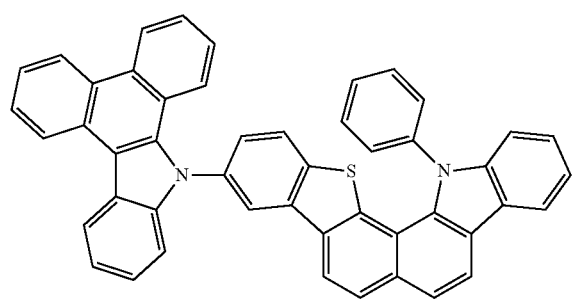
P-126
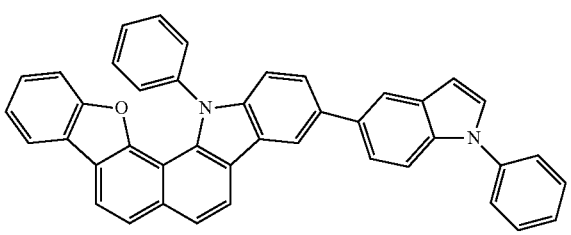

-continued
P-127
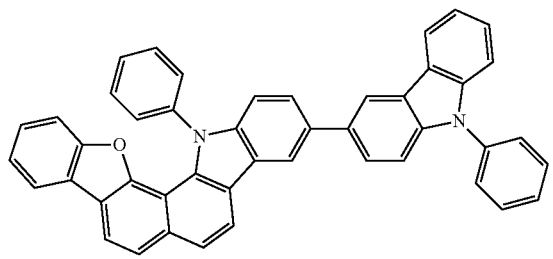
P-128
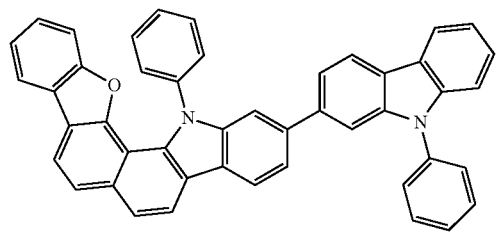
P-129
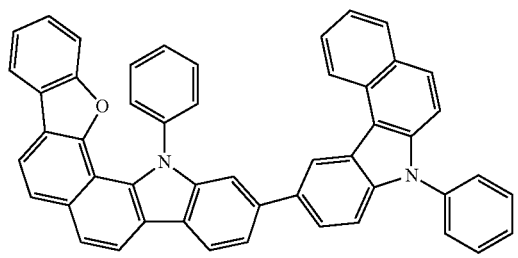
P-130
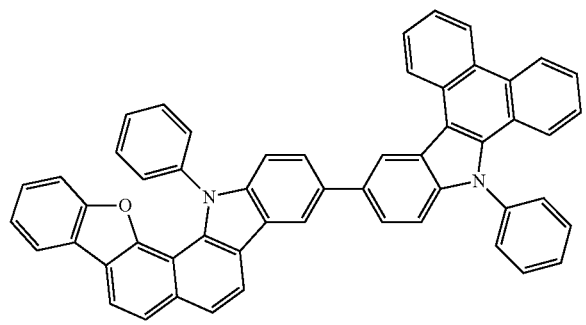
P-131
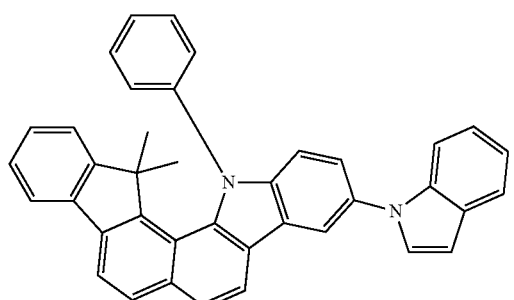
P-132
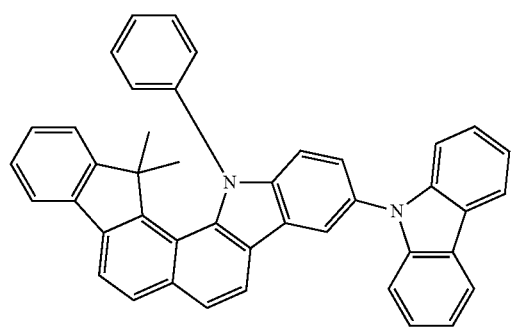
P-133
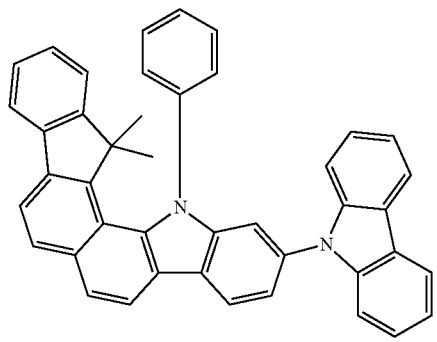
P-134
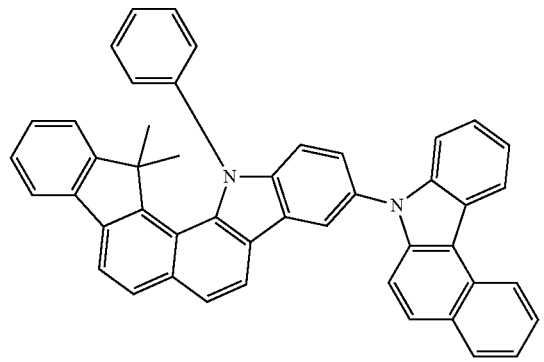
P-135
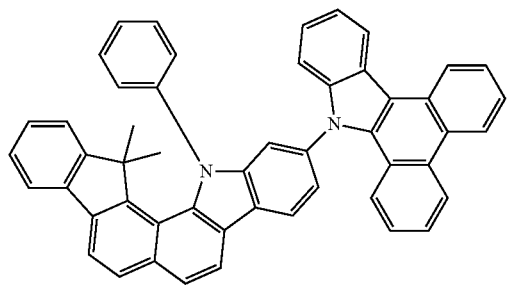
P-136
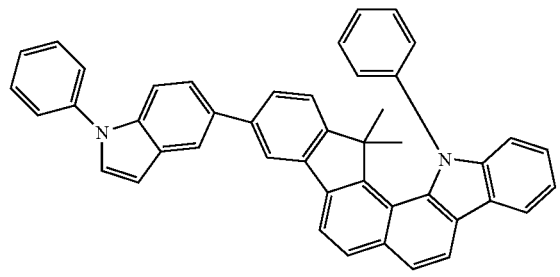

-continued
P-137
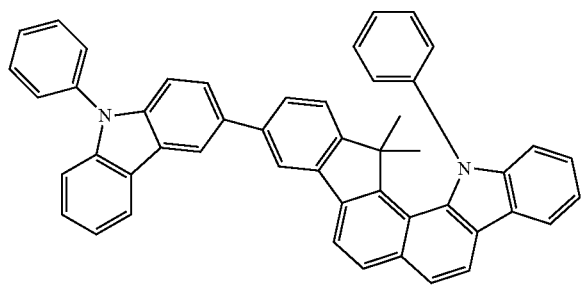
P-138
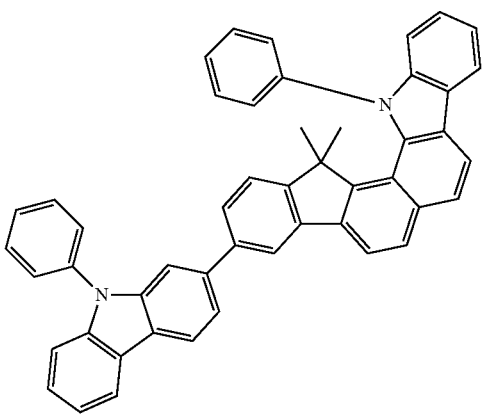
P-139
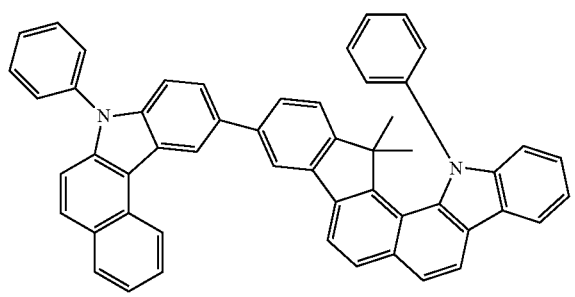
P-140
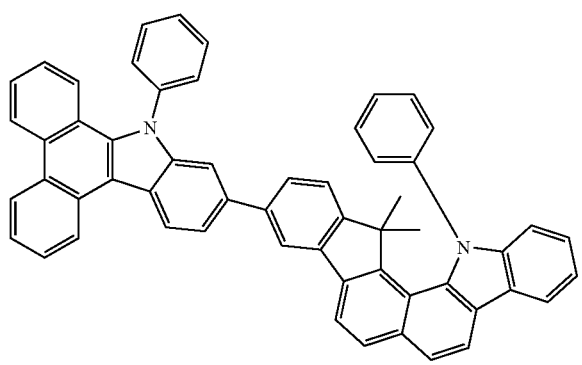
P-141
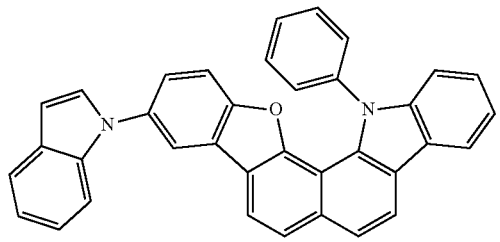
P-142
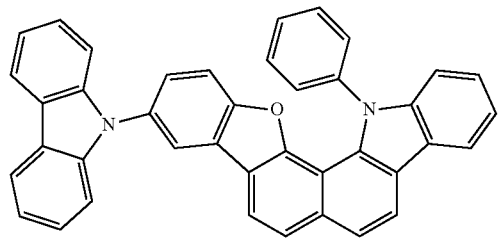
P-143
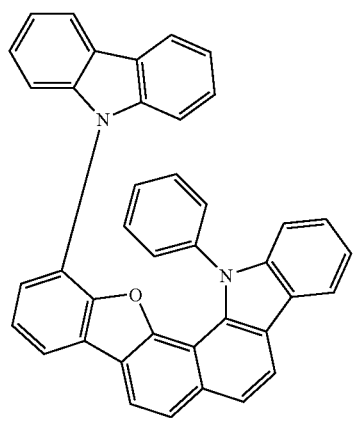
P-144
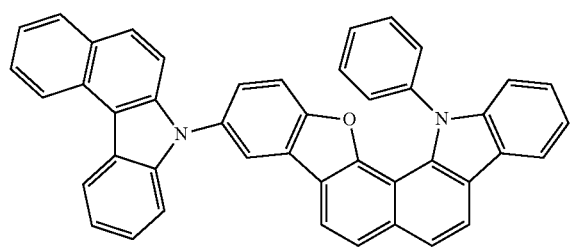

-continued
P-145
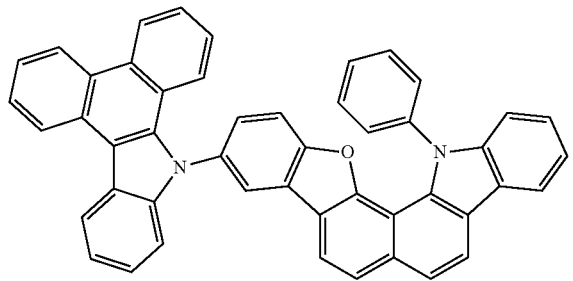
P-146
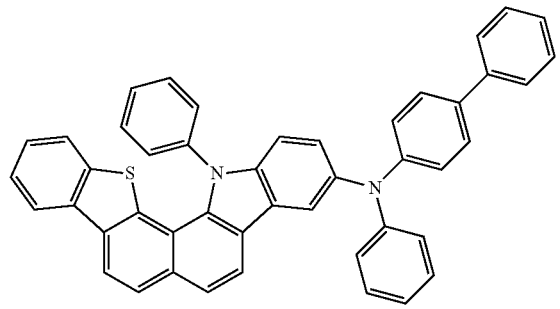
P-147
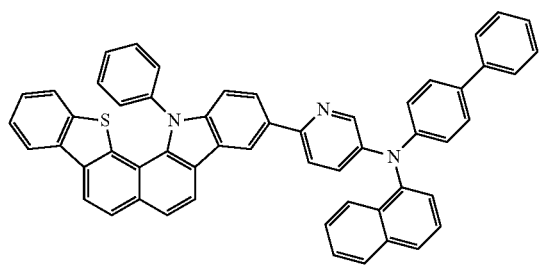
P-148
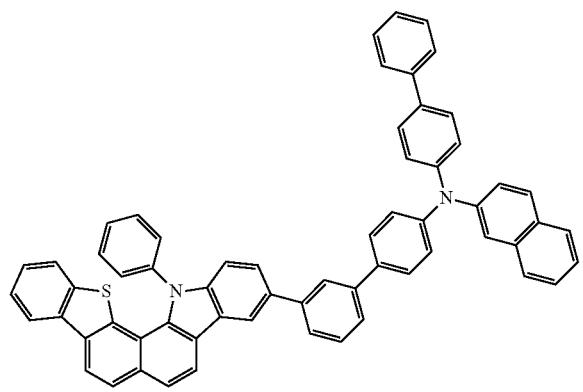
P-149
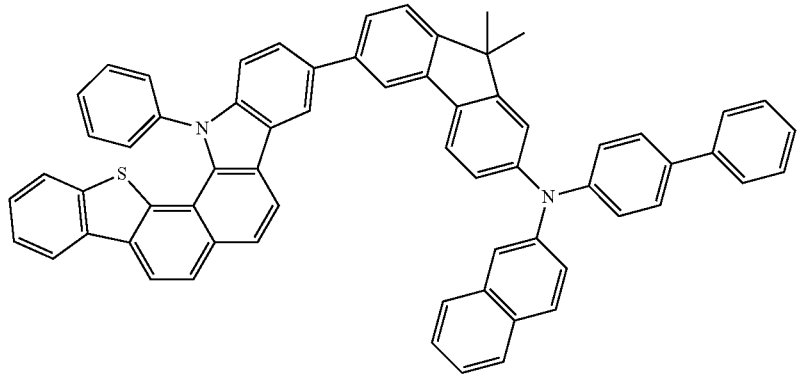
P-150
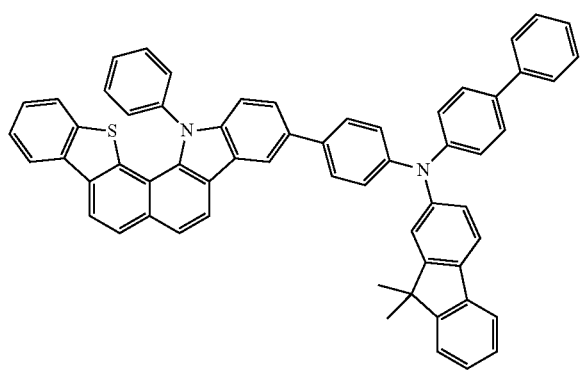
P-151
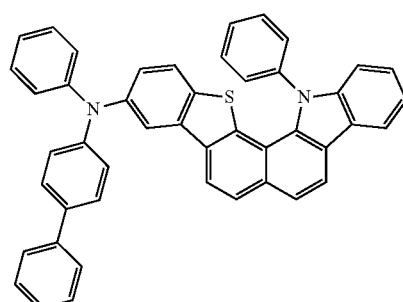

-continued
P-152
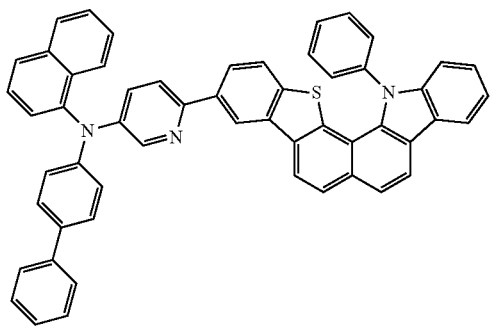
P-153
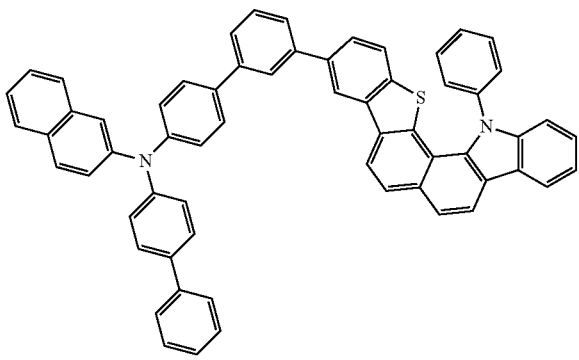
P-154
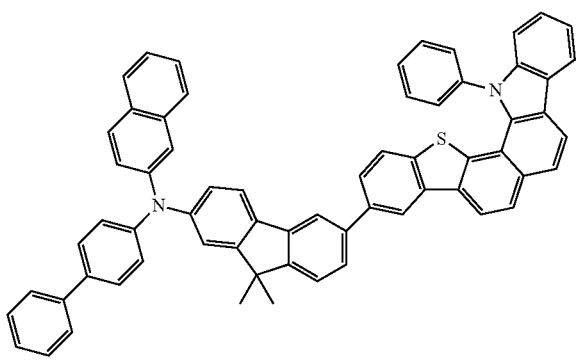
P-155
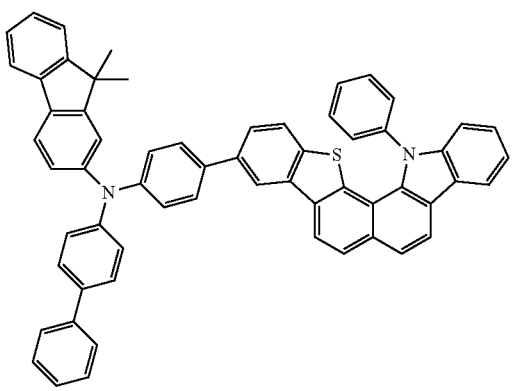
P-156
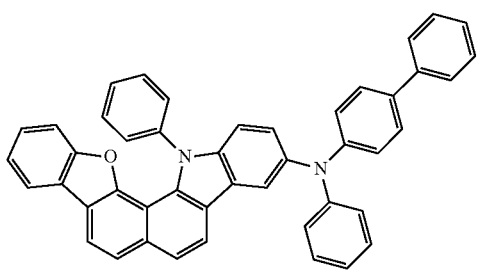
P-157
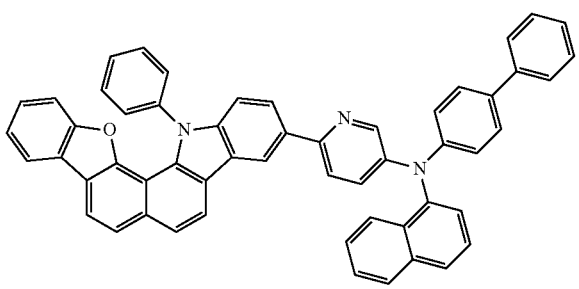
P-158
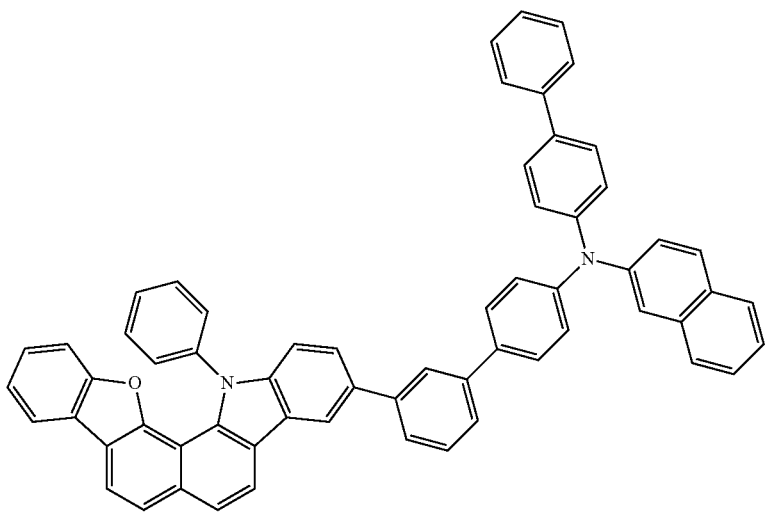

P-159
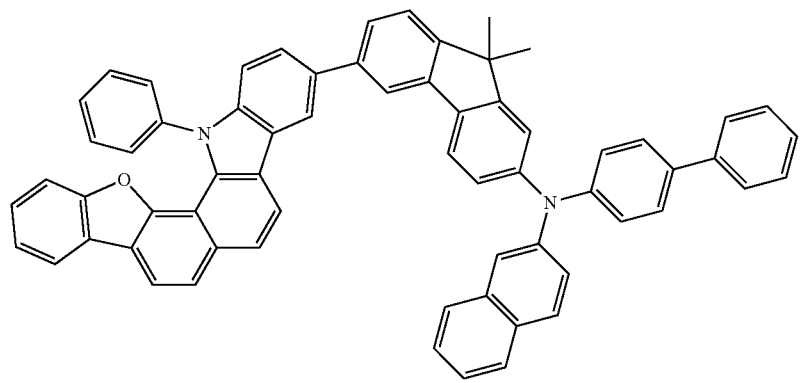
P-160
P-161
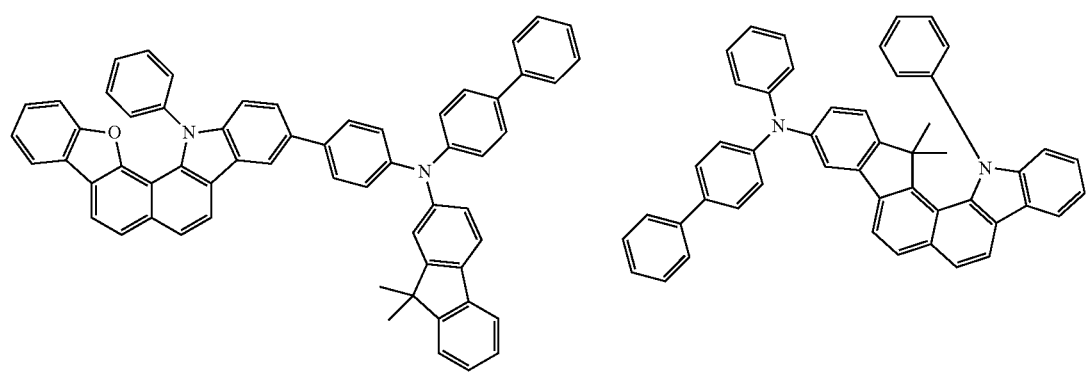
P-162
P-163
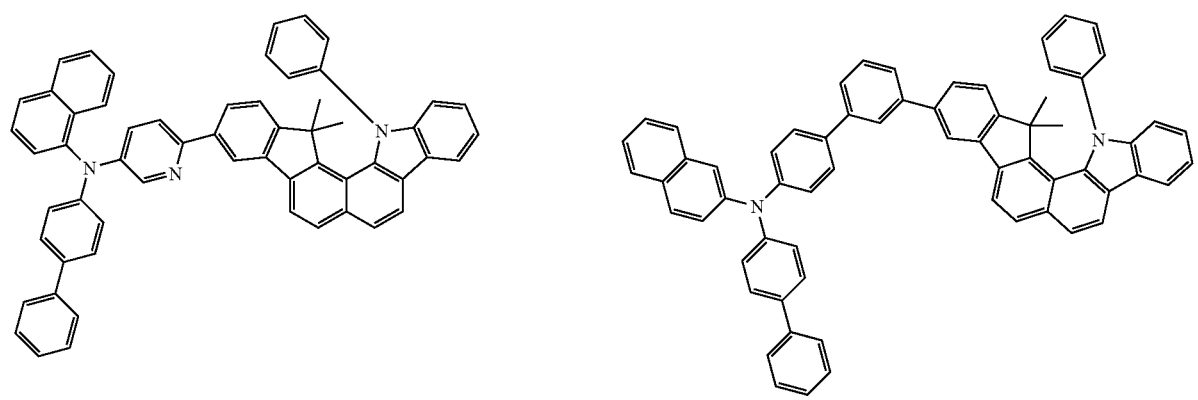
P-164
P-165
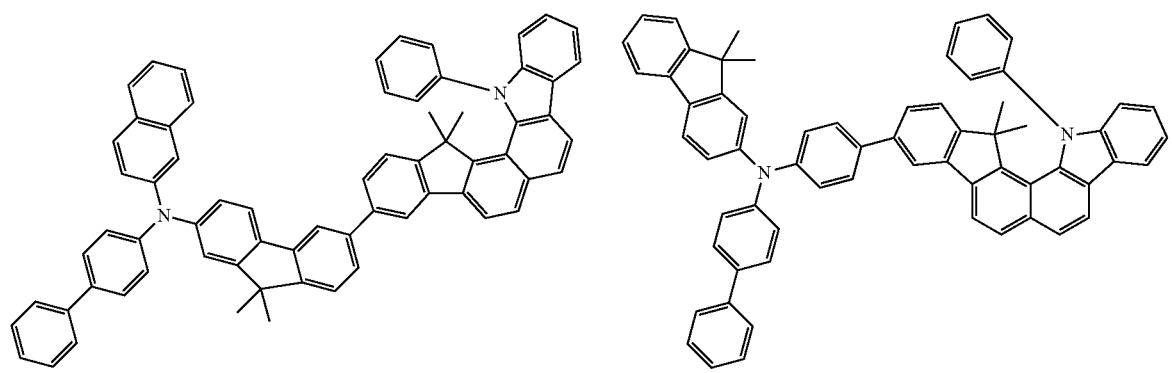

4. A organic electric element comprising a first electrode, a second electrode, and an organic material layer disposed between the first electrode and the second electrode, wherein the organic material layer comprises the compound of claim 1.

5. The organic electric element as claimed in claim 4, wherein the organic material layer is formed by a soluble process.

6. The organic electric element as claimed in claim 4, wherein the organic material layer comprises at least one of a light emitting layer, a hole transport layer, and an emission-auxiliary layer.

7. An electronic device comprising a display device, which comprises the organic electric element as claimed in claim 4, and a control unit for driving the display device.

8. The electronic device as claimed in claim 7, wherein the organic electric element comprises at least one of an organic light emitting diode, an organic solar cell, an organic photo conductor, an organic transistor, and an element for monochromatic or white illumination.

* * * * *